US009803245B2

(12) United States Patent
Zacksenhaus et al.

(10) Patent No.: US 9,803,245 B2
(45) Date of Patent: Oct. 31, 2017

(54) SIGNATURE FOR PREDICTING CLINICAL OUTCOME IN HUMAN HER2+ BREAST CANCER

(71) Applicant: University Health Network, Toronto (CA)

(72) Inventors: Eldad Zacksenhaus, Toronto (CA); Jeff Liu, Toronto (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 13/829,234

(22) Filed: Mar. 14, 2013

(65) Prior Publication Data
US 2013/0259858 A1 Oct. 3, 2013

Related U.S. Application Data

(60) Provisional application No. 61/610,792, filed on Mar. 14, 2012.

(51) Int. Cl.
*C12Q 1/68* (2006.01)
*G01N 33/74* (2006.01)
*G01N 33/574* (2006.01)

(52) U.S. Cl.
CPC ..... *C12Q 1/6886* (2013.01); *G01N 33/57415* (2013.01); *G01N 33/74* (2013.01); *C12Q 2600/106* (2013.01); *C12Q 2600/158* (2013.01)

(58) Field of Classification Search
None
See application file for complete search history.

(56) References Cited

PUBLICATIONS

ADAPT website, Paterson Institute for Cancer Research, probesets for SCRN1, printed Jul. 22, 2014.*
ADAPT website, Paterson Institute for Cancer Research, probesets for NPY, printed Jul. 22, 2014.*
ADAPT website, Paterson Institute for Cancer Research, probesets for CHAF1B, printed Jul. 22, 2014.*
ADAPT website, Paterson Institute for Cancer Research, probesets for NRP1, printed Jul. 22, 2014.*
ADAPT website, Paterson Institute for Cancer Research, probesets for CCR2, printed Jul. 22, 2014.*
ADAPT website, Paterson Institute for Cancer Research, probesets for C1QB, printed Jul. 22, 2014.*
ADAPT website, Paterson Institute for Cancer Research, probesets for VCAM1, printed Jul. 22, 2014.*
ADAPT website, Paterson Institute for Cancer Research, probesets for CD180, printed Jul. 22, 2014.*
ADAPT website, Paterson Institute for Cancer Research, probesets for KIF11, printed Jul. 22, 2014.*
Kulkarni (Current protocols in Molecular Biology, 25B.10.1-25B.10.17, published online Apr. 1, 2011).*
Harris et al (Clinical Cancer Research, 2007, 13:1198-1207).*
Eklund et al (Nature Biotechnology, 2006, 24:1071-1073).*
GeneAnnot website, probesets for CD74, printed Oct. 2015.*
GeneAnnot website, probesets for AURKB, printed Oct. 2015.*
GeneAnnot website, probesets for CCNA2, printed Oct. 2015.*
GeneAnnot website, probesets for ATP7B, printed Oct. 2015.*
GeneAnnot website, probesets for CCNB1, printed Oct. 2015.*
GeneAnnot website, probesets for CLDN8, printed Oct. 2015.*
GeneAnnot website, probesets for ITGB2, printed Oct. 2015.*
GeneAnnot website, probesets for CD72, printed Oct. 2015.*
GeneAnnot website, probesets for ST8SIA4, printed Oct. 2015.*
Abdueva et al (Journal of Molecular Diagnostics, 2006, 12: 409-417).*
Slamon DJ, Leyland-Jones B, Shak S, Fuchs H, Paton V, Bajamonde A, Fleming T, Eiermann W, Wolter J, Pegram M, Baselga J, Norton L (2001) Use of chemotherapy plus a monoclonal antibody against HER2 for metastatic breast cancer that overexpresses HER2. N Engl J Med 344(11):783-792.
Abramson V,Arteaga CL (2011) New strategies in HER2-overexpressing breast cancer: many combinations of targeted drugs available. Clin Cancer Res 17(5):952-958.
Dean-ColombW,Esteva FJ (2008) Her2-positive breast cancer: herceptin and beyond. Eur J Cancer 44(18):2806-2812.
Martin M, Esteva FJ, Alba E, Khandheria B, Perez-Isla L, Garcia-Saenz JA, Marquez A, Sengupta P, Zamorano J (2009) Minimizing cardiotoxicity while optimizing treatment efficacy with trastuzumab: review and expert recommendations. Oncologist 14(1):1-11.
Cicalese A, Bonizzi G, Pasi CE, Faretta M, Ronzoni S, Giulini B, Brisken C, Minucci S, Di Fiore PP, Pelicci PG (2009) The tumor suppressor p53 regulates polarity of self-renewing divisions in mammary stem cells. Cell 138(6):1083-1095.
Korkaya H, Paulson A, Iovino F, Wicha MS (2008) HER2 regulates the mammary stem/progenitor cell population driving tumorigenesis and invasion. Oncogene, 2008, vol. 27, pp. 6120-6130.
Desmedt C, Haibe-Kains B, Wirapati P, Buyse M, Larsimont D, Bontempi G, Delorenzi M, Piccart M, Sotiriou C (2008) Biological processes associated with breast cancer clinical outcome depend on the molecular subtypes. Clin Cancer Res 14(16):5158-5165.

(Continued)

*Primary Examiner* — Laura B Goddard
(74) *Attorney, Agent, or Firm* — Bereskin & Parr LLP; Carmela De Luca

(57) ABSTRACT

A method of predicting outcome in a subject with for example Her2+ (ERα–) breast cancer comprising: (a) determining a HTICs expression signature comprising determining an expression level of 2 or more HTICS biomarkers selected from Aurkb, Ccna2, Scrn1, Npy, Atp7b, Chaf1b, Ccnb1, Cldn8, Nrp1, Ccr2, C1qb, Cd74, Vcam1, Cd180, Itgb2, Cd72, St8sia4, Kif11, Plk1, Chek1, Mphosph6, Cora1a, Ccl5, Cd3e, Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86; and (b) calculating a signature score, the signature score comprising a sum of HTICs biomarker expression parameters; wherein a signature score greater than a selected cut-off or control signature score is indicative of a poor outcome (HTICS+) and a signature score less than a selected cut-off is indicative of a good outcome (HTICS–). The methods can be used to prognose outcome and/or select suitable treatment. Arrays and kits for use with the methods are also provided.

9 Claims, 25 Drawing Sheets

(56) References Cited

PUBLICATIONS

Paik S, Shak S, Tang G, Kim C, Baker J, Cronin M, Baehner FL, Walker MG, Watson D, Park T, Hiller W, Fisher ER, Wickerham DL, Bryant J, Wolmark N (2004) A multigene assay to predict recurrence of tamoxifen-treated, node-negative breast cancer. N Engl J Med 351(27):2817-2826.

Liu R, Wang X, Chen GY, Dalerba P, Gurney A, Hoey T, Sherlock G, Lewicki J, Shedden K, Clarke MF (2007) The prognostic role of a gene signature from tumorigenic breast-cancer cells. N Engl J Med 356(3):217-226.

Finak G, Bertos N, Pepin F, Sadekova S, Souleimanova M, Zhao H, Chen H, Omeroglu G, Meterissian S, Omeroglu A, Hallett M, Park M (2008) Stromal gene expression predicts clinical outcome in breast cancer. Nat Med 14(5):518-527.

Guy CT, Webster MA, Schaller M, Parsons TJ, Cardiff RD, Muller WJ (1992) Expression of neuprotooncogene in the mammary epithelium of transgenic mouse induces metastatic disease. Proc. Natl. Acad. Sci. USA 89:10578-10582.

Liu JC, Deng T, Lehal RS, Kim J, Zacksenhaus E (2007) Identification of Tumorsphere- and Tumor-Initiating Cells in HER2/Neu-Induced Mammary Tumors. Cancer Res 67(18):8671-8681.

Vaillant F, Asselin-Labat ML, Shackleton M, Forrest NC, Lindeman GJ, Visvader JE (2008) The mammary progenitor marker CD61/beta3 integrin identifies cancer stem cells in mouse models of mammary tumorigenesis. Cancer Res 68(19):7711-7717.

Reedijk M, Odorcic S, Chang L, Zhang H, Miller N, McCready DR, Lockwood G, Egan SE (2005) High-level coexpression of JAG1 and NOTCH1 is observed in human breast cancer and is associated with poor overall survival. Cancer Res 65(18):8530-8537.

Osipo C, Patel P, Rizzo P, Clementz AG, Hao L, Golde TE, Miele L (2008) ErbB-2 inhibition activates Notch-1 and sensitizes breast cancer cells to a gamma-secretase inhibitor. Oncogene 27(37):5019-5032.

Kmieciak M, Knutson KL, Dumur CI, Manjili MH (2007) HER-2/neu antigen loss and relapse of mammary carcinoma are actively induced by T cell-mediated anti-tumor immune responses. Eur J Immunol 37(3):675-685.

Notta F, Mullighan CG, Wang JC, Poeppl A, Doulatov S, Phillips LA, Ma J, Minden MD, Downing JR, Dick JE (2011) Evolution of human BCR-ABL1 lymphoblastic leukaemia-initiating cells. Nature 469(7330):362-367.

Subramanian A, Tamayo P, Mootha VK, Mukherjee S, Ebert BL, Gillette MA, Paulovich A, Pomeroy SL, Golub TR, Lander ES, Mesirov JP (2005) Gene set enrichment analysis: a knowledge-based approach for interpreting genome-wide expression profiles. ProcNatlAcadSci U S A 102(43):15545-15550.

Merico D, Isserlin R, Stueker O, Emili A, Bader GD (2011) Enrichment map: a network-based method for gene-set enrichment visualization and interpretation. PLoS One 5(11):e13984.

Staaf J, Ringner M, Vallon-Christersson J, Jonsson G, Bendahl PO, Holm K, Arason A, Gunnarsson H, Hegardt C, Agnarsson BA, Luts L, Grabau D, Ferno M, Malmstrom PO, Johannsson OT, Loman N, Barkardottir RB, Borg A (2010) Identification of subtypes in human epidermal growth factor receptor 2-positive breast cancer reveals a gene signature prognostic of outcome. J ClinOncol 28(11):1813-1820.

Shirley SH, Rundhaug JE, Tian J, Cullinan-Ammann N, Lambertz I, Conti CJ, Fuchs-Young R (2009) Transcriptional regulation of estrogen receptor-alpha by p53 in human breast cancer cells. Cancer Res 69(8):3405-3414.

ValastyanS,Weinberg RA (2011) Tumor metastasis: molecular insights and evolving paradigms. Cell 147(2):275-292.

Geiss GK, Bumgarner RE, Birditt B, Dahl T, Dowidar N, Dunaway DL, Fell HP, Ferree S, George RD, Grogan T, James JJ, Maysuria M, Mitton JD, Oliveri P, Osborn JL, Peng T, Ratcliffe AL, Webster PJ, Davidson EH, Hood L, Dimitrov K (2008) Direct multiplexed measurement of gene expression with color-coded probe pairs. Nat Biotechnol 26(3):317-325.

Jiang Z, Deng T, Jones R, Li H, Herschkowitz JI, Liu JC, Weigman VJ, Tsao MS, Lane TF, Perou CM, Zacksenhaus E (2010) Rb deletion in mouse mammary progenitors induces luminal-B or basal-like/EMT tumor subtypes depending on p53 status. J Clin Invest 120(9):3296-3309.

* cited by examiner

Figure 9A-B
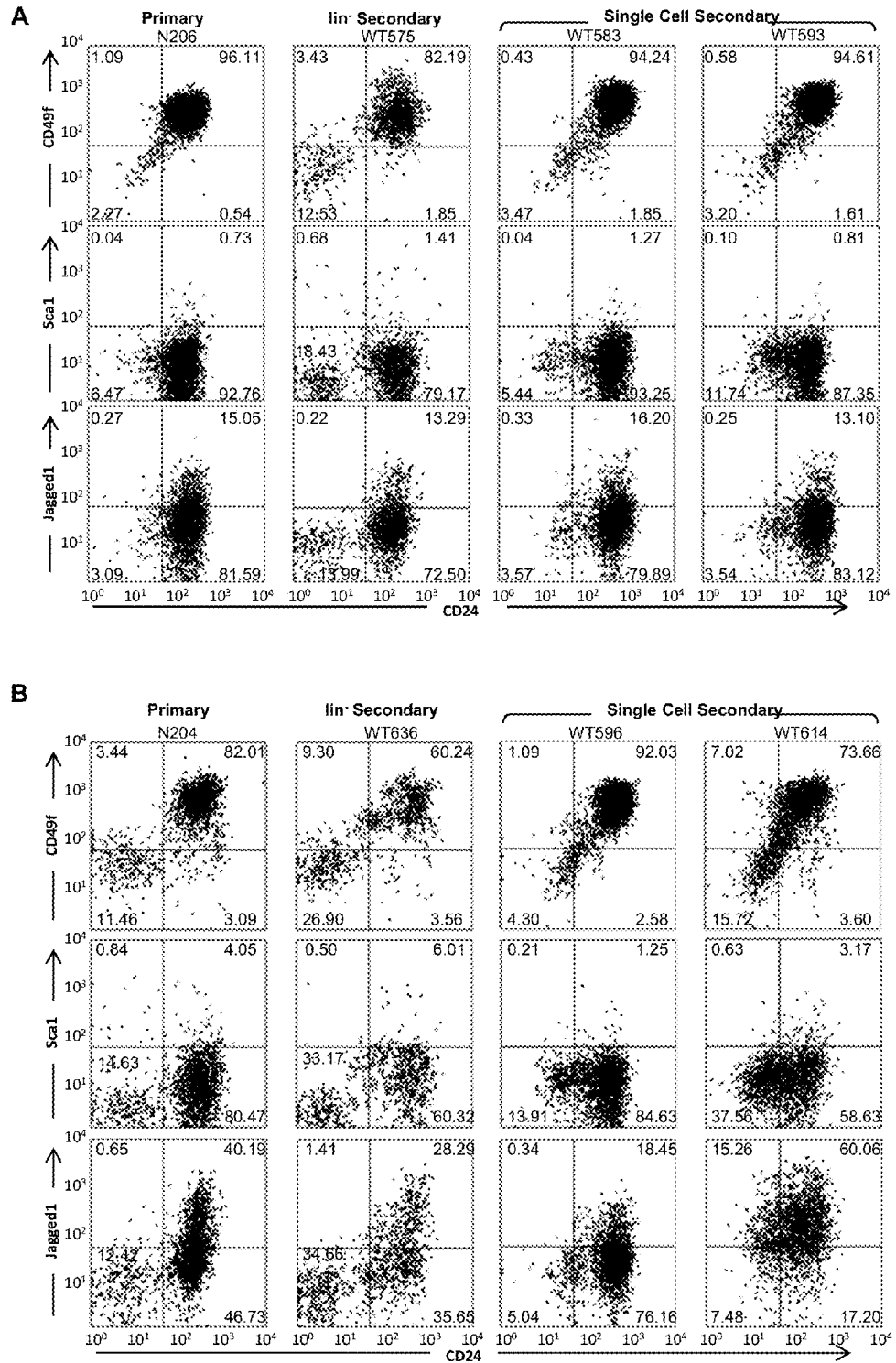

| Tumor | CD24⁻:JAG1⁻ | CD24⁺:JAG1⁻ | CD24⁻:JAG1⁺ | CD24⁺:JAG1⁺ |
|---|---|---|---|---|
| Primary Tumors (n=6) | 2.6 ± 4.9 | 76.5 ± 15.3 | 0.4 ± 0.2 | 20.5 ± 10.8 |
| Secondary Single Cell Tumors (n=7) | 4.8 ± 1.1 | 78.0 ± 7.1 | 0.4 ± 0.2 | 16.8 ± 6.7 |
| Secondary lin⁻ Tumors (n=2) | 24.3 ± 14.6 | 54.1 ± 26.1 | 0.8 ± 0.8 | 20.8 ± 10.6 |

Figure 9D-E
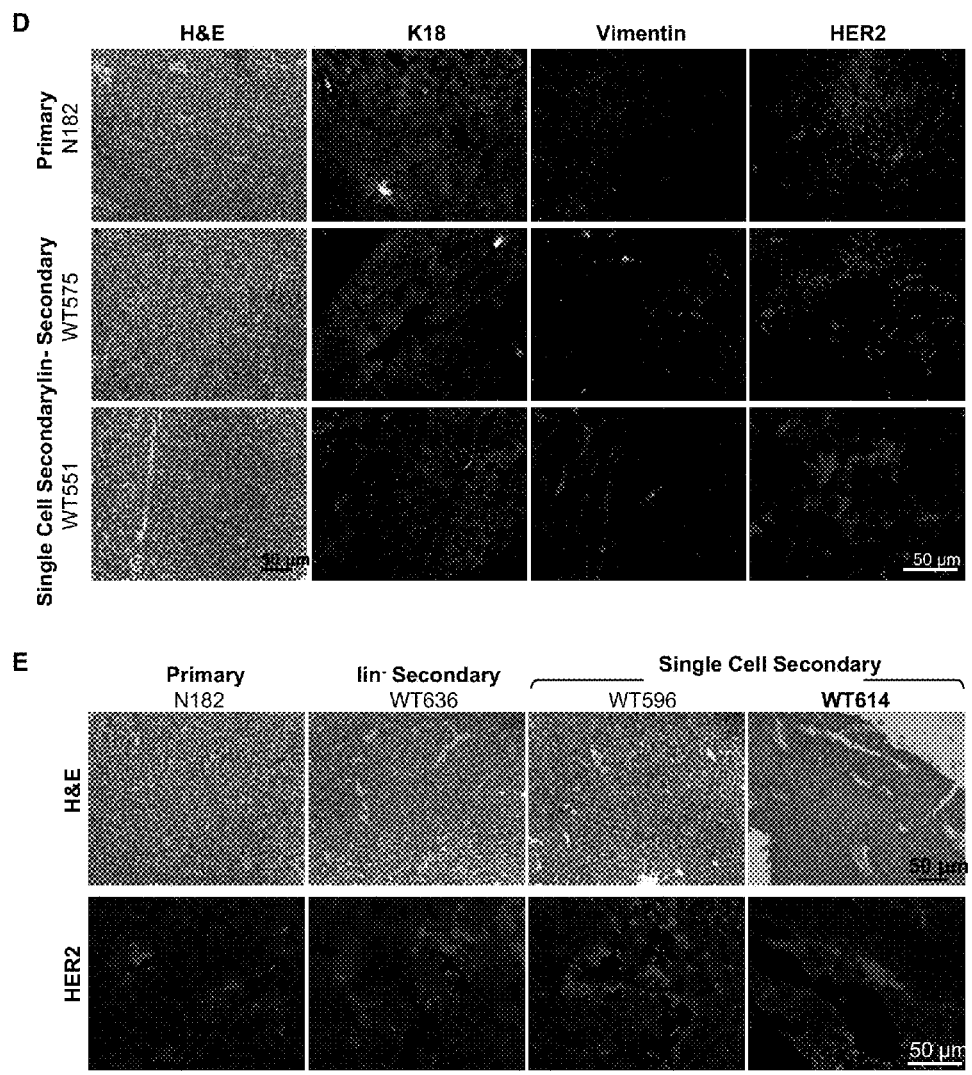

Figure 9G-I
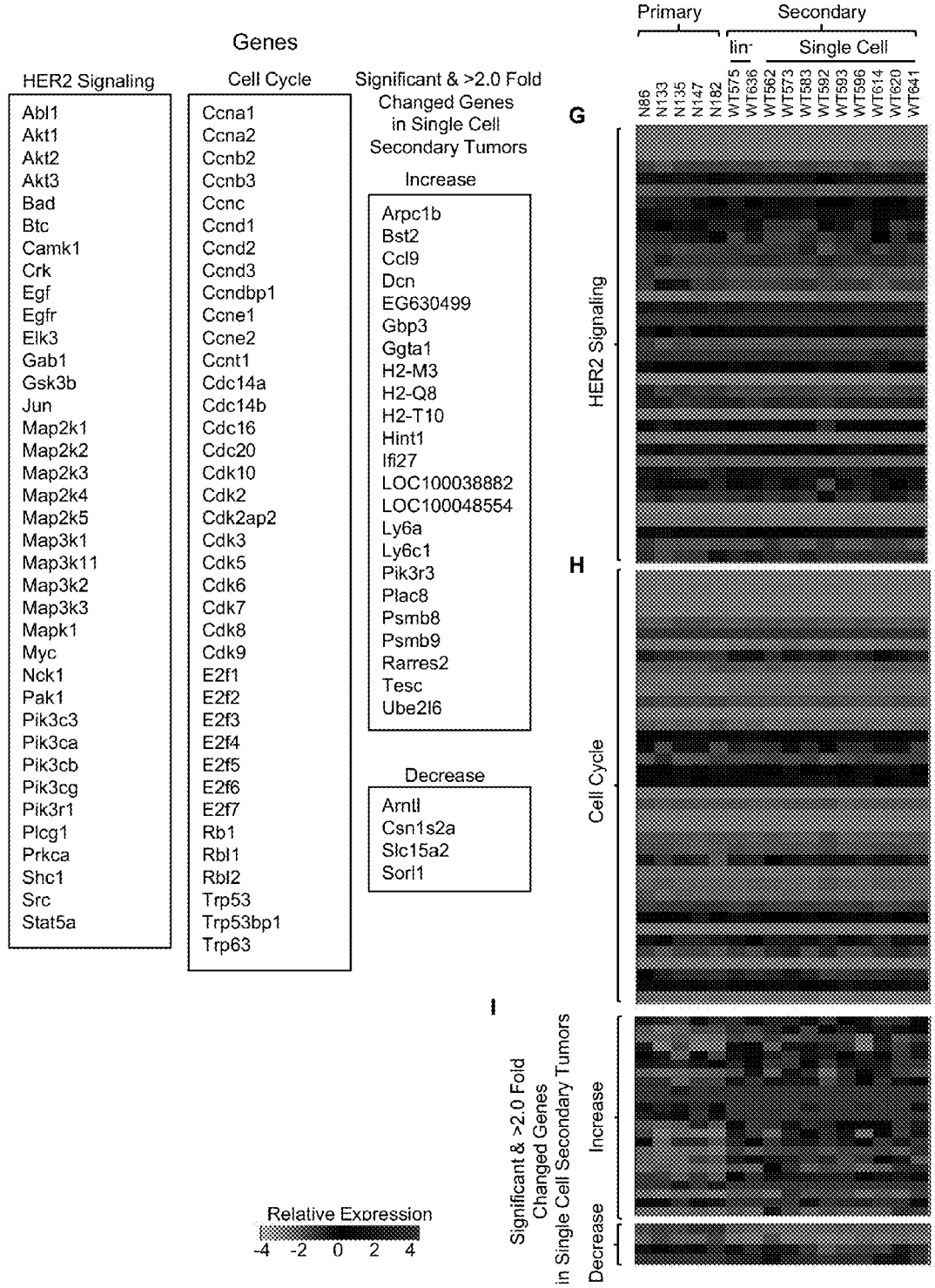

List of Genes with Significant Decrease of Expression (≤0.5X) in Single Cell Secondary Tumors

| Gene | Fold | Description |
|---|---|---|
| Lamb3 | 0.4 | Mus musculus laminin, beta 3 (Lamb3), mRNA. |
| Slc15a2 | 0.4 | Mus musculus solute carrier family 15 (H+/peptide transporter), member 2 (Slc15a2), mRNA. |
| Arntl | 0.5 | Mus musculus aryl hydrocarbon receptor nuclear translocator-like (Arntl), mRNA. |
| Sorl1 | 0.5 | Mus musculus sortilin-related receptor, LDLR class A repeats-containing (Sorl1), mRNA. |

K

List of Genes with Significant Increase of Expression (≥2X) in Single Cell Secondary Tumors

| Gene | Fold | Description |
|---|---|---|
| Ifi27 | 5.3 | Mus musculus interferon, alpha-inducible protein 27 (Ifi27), mRNA. |
| LOC100038882 | 3.7 | PREDICTED: Mus musculus hypothetical protein LOC100038882 (LOC100038882), mRNA. |
| Ly6a | 3.3 | Mus musculus lymphocyte antigen 6 complex, locus A (Ly6a), mRNA. |
| Bst2 | 3.3 | Mus musculus bone marrow stromal cell antigen 2 (Bst2), mRNA. |
| Arpc1b | 2.6 | Mus musculus actin related protein 2/3 complex, subunit 1B (Arpc1b), mRNA. |
| Psmb8 | 2.4 | Mus musculus proteasome (prosome, macropain) subunit, beta type 8 (large multifunctional peptidase 7) (Psmb8), mRNA. |
| Plac8 | 2.3 | Mus musculus placenta-specific 8 (Plac8), mRNA. |
| Psmb9 | 2.3 | Mus musculus proteasome (prosome, macropain) subunit, beta type 9 (large multifunctional peptidase 2) (Psmb9), mRNA. |
| Ly6c1 | 2.3 | Mus musculus lymphocyte antigen 6 complex, locus C1 (Ly6c1), mRNA. |
| Hint1 | 2.2 | Mus musculus histidine triad nucleotide binding protein 1 (Hint1), mRNA. |
| Rarres2 | 2.2 | Mus musculus retinoic acid receptor responder (tazarotene induced) 2 (Rarres2), mRNA. |
| Ube2l6 | 2.2 | Mus musculus ubiquitin-conjugating enzyme E2L 6 (Ube2l6), mRNA. |
| H2-T10 | 2.1 | Mus musculus histocompatibility 2, T region locus 10 (H2-T10), mRNA. |
| Ccl9 | 2.0 | Mus musculus chemokine (C-C motif) ligand 9 (Ccl9), mRNA. |
| H2-Q8 | 2.0 | Mus musculus histocompatibility 2, Q region locus 8 (H2-Q8), mRNA. |
| H2-M3 | 2.0 | Mus musculus histocompatibility 2, M region locus 3 (H2-M3), mRNA. |

Figure 11A-C

A GSE3143 Training Set – HER2+ Samples

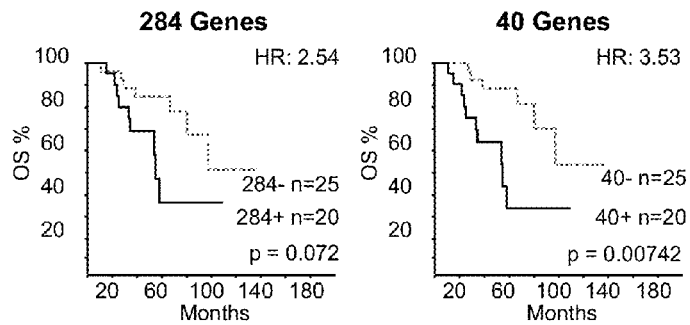

B GSE3143 Training Set

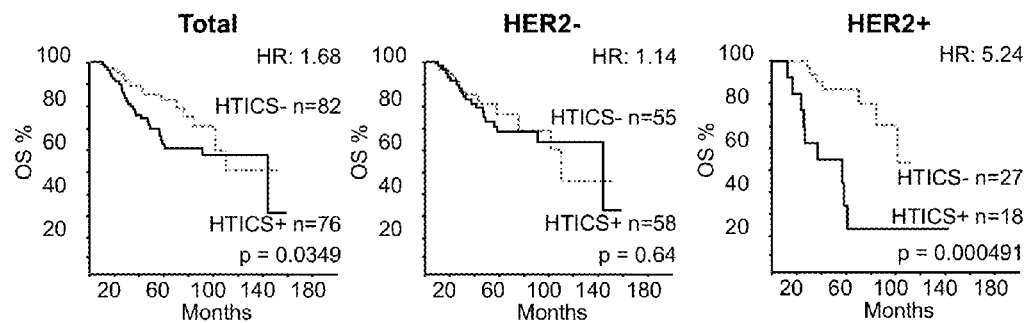

C

| | HTICS | Gene ID | Accession | Name | Pathways Involved |
|---|---|---|---|---|---|
| Up-Regulated in TIC | Aurkb | 9212 | NM_004217.1 | Aurora Kinase B | Cell Cycle |
| | Ccna2 | 890 | NM_001237.2 | Cyclin A2 | Cell Cycle |
| | Scrn1 | 9805 | NM_014766.2 | Secernin 1 | Cell Localization, Secretion |
| | Npy | 4852 | NM_000905.2 | Neuropeptide Y | Cell-cell signaling, Immune Response |
| | Atp7b | 540 | NM_000053.1 | ATPase, Cu++ transporting, beta polypeptide | ATP catabolic process, Homeostasis |
| | Chaf1b | 8208 | NM_005441.1 | Chromatin assembly factor 1, subunit B | DNA Repair |
| | Ccnb1 | 891 | NM_031966.2 | Cyclin B1 | Cell Cycle |
| | Cldn8 | 9073 | NM_199328.1 | Claudin 8 | Cell Junction, Cell Migration |
| Up-Regulated in CD24- | Nrp1 | 8829 | NM_003873.1 | Neuropilin 1 | Angiogenesis, Cell Migration |
| | Ccr2 | 729230 | NM_000647.3 | Chemokine (C-C motif) receptor 2 | Angiogenesis, Signaling, Immune Response |
| | C1qb | 713 | NM_000491.2 | Complement component 1, q subcomponent binding protein | Immune Response |
| | CD74 | 972 | NM_004355.1 | CD74 molecule | Signaling, T-Cell, Immune Response |
| | Vcam1 | 7412 | NM_001078.2 | Vascular cell adhesion molecule 1 | Cell Surface |
| | CD180 | 4064 | NM_005582.1 | CD180 molecule | Immune Response |
| | Itgb2 | 3689 | NM_000211.1 | Integrin, beta 2 | Angiogenesis, Cell Migration, Immune Response |
| | CD72 | 971 | NM_001782.1 | CD72 molecule | Sugar Binding |
| | St8sia4 | 7903 | NM_175052.1 | ST8 alpha-N-acetyl-neuraminide alpha-2,8-sialyltransferase 4 | Protein Glycosylation, Protein Modification |

Figure 11D-E
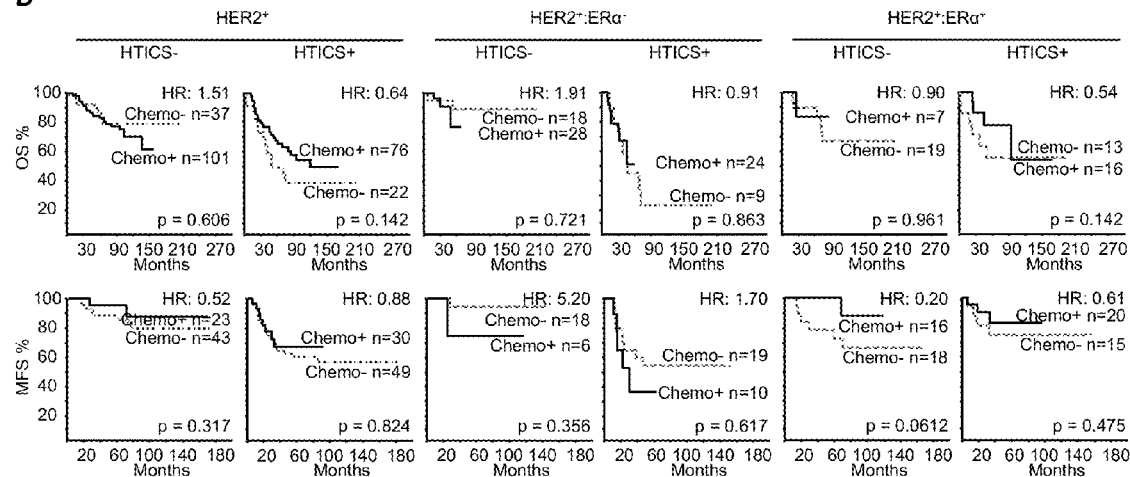
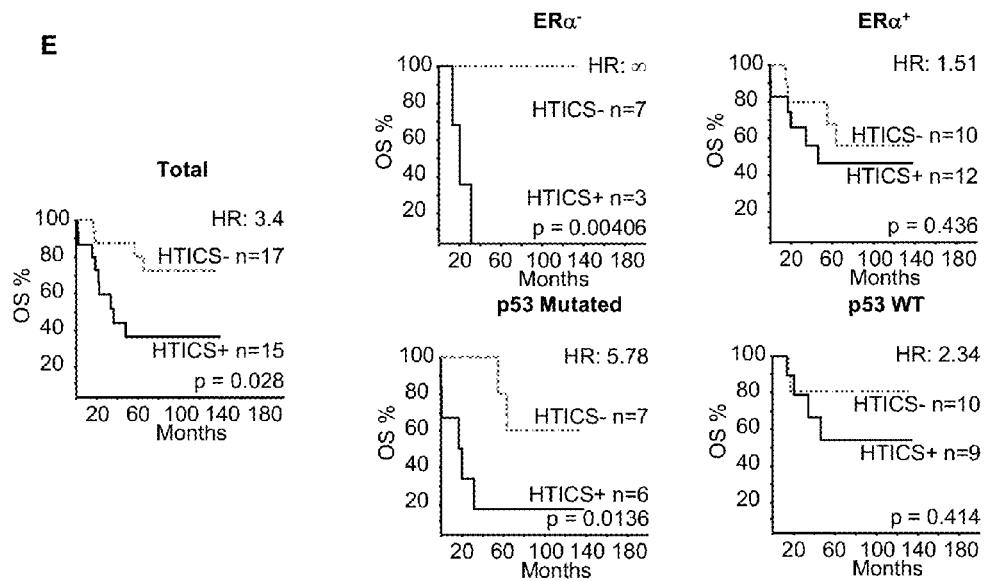

Figure 13

Bivariate Analysis of HTICS with each of the following variables for HER2+ patients (from 3 - 6 Test OS Cohorts)

| Variables | n+ | n- | Overall Survival p Value | Hazard Ratio (95% CI) |
|---|---|---|---|---|
| ERα (+/-) | 55 | 79 | 0.57 | 0.83 (0.43 – 1.59) |
| +HTICS | 62 | 72 | 0.0013 | 3.14 (1.56 – 6.32) |
| Chemo (+/-) | 177 | 59 | 0.798 | 0.94 (0.56 – 1.56) |
| +HTICS | 98 | 138 | 0.0004 | 2.32 (1.46 – 3.70) |
| Grade ≥ 3 | 100 | 47 | 0.728 | 1.12 (0.60 – 2.07) |
| +HTICS | 66 | 81 | 0.0056 | 2.36 (1.29 – 4.33) |
| Age ≥ 50 | 88 | 100 | 0.676 | 1.11 (0.68 – 1.82) |
| +HTICS | 78 | 110 | 0.0002 | 2.62 (1.59 – 4.33) |
| Node (+/-) | 62 | 69 | 0.0001 | 4.21 (2.01 – 8.85) |
| +HTICS | 61 | 70 | 0.0063 | 2.74 (1.33 – 5.65) |
| Size ≥ 2 cm | 75 | 27 | 0.462 | 1.35 (0.61 – 3.01) |
| +HTICS | 46 | 56 | 0.0054 | 2.75 (1.35 – 5.60) |
| Univariate Analysis of HTICS on Subgroups with Significantly Increased HR | | | | |
| | Node+ | | | |
| HTICS | 35 | 27 | 0.0238 | 3.12 (1.16 – 8.35) |

Bivariate Analysis of HTICS with each of the following variables for HER2+:ERα- patients (from 3 - 6 Test OS Cohorts)

| Variables | n+ | n- | Overall Survival p Value | Hazard Ratio (95% CI) |
|---|---|---|---|---|
| Chemo (+/-) | 52 | 27 | 0.886 | 1.08 (0.40 – 2.88) |
| +HTICS | 33 | 46 | 0.0012 | 5.52 (1.97 – 15.51) |
| Grade ≥ 3 | 63 | 15 | 0.268 | 0.59 (0.23 – 1.50) |
| +HTICS | 33 | 45 | 0.0016 | 5.26 (1.88 – 14.71) |
| Age ≥ 50 | 26 | 22 | 0.57 | 1.31 (0.51 – 3.35) |
| +HTICS | 18 | 30 | 0.0008 | 5.92 (2.08 – 16.81) |
| Node (+/-) | 40 | 37 | 0.0332 | 3.28 (1.10 – 9.79) |
| +HTICS | 33 | 44 | 0.0027 | 5.69 (1.83 – 17.74) |
| Size ≥ 2 cm | 36 | 11 | 0.889 | 1.08 (0.35 – 3.40) |
| +HTICS | 17 | 30 | 0.0014 | 5.66 (1.96 -16.34) |
| Univariate Analysis of HTICS on Subgroups with Significantly Increased HR | | | | |
| | Node+ | | | |
| HTICS | 21 | 19 | 0.0321 | 5.20 (1.15 – 23.5) |

Multivariate Analysis of HTICS with all variables for HER2+:ERα- patients (3 Test OS Cohorts)

| Variables | n+ | n- | Overall Survival p Value | Hazard Ratio (95% CI) |
|---|---|---|---|---|
| HTICS | 17 | 27 | 0.0051 | 6.27 (1.73 -22.67) |
| Chemo (+/-) | 18 | 26 | 0.8 | 1.20 (0.30 – 4.80) |
| Grade ≥ 3 | 32 | 12 | 0.4213 | 1.66 (0.48 – 5.66) |
| Age ≥ 50 | 24 | 20 | 0.2803 | 1.92 (0.59 -6.27) |
| Node (+/-) | 20 | 24 | 0.0147 | 8.29 (1.52 – 45.39) |
| Size ≥ 2 cm | 34 | 10 | 0.5294 | 0.60 (0.12 – 2.95) |

Figure 14
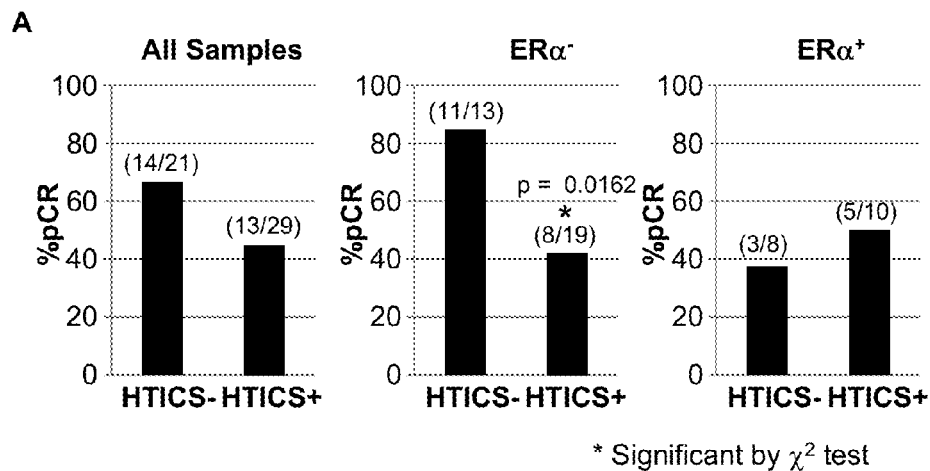
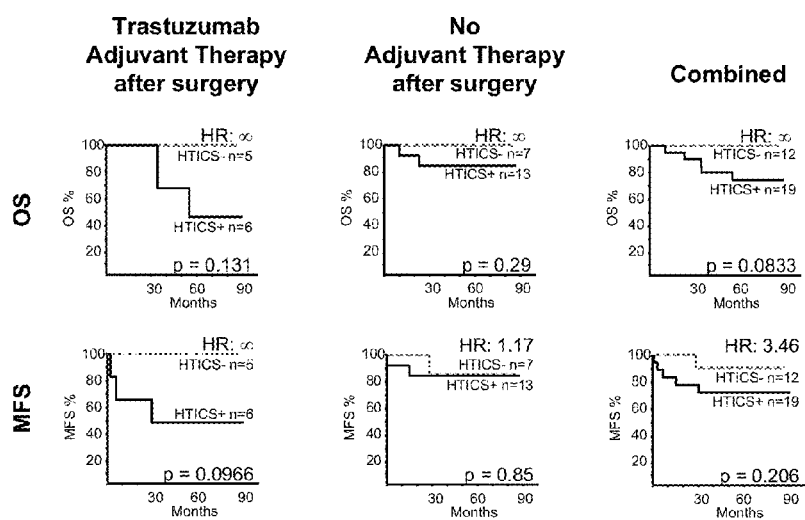

Figure 15

HER2⁺ Patients

| MFS (n = 145) | | | OS (n = 116) | | |
|---|---|---|---|---|---|
| Rank | HR: | p-value | Rank | HR: | p-value |
| 1 | 3.23938 | 0.000304 | 1 | 2.94323 | 0.002781 |
| 2 | 2.8496 | 0.001307 | 2 | 2.90099 | 0.007201 |
| 3 | 2.84942 | 0.00139 | 3 | 2.72497 | 0.008974 |
| 4 | 2.82337 | 0.001436 | 4 | 2.66395 | 0.007544 |
| 5 | 2.81115 | 0.001478 | 5 | 2.63798 | 0.007616 |
| 6 | 2.73136 | 0.002011 | 6 | 2.61337 | 0.007822 |
| 7 | 2.62493 | 0.002956 | 7 | 2.60984 | 0.008525 |
| 8 | 2.54016 | 0.004092 | 8 | 2.60787 | 0.008253 |
| 9 | 2.53351 | 0.005798 | 9 | 2.57817 | 0.013345 |
| 10 | 2.45527 | 0.006311 | 10 | 2.54933 | 0.012171 |
| 11 | 2.36872 | 0.008073 | 11 | 2.5026 | 0.012081 |
| 12 | 2.3477 | 0.00904 | 12 | 2.42139 | 0.019991 |
| 13 | 2.30651 | 0.010535 | 13 | 2.38716 | 0.018259 |
| 14 | 2.29881 | 0.011029 | 14 | 2.37529 | 0.018754 |
| 15 | 2.27588 | 0.012178 | 15 | 2.34536 | 0.0195 |
| 16 | 2.2222 | 0.014628 | 16 | 2.32968 | 0.02173 |
| 17 | 2.22042 | 0.014954 | 17 | 2.31672 | 0.020545 |
| 18 | 2.18346 | 0.019098 | 18 | 2.25326 | 0.025828 |

3.3% Random Signatures are Significant (p<0.05) & HR>2

2.1% Random Signatures are Significant (p<0.05) & HR>2

HER2⁺:ER⁻ Patients

| MFS (n = 53) | | |
|---|---|---|
| Rank | HR: | p-value |
| 1 | 5.16279 | 0.001595 |
| 2 | 5.14167 | 0.001145 |
| 3 | 4.17666 | 0.004504 |
| 4 | 4.15949 | 0.005372 |
| 5 | 3.7685 | 0.008626 |
| 6 | 3.76373 | 0.008591 |
| 7 | 3.73593 | 0.011563 |
| 8 | 3.68244 | 0.012952 |
| 9 | 3.6219 | 0.015392 |
| 10 | 3.57605 | 0.020853 |
| 11 | 3.52333 | 0.012912 |
| 12 | 3.42243 | 0.016796 |
| 13 | 3.34076 | 0.01823 |
| 14 | 3.22356 | 0.022498 |
| 15 | 3.18972 | 0.021504 |
| 16 | 3.1228 | 0.027506 |
| 17 | 3.10085 | 0.028816 |
| 18 | 3.08084 | 0.043902 |

2.8% Random Signatures are Significant (p<0.05) & HR>2

SIGNATURE FOR PREDICTING CLINICAL OUTCOME IN HUMAN HER2+ BREAST CANCER

CROSS REFERENCE TO RELATED APPLICATIONS

This application claims the benefit of 35 USC 119 based on the priority of U.S. Provisional Application No. 61/610,792 filed Mar. 14, 2012, which is herein incorporated by reference.

INCORPORATION OF SEQUENCE LISTING

A computer readable form of the Sequence Listing "P41422US01SequenceListing.txt" (4,107 bytes), submitted via EFS-WEB and created on Jun. 12, 2013, is herein incorporated by reference.

FIELD

The disclosure relates to methods and kits for prognosing outcome, predicting treatment response, diagnosing high grade breast cancer and selecting a treatment for a subject with breast cancer, optionally Her2+ breast cancer, and more specifically to methods and kits using a HTICS expression signature for prognosing outcome predicting treatment response, diagnosing high grade breast cancer and selecting a treatment for a subject with Her2+:ERα$^-$ breast cancer.

INTRODUCTION

Breast cancer (BC) represents multiple diseases, including HER2$^+$, ERα$^+$ (luminal A and B), and triple negative (Basal-like, Claudin-low) tumors. HER2$^+$ BC is caused by over-expression/amplification of the HER2/ERBB2/NEUtyrosine kinase receptor, and constitutes 15-20% of cases. About 50% of these are ERα$^+$ tumors and 50% are ERα$^-$. Current treatment of HER2$^+$ BC involves chemotherapy plus trastuzumab (Herceptin; Genentech, South San Francisco, Calif.), a monoclonal antibody directed against HER2 (1-3). Despite improvement in disease free survival (DFS) over a 4 year followup (4), the cost of trastuzumab, adverse effects such as cardiac failure and emergence of drug-resistance metastases represent serious limitations for its use, particularly in low-income countries (5). A prognostic signature that can predict clinical outcome from tumor biopsies at time of presentation may help prioritize patients for anti-HER2 therapy.

As BC consists of several different subtypes, each with distinct pathological features and clinical behaviors, predictive prognostic signatures may need to be developed for each subtype. In addition, many types of cancer exhibit hierarchical organization whereby only a fraction of cells, termed tumor-initiating cells (TICs), sustains growth, whereas the remaining tumor cells, which descend from TICs, have lost their tumorigenic potential (6). HER2/Neu drives asymmetrical cell division, increases the frequency of TICs relative to mammary stem cells (7), and its continuous expression is required to sustain tumorigenesis (8). One strategy to identify prognostic signatures would be to base it on gene expression in enriched TIC populations for specific BC subtype. However, so far, most prognostic signatures for BC were generated irrespective of TICs or BC subtype. As a result, these signatures are predictive for ERα$^+$ tumors, which represent 60-70% of human BC, but not for HER2$^+$:ERα$^-$ or triple negative BC (9). Thus, Oncotype, a 21 gene recurrence signature (10), is highly predictive for ERα$^+$ (HR, 4.79) but not other subtypes such as HER2$^+$ (HR, 1.0), the invasiveness gene signature (IGS) generated from CD44$^+$/CD24$^{-/low}$ breast TICs (11), scores on ERα$^+$ (HR, 2.12) but not HER2$^+$ patients (HR, 0.96)(10)(this study), and astroma-derived prognostic predictor (SDPP) (12) is shown herein to predict clinical outcome for HER2$^+$:ERα$^+$ but not for HER2$^+$:ERα$^-$ BC.

SUMMARY

An aspect includes a method of predicting outcome and/or anti-Her2 treatment response and/or diagnosing a high risk HER2+ ERα negative breast cancer in a subject afflicted with breast cancer comprising:

a. determining HTICs expression signature comprising determining an expression level of 2 or more HTICS biomarkers selected from Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72 and St8sia4 in a test sample from the subject; and b. comparing the expression level of the 2 or more biomarkers with a control;

c. identifying the subject as having an increased likelihood of poor outcome or a good outcome, and/or predicting a response or lack of response to an anti-Her2 treatment and/or diagnosing the subject with high risk HER2+ ERα negative breast cancer or low risk Her2+ ERα negative breast cancer according to a difference or a similarity in the expression level of the 2 or more biomarkers between the test sample and the control.

In an embodiment, an increase in the expression level of 2 or more HTICS markers selected from Aurkb, Ccna2, Scrn1, Npy, Atp7b, Chaf1b, Ccnb1 and/or Cldn8 and/or a decrease in the expression level of 2 or more HTICS markers selected from Nrp1, Ccr2, C1qb, Cd74, Vcam1, Cd180, Itgb2, Cd72 and/or St8sia4 identifies a subject with poor outcome and/or response to anti-Her2 treatment and/or diagnosing the subject with high risk HER2+ ERα negative breast cancer, or a decrease in the expression level of 2 or more HTICS markers selected from Aurkb, Ccna2, Scrn1, Npy, Atp7b, Chaf1b, Ccnb1 and/or Cldn8 and/or an increase in the expression level of 2 or more HTICS markers selected from Nrp1, Ccr2, C1qb, Cd74, Vcam1, Cd180, Itgb2, Cd72 and/or St8sia4 identifies a subject with a good outcome and/or lack of response to an anti-Her2 treatment and/or or low risk Her2+ ERα negative breast cancer.

In an embodiment, the method comprises prior to determining step a;

i. identifying a subject that is Her2+ and ERα-;
ii. obtaining a test sample from the subject.

In an embodiment, the method comprises a. determining a HTICs expression signature comprising determining an expression level of 2 or more HTICS biomarkers selected from Aurkb, Ccna2, Scrn1, Npy, Atp7b, Chaf1b, Ccnb1, Cldn8, Nrp1, Ccr2, C1qb, Cd74, Vcam1, Cd180, Itgb2, Cd72 and St8sia4 in a test sample from the subject;

b. calculating a signature score, optionally a signature score match (SSM), the signature score comprising a sum of HTICs biomarker expression level parameters; and c. identifying the subject as having an increased likelihood of a poor outcome and/or responsive to anti-Her2 treatment and/or diagnosing the subject with high risk HER2+ ERα negative breast cancer when the a signature score is greater than a selected cut-off or control signature score i and identifying the subject as having an increased likelihood of a good outcome and/or lack of response to an anti-Her2 treatment and/or or low risk Her2+ ERα negative breast cancer when the signature score is less than the selected cut-off or control signature score.

In another embodiment, the 2 or more HTICS biomarkers comprise 3, 4, 5, 6, 7, 8, 9, 10, 11, 12, 13, 14, 15, 16 or 17 biomarkers selected from HTICS biomarkers Aurkb, Ccna2, Scrn1, Npy, Atp7b, Chaf1b, Ccnb1, Cldn8, Nrp1, Ccr2, C1qb, Cd74, Vcam1, Cd180, Itgb2, Cd72 and St8sia4.

In an embodiment, the method further comprises assessing one or more biomarkers selected from Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86.

In an embodiment, an increase in the expression of two or more HTICS biomarkers selected from Aurkb, Ccna2, Scrn1, Npy, Atp7b, Chaf1b, Ccnb1, Cldn8, Kif11, Plk1, Chek1 and Mphosph6 predicts poor outcome and/or reponse to anti-Her2 treatment, and a decrease in the expression of two or more HTICS biomarkers selected from Aurkb, Ccna2, Scrn1, Npy, Atp7b, Chaf1b, Ccnb1, Cldn8, Kif11, Plk1, Chek1 and Mphosph6 predicts good outcome and/or lack of response to an anti-Her2 treatment.

In another embodiment, a decrease in the expression of 2 or more HTICS biomarkers selected from Nrp1, Ccr2, C1qb, Cd74, Vcam1, Cd180, Itgb2, Cd72, St8sia4, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86 predicts poor outcome or poor treatment response and/or response to anti-HER2 treatment and/or an increase in the expression of 2 or more HTICS biomarkers selected from Nrp1, Ccr2, C1qb, Cd74, Vcam1, Cd180, Itgb2, Cd72, St8sia4, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86 predicts good outcome and/or lack of response to anti-HER2 treatment.

In another embodiment, comparing the expression level of the 2 or more biomarkers with the control comprises calculating a signature score match (SSM) and comparing to a selected cut-off level,
wherein the signature score match is calculated according to: Score for Signature Match $(SSM)=\Sigma(I_n X_n/|X_n|)/\Sigma(|I_n|)$;
where I is the gene index for each biomarker (n)−1 is used for HITCS biomarkers which are up-regulated genes in TICs and −1 for down-regulated genes in TICs; X is the log 2 transformed and median-centered and/or normalized gene expression value for each HTICS biomarker (n) of the subject.

In another embodiment, a subject SSM greater than the cut-off level predicts poor outcome and/or response to anti-Her2 treatment or wherein a subject SSM less than the cut-off score predicts good outcome and/or lack of response to anti-Her2 treatment.

In an embodiment, the poor outcome is reduced overall survival, disease free survival and/or metastasis free survival and the good outcome is increased overall survival, disease free survival and/or metastasis free survival.

In another embodiment, the comparing the expression level of the 2 or more biomarkers in the test sample with a control comprises determining the relative expression of each biomarker, calculating a SSM for the subject, and using the SSM to classify the subject as having a poor outcome or a good outcome by comparing the SSM to a control, wherein the control is a selected cut-off level corresponding to 0.

In an embodiment, the expression level determined is a nucleic acid expression level.

In another embodiment, the biomarker expression level is determined using quantitative PCR, optionally quantitative RT-PCR, serial analysis of gene expression (SAGE), microarray, digital molecular barcoding technology, such as Nanostring analysis or Northern Blot or other probe based or amplification based assay.

In yet another embodiment the expression level determined is a polypeptide level and the biomarker expression level is determined using an antibody based method wherein the antibody specifically binds to the polypeptide and immunoassaying the polypeptide-antibody complex level, optionally by immunohistochemistry or ELISA.

In an embodiment, the cancer is Her2+, ERα− and/or node positive.

A further aspect includes a method of treating a breast cancer subject in need thereof comprising:
a) obtaining a test sample from the subject;
b) predicting the outcome and/or treatment response according to the method of described herein; and
c) administering to the subject a treatment suitable according to the predicted outcome
wherein the treatment comprises adjuvant anti-Her2 treatment, optionally trastuzumab, pertuzumab, or lapatinib treatment, when the subject is predicted to have a poor outcome (e.g. HTICS+) and the treatment lacks adjuvant anti-Her2 treatment, when the subject is predicted to have a good outcome (HTICS−).

Another aspect includes an array comprising, for each of a plurality of HTICS biomarkers selected from Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72, St8sia4 Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86, one or more polynucleotide probes complementary and hybridizable to an expression product of the HTICS biomarker and/or one or more antibodies specific to a polypeptide expression product of the HTICS biomarker.

Yet another aspect includes a kit comprising at least two biomarker specific agents, each of which detects or can be used to determine the expression level of a HTICS biomarker selected from Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72, St8sia4 Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86, a container and optionally a kit control.

In an embodiment, the kit comprises one or more of:
a) an array for detecting the expression of one or more HTICs biomarkers,
b) a probe that is specific for the biomarker optionally listed in Table 3,
c) primer set that amplifies a nucleic acid transcript of to HTICs biomarker and optionally
d) a kit control;
e) reagents for qRT-PCR
f) reagents for molecular barcoding technology; and
g) instructions for use.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the disclosure will now be described in relation to the drawings in which:

FIG. 11. Generation and predictive power of HTICS. (A) Stepwise generation of HTICS and specificity for HER2$^+$ patients. Kaplan-Meier OS curves for the 284 and 40 gene (FIG. 11 & Table 2) signatures derived from differentially expressed genes in TICs versus non-TICs in the GSE3143 training cohort. HTICS was derived from the 40 gene signature (FIG. 4A). (B) HTICS predicts outcome for HER2$^+$ patients (HR=5.24; P=0.00049) but not for all BC or HER2$^-$ patients. (C) List of HTICS genes, names and functions. (D) Retrospective analysis showing that HER2$^+$:ERα$^-$ BC patients exhibit poor response to conventional chemotherapy. Kaplan-Meier curves of HER2$^+$, HER2$^+$:ERα$^-$ and HER2$^+$:ERα$^+$ BC patients subdivided by HTICS+/− status was used to determine the efficacy of systemic chemotherapy with all 6 OS and 6 MFS test cohorts. A tendency of HER2$^+$ and HER2$^+$:ERα$^+$, but not HER2$^+$:ERα$^-$ patients, to benefit from chemotherapy was observed for both the OS and MFS analysis. (E) p53 status affects HTICS prognostic power. OS survival for HER2$^+$ tumors in the GSE3494 set, which provides p53 and ERα status, for all patients (left), or patients divided on the basis of ERα expression (top) or p53 mutant versus wild-type (bottom).

FIG. 13. HTICS predicts OS independently of other predictors including Node status. The status of ER (+/−), administration of systemic chemotherapy (excluding trastuzumab) (chemo+/−, Table 1A), grade ($\geq 3$), age ($\geq 50$ years), lymph node (+/−), and size (2 cm) were taken into consideration with HTICS in bi- and multivariate analysis using Cox Proportional Hazard Model, Three OS test cohorts (GSE3494, GSE7390 & GSE18229) had information on all variables and were used for multivariate analysis. In addition, the status of ERα was also available with GSE16446; administration of systemic chemotherapy included in GSE1456, GSE16446 and GSE20685; grade included in GSE1456 and GSE16446; age included in GSE20685; and node status also in GSE16446. The bivariate analysis for HER2$^+$ and HER2$^+$:ERα$^-$ patients was performed with all available data from the 6 cohorts. Additional univariate analysis was performed on the node+ subgroup showing that HTICS can further subdivide these patients into high and low risk groups with HR of 5.2. The multivariate analysis demonstrates that HTICS predicts clinical outcome independently of all other predictors, and can be combined with node status to increase HR.

FIG. 14. Analysis of MD Anderson dataset for HER2$^+$ patients treated with neoadjuvant chemotherapy plus trastuzumab. (A) % pathological complete response (pCR) determined at the time of surgery. Patients were subdivided into two groups according to ERα status (determined by IHC). For ERα$^-$ patients, the HTICS$^+$ group has significant lower % pCR than the HTICS$^-$ group (P=0.0162, chi-square test). FIG. 6A shows data on pCR after combining this MD Anderson dataset with a publicly available cohort (GSE22358; see text) (B) OS and MFS analysis for HER2$^+$:ERα$^-$ patients 90 months post-surgery. Patients were grouped according to the continuation (left) or not (center) of trastuzumab treatment after surgery. In both cases, no death occurred in the HTICS$^-$ group compared with 5 deaths in the HTICS$^+$ group (P=0.0833) for the combined data. Only one patient in the HTICS$^-$ group had metastasis versus 5 patients with metastases in the HTICS$^+$ set (P=0.206).

FIG. 15. Prognostic Power of HTICS Signature Compared with 1000 Random Signatures in HER2+ Breast Cancer Patients.

DETAILED DESCRIPTION

I. Definitions

Figure 1:
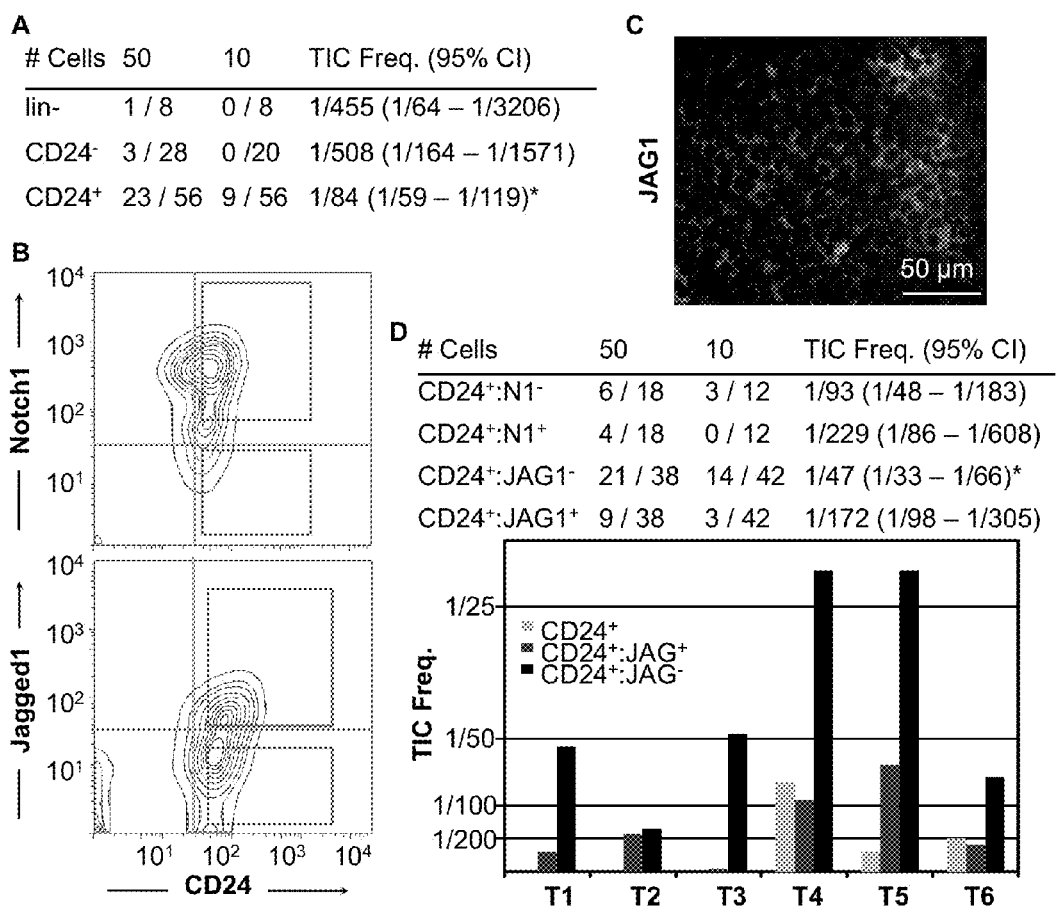
FIG. 1. Identification of Her2/neu TICs as $CD24^+$, $JAG1^-$. (A) TIC frequency in $CD24^+$, $CD24^-$ and lineage depleted ($lin^-$) Her2/Neu tumor cells purified by mechanical dissociation and cell sorting. (B) Representative flow cytometry profiles of $lin^-Pl^-$ Her2/Neu tumor cells for CD24-Notch1 and CD24-Jagged1, and gating conditions used to sort cells for transplantation. (C) Immunofluorescent staining for Jagged1 in an MMTV-Neu tumor. DAPI was used to label nuclei. (D) Top, average TIC frequency and 95% confidence intervals (CI) following serial dilution transplantations of indicated fractions from 6 independent MMTV-Neu primary tumors. *denotes P=0.0005 against $CD24^+$ (ANOVA). Bottom, average TIC frequency for $CD24^+$:$JAG1^+$ and $CD24^+$:$JAG1^-$ populations for 6 individual tumors. The $CD24^+$ fraction was also analyzed in tumors 4-6.

The term "antibody" as used herein is intended to include monoclonal antibodies, polyclonal antibodies, and chimeric antibodies. The antibody may be from recombinant sources and/or produced in transgenic animals.

The term "antibody binding fragment" as used herein is intended to include Fab, Fab', F(ab')2, scFv, dsFv, ds-scFv, dimers, minibodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

Antibodies may be monospecific, bispecific, trispecific or of greater multispecificity. Multispecific antibodies may immunospecifically bind to different epitopes of a polypeptide and/or a solid support material. Antibodies may be from any animal origin including birds and mammals (e.g., human, murine, donkey, sheep, rabbit, goat, guinea pig, camel, horse, or chicken).

Antibodies may be prepared using methods known to those skilled in the art. Isolated native or recombinant polypeptides may be utilized to prepare antibodies. See, for example, Kohler et al. (1975) Nature 256:495-497; Kozbor et al. (1985) J. Immunol Methods 81:31-42; Cote et al. (1983) ProcNatlAcadSci 80:2026-2030; and Cole et al. (1984) Mol Cell Biol 62:109-120 for the preparation of monoclonal antibodies; Huse et al. (1989) Science 246: 1275-1281 for the preparation of monoclonal Fab fragments; and, Pound (1998) Immunochemical Protocols, Humana Press, Totowa, N.J. for the preparation of phagemid or B-lymphocyte immunoglobulin libraries to identify antibodies.

In aspects, the antibody is a purified or isolated antibody. By "purified" or "isolated" is meant that a given antibody or fragment thereof, whether one that has been removed from nature (isolated from blood serum) or synthesized (produced by recombinant means), has been increased in purity, wherein "purity" is a relative term, not "absolute purity." In particular aspects, a purified antibody is 60% free, preferably at least 75% free, and more preferably at least 90% free from other components with which it is naturally associated or associated following synthesis.

The term "biomarker of the disclosure" or "HTIC signature biomarker" as used herein refers to a biomarker disclosed herein to be increased and/or decreased in tumour initiating cells compared to non tumour initiating cells and predictive of outcome including overall survival (OS), disease frees survival (DFS) and metastasis free survival (MFS) in a subject with Her2+ breast cancer and includes for example, Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72, St8sia4 Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and/or Ly86. Further details of HTICS biomarkers such as full name, accession number and GeneID are provided in FIG. 11 and Table 2. The HTIC signature biomarkers are predictive of outcome and response to treatment. For example, it is demonstrated herein that increased expression of Aurkb, Ccna2, Scrn1, Npy, Atp7b, Chaf1b, Ccnb1 and Cldn8 and decreased expression of Nrp1, Ccr2, C1qb, Cd74, Vcam1, Cd180, Itgb2, Cd72 and St8sia4 (e.g. the 17 gene HTIC signature) and/or increased expression of Aurkb, Ccna2, Scrn1, Npy, Atp7b, Chaf1b, Ccnb1, Cldn8, Kif11, Plk1, Chek1 and Mphosph6, and decreased expression of Nrp1, Ccr2, C1qb, Cd74, Vcam1, Cd180, Itgb2, Cd72, St8sia4 Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86 (e.g. the 40 gene HTIC signature), is indicative of poor prognosis and/or poor treatment response to chemotherapy as described below. Subjects for example with a positive score calculated as described herein also demonstrate beneficial response to adjuvant anti-Her therapy, trastuzumab treatment. Conversely, subjects for example with a negative score calculated as described herein exhibit good prognosis and good treatment outcome with traditional chemotherapy and little or no added benefit with adjuvant trastuzumab treatment.

The phrase "biomarker polypeptide", "polypeptide biomarker" or "polypeptide product of a biomarker" refers to a proteinaceous biomarker gene product which levels of are associated with outcome and treatment response in Her2+ breast cancer.

The phrase "biomarker nucleic acid", or "nucleic acid product of a biomarker" refers to a polynucleotide biomarker gene product e.g. prognostic transcripts which levels of are associated with outcome and treatment response in Her2+ breast cancer.

The term "biomarker specific reagent" as used herein refers to a reagent that is a highly sensitive and specific for quantifying levels of a biomarker expression product, for example a polypeptide biomarker level or a nucleic acid biomarker product and can include antibodies which can for example be used with immunohistochemistry (IHC), ELISA and protein microarray (e.g. antibody array) or polynucleotides such as primers and probes which can for example be used with quantitative RT-PCR techniques, to detect the expression level of a biomarker associated with outcome and treatment response in Her2+ breast cancer.

The term "classifying" as used herein refers to assigning, to a class or kind, an unclassified item. A "class" or "group" then being a grouping of items, based on one or more characteristics, attributes, properties, qualities, effects, parameters, etc., which they have in common, for the purpose of classifying them according to an established system or scheme. For example, subjects having a HTIC signature score based on the expression level of two or more biomarkers selected for example from the 17 HTICs biomarkers Aurkb, Ccna2, Scrn1, Npy, Atp7b, Chaf1b, Ccnb1, Cldn8, Nrp1, Ccr2, C1qb, Cd74, Vcam1, Cd180, Itgb2, Cd72 and St8sia4 above a selected cutoff as described herein fall within in a class having poor outcome, poor response to traditional chemotherapy and good response to adjuvant trastuzumab chemotherapy. Similarly subjects having a HTIC signature score based on the expression level of two or more biomarkers selected for example from the 17 HTICs biomarkers Aurkb, Ccna2, Scrn1, Npy, Atp7b, Chaf1b, Ccnb1, Cldn8, Nrp1, Ccr2, C1qb, Cd74, Vcam1, Cd180, Itgb2, Cd72 and St8sia4 below a selected cutoff as described herein fall within in a class having good outcome, good response to traditional chemotherapy and lack of significant benefit from adjuvant trastuzumab chemotherapy.

The term "Aurkb" as used herein means Aurora Kinase B and includes without limitation all known Aurkb molecules, preferably human Aurkb including for example those deposited in Genbank with accession number NM_004217.1. The sequences disclosed in said accession numbers are herein incorporated by reference.

The term "Ccna2" as used herein means Cyclin A2 and includes without limitation all known Ccna2 molecules, preferably human Ccna2 including for example those deposited in Genbank with accession number NM_001237.2. The sequences disclosed in said accession numbers are herein incorporated by reference.

The term "Scrn1" as used herein means Secernin 1 and includes without limitation all known Scrn1 molecules, preferably human Scrn1 including for example those deposited in Genbank with accession number NM_014766.2. The sequences disclosed in said accession numbers are herein incorporated by reference.

The term "Npy" as used herein means Neuropeptide Y and includes without limitation all known Npy molecules, preferably human Npy including for example those deposited in Genbank with accession number NM_000905.2. The sequences disclosed in said accession numbers are herein incorporated by reference.

The term "Atp7b" as used herein means ATPase, Cu++ transporting, beta polypeptide and includes without limitation all known Atp7b molecules, preferably human Atp7b including for example those deposited in Genbank with accession number NM_000053.1. The sequences disclosed in said accession numbers are herein incorporated by reference.

The term "Chaf1b" as used herein means Chromatin assembly factor 1, subunit B and includes without limitation all known Chaf1b molecules, preferably human Chaf1b including for example those deposited in Genbank with accession number NM_005441.1. The sequences disclosed in said accession numbers are herein incorporated by reference.

The term "Ccnb1" as used herein means Cyclin B1 and includes without limitation all known Ccnb1 molecules, preferably human Ccnb1 including for example those deposited in Genbank with accession number NM_031966.2. The sequences disclosed in said accession numbers are herein incorporated by reference.

The term "Cldn8" as used herein means Claudin 8 and includes without limitation all known Cldn8 molecules, preferably human Cldn8 including for example those deposited in Genbank with accession number NM_199328.1. The sequences disclosed in said accession numbers are herein incorporated by reference.

The term "Nrp1" as used herein means Neuropilin 1 and includes without limitation all known Nrp1 molecules, preferably human Nrp1 including for example those deposited in Genbank with accession number NM_003873.1. The sequences disclosed in said accession numbers are herein incorporated by reference.

The term "Ccr2" as used herein means Chemokine (C—C motif) receptor 2 and includes without limitation all known Ccr2 molecules, preferably human Ccr2 including for example those deposited in Genbank with accession number NM_000647.3. The sequences disclosed in said accession numbers are herein incorporated by reference.

The term "C1qb" as used herein means Complement component 1, q subcomponent binding protein and includes without limitation all known C1qb molecules, preferably human C1qb including for example those deposited in Genbank with accession number NM_000491.2. The sequences disclosed in said accession numbers are herein incorporated by reference.

The term "Cd74" as used herein means Cd74 molecule and includes without limitation all known Cd74 molecules, preferably human Cd74 including for example those deposited in Genbank with accession number NM_004355.1. The sequences disclosed in said accession numbers are herein incorporated by reference.

The term "Vcam1" as used herein means Vascular cell adhesion molecule 1 and includes without limitation all known Vcam1 molecules, preferably human Vcam1 including for example those deposited in Genbank with accession number NM_001078.2. The sequences disclosed in said accession numbers are herein incorporated by reference.

The term "Cd180" as used herein means CD180 molecule and includes without limitation all known Cd180 molecules, preferably human Cd180 including for example those deposited in Genbank with accession number NM_005582.1. The sequences disclosed in said accession numbers are herein incorporated by reference.

The term "Itgb2" as used herein means Integrin, beta 2 and includes without limitation all known Itgb2 molecules, preferably human Itgb2 including for example those deposited in Genbank with accession number 000211.1. The sequences disclosed in said accession numbers are herein incorporated by reference.

The term "Cd72" as used herein means CD72 molecule and includes without limitation all known Cd72 molecules, preferably human Cd72 including for example those deposited in Genbank with accession number NM_001782.1. The sequences disclosed in said accession numbers are herein incorporated by reference.

The term "St8sia4" as used herein means ST8 alpha-N-acetyl-neuraminide alpha-2,8-sialyltransferase 4 and includes without limitation all known St8sia4 molecules, preferably human St8sia4 including for example those deposited in Genbank with accession number NM_175052.1. The sequences disclosed in said accession numbers are herein incorporated by reference.

Additional HTICS biomarkers are described in Table 2.

The term "control" as used herein refers to a sample or samples of Her2 ERα⁻ breast cancer tissue with known outcome for determining control HTIC signature biomarker expression levels; and/or a predetermined expression level or ratio for each of two or more HTIC signature biomarker levels and/or a predetermined cut-off level. The control can for example be a reference profile to which test sample expression levels are compared, and/or a predetermined level or levels expressed for example as a numerical value and/or range (e.g. control range) corresponding to the HTIC signature biomarker levels in such sample or samples. For example, as demonstrated herein, control samples with a known outcome can be used to determine a cut-off above which subjects are predicted to have an outcome (e.g. poor outcome) and below which subjects are predicted to have a different outcome (e.g. good outcome). Test samples are then compared to the predetermined value determined using control samples. The control can be an average, median, or calculated cut-off value (e.g. threshold) for each of 2 or more HTIC signature biomarkers and/or a composite thereof (e.g. sum) above or below which value a subject can be classified with an outcome class—e.g. good outcome or poor outcome. In embodiments calculating a SSM for example, the control is a selected value above which corresponds with an outcome and below which corresponds with another outcome. In certain methods, for example wherein the method of determining expression involves a Nanostring type assay, a relative or normalized expression is determined to one or more internal normalization genes (e.g. internal to the test sample) which are known and/or are determined to be suitable e.g. not vary significantly due to BC and/or from patient to patient. Control samples can be used to establish a fold increase relative to the normalization gene or genes. Accordingly, the control can be, for each biomarker, a ratio of the biomarker gene expression level and the level of one or more internal standardization markers in a control sample. The control ratio is compared to a corresponding ratio determined for the sample. For example, if the ratio of the biomarker gene and internal standardization marker in a control sample is 1, a ratio of 1.5, 2, 2.5 or more is indicative of increased expression and a ratio of 0.8, 0.5, 0.3 or less is indicative of decreased expression. The ratios can also be used to determine a cut off or threshold level or used in a SSM calculation. In such cases the control is a selected value above which is determined to predict one outcome and below which is determined to predict a different outcome.

The cut-off, threshold or control signature score can for example be a median level or value, or composite signature score comprising the median expression level or levels, for example the weighted expression levels, in a population of subjects. Following a larger clinical study, a cut-off or threshold can be determined to optimize the trade-off between false negative and false positive discoveries, for example by optimizing the area under the ROC curve. It may also be desirable to define multiple thresholds, for example to assign patients to high, medium, and low risk groups. The threshold(s) may be at any percentile of risk scores in the study sample, for example corresponding to the lowest 90%, 80%, 70%, 60%, 50%, 40%, 30%, 20% or 10% of risk scores calculated form histologically normal margins in a population of subjects. A person skilled in the art would understand that "control" as herein defined is distinct from for example a PCR control, no template PCR control or internal control, which is used for example with quantitative PCR. For example an internal control is a non-biomarker gene that is expected to be expressed at relatively the same level in different samples that is used to quantify the relative amount of biomarker transcript for comparison purposes.

The term "determining an expression level" or "determining an expression profile" as used in reference to a biomarker means the application of a biomarker specific reagent such as a probe, primer or antibody and/or a method to a sample, for example a sample of the subject and/or a control sample, for ascertaining or measuring quantitatively, semi-quantitatively or qualitatively the amount of a biomarker or biomarkers, for example the amount of biomarker polypeptide or mRNA. For example, a level of a biomarker can be determined by a number of methods including for example immunoassays including for example immunohistochemistry, ELISA, Western blot, immunoprecipitation and the like, where a biomarker detection agent such as an antibody for example, a labeled antibody, specifically binds the biomarker and permits for example relative or absolute ascertaining of the amount of polypeptide biomarker, hybridization and PCR protocols where a probe or primer or primer set are used to ascertain the amount of nucleic acid biomarker, including for example probe based and amplification based methods including for example microarray analysis, RT-PCR such as quantitative RT-PCR, serial analysis of gene expression (SAGE), Northern Blot, digital molecular barcoding technology, for example Nanostring: nCounter™ Analysis, and TaqMan quantitative PCR assays. Other methods of mRNA detection and quantification can be applied, such as mRNA in situ hybridization in formalin-fixed, paraffin-embedded (FFPE) tissue samples or cells. This technology is currently offered by the QuantiGene®ViewRNA (Affymetrix), which uses probe sets for each mRNA that bind specifically to an amplification system to amplify the hybridization signals; these amplified signals can be visualized using a standard fluorescence microscope or imaging system. This system for example can detect and measure transcript levels in heterogeneous samples; for example, if a sample has normal and tumor cells present in the same tissue section. As mentioned, TaqMan probe-based gene expression analysis (PCR-based) can also be used for measuring gene expression levels in tissue samples, and for example for measuring mRNA levels in FFPE samples. In brief, TaqMan probe-based assays utilize a probe that hybridizes specifically to the mRNA target. This probe contains a quencher dye and a reporter dye (fluorescent molecule) attached to each end, and fluorescence is emitted only when specific hybridization to the mRNA target occurs. During the amplification step, the exonuclease activity of the polymerase enzyme causes the quencher and the reporter dyes to be detached from the probe, and fluorescence emission can occur. This fluorescence emission is recorded and signals are measured by a detection system; these signal intensities are used to calculate the abundance of a given transcript (gene expression) in a sample.

The term "difference in the level" as used herein in comparison to a control refers to a measurable difference in the level or quantity of a biomarker or biomarkers associated in a test sample, compared to the control that is of sufficient magnitude to allow assessment of predicted outcome, for example a significant difference or a statistically significant difference. The magnitude of the difference is sufficient for example to determine that the subject falls within a class of subjects likely to have poor prognosis or good prognosis, poor treatment response or good treatment response and/or to benefit from adjuvant treatment. For example, a difference in a level of biomarker level is detected if a ratio of the level in a test sample as compared with a control is greater than 1.5 for example, a ratio of greater than 1.7, 2, 3, 3, 5, 10, 12, 15, or more and/or a ratio less than 0.7, for example a ratio less than 0.6, 0.5, 0.4, 0.2, 0.1, 0.05 or more.

The term "digital molecular barcoding technology" as used herein refers to a digital technology that is based on direct multiplexed measurement of gene expression that utilizes color-coded molecular barcodes, and can include for example NanostringnCounter™. For example, in such a method each color-coded barcode is attached to a target-specific probe, for example about 50 bases to about 100 bases or any number between 50 and 100 in length that hybridizes to a gene of interest. Two probes are used to hybridize to mRNA transcripts of interest: a reporter probe that carries the color signal and a capture probe that allows the probe-target complex to be immobilized for data collection. Once the probes are hybridized, excess probes are removed and detected. For example, probe-target complexes can be immobilized on a substrate for data collection, for example an nCounter™Cartridge and analysed for example in a Digital Analyzer such that for example color codes are counted and tabulated for each target molecule.

The term "ERα negative" as used herein means cells with low levels and/or an absence of ERα expression, which can be determined for example by IHC, wherein samples with less than about 15% considered ERα-negative, less than about 15% or less than 10% of cells in a sample staining positive for ERα expression.

The term "expression level" as used herein in reference to a biomarker refers to a quantity of biomarker that is detectable or measurable in a sample and/or control. The quantity is for example a quantity of polypeptide, or a quantity of nucleic acid e.g. biomarker transcript. Accordingly, a polypeptide expression level refers to a quantity of biomarker polypeptide that is detectable or measurable in a sample and a nucleic acid expression level refers to a quantity of biomarker nucleic acid that is detectable or measurable in a sample. The expression level can be an absolute expression level, a normalized expression and/or a relative expression level.

The term "expression profile" as used herein refers to, for one or a plurality (e.g. at least two) of biomarkers that are associated with Her2+ breast cancer outcome, biomarker steady state and/or transcript or polypeptide expression levels in a sample from a subject. For example, an expression profile can comprise the quantitated relative levels of at least 2 or more biomarkers selected from for example Aurkb, Ccna2, Scrn1, Npy, Atp7b, Chaf1b, Ccnb1, Cldn8, Nrp1, Ccr2, C1qb, Cd74, Vcam1, Cd180, Itgb2, Cd72 and St8sia4 and the levels or pattern of biomarker expression can be compared to one or more reference profiles, for example a reference profile associated with poor outcome and/or a reference profile associated with good outcome.

The term "Her2+ breast cancer" as used herein refers to a breast cancer with increased Her2+ expression as determined by immunohistochemical staining and/or increase of Her2+ regulated genes (e.g. increased expression of 3 or more of ErbB2, Stard3, Perld1, Grb7 and C17orf37), wherein the increase is at least 2 fold above the median.

The term "HTICS" or HER2 TIC-enriched signature" as used herein means the expression level of 2 or more, for example 3, 4, 5, 6, 7, 8, 9, 10, 11, 12, 13, 14, 15, 16 or 17 HTICS biomarkers selected from Aurkb, Ccna2, Scrn1, Npy, Atp7b, Chaf1b, Ccnb1, Cldn8, Nrp1, Ccr2, C1qb, Cd74, Vcam1, Cd180, Itgb2, Cd72 St8sia4, Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86 in a test sample from the subject, including for example a median expression level associated. A subject identified as having the signature (i.e. HTICS+) is predicted to have poor outcome, poor chemotherapy treatment response and beneficial adjuvant response. For example, it is demonstrated herein that subjects with increased expression levels of Aurkb, Ccna2, Scrn1, Npy, Atp7b, Chaf1b, Ccnb1 and Cldn8 and decreased expression levels of Nrp1, Ccr2, C1qb, Cd74, Vcam1, Cd180, Itgb2, Cd72 and St8sia4 have poor outcome compared to patients who do not have the HTICS signature (i.e. HTICS−). It is also demonstrated that increased expression of Aurkb, Ccna2, Scrn1, Npy, Atp7b, Chaf1b, Ccnb1, Cldn8 and Kif11, Plk1, Chek1 and Mphosph6, and decreased expression of Nrp1, Ccr2, C1qb, Cd74, Vcam1, Cd180, Itgb2, Cd72, St8sia4 Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86, is indicative of poor prognosis and/or poor treatment response to chemotherapy. Accordingly, having a HTIC signature (i.e. HTICS+) comprises increased expression levels of Aurkb, Ccna2, Scrn1, Npy, Atp7b, Chaf1b, Ccnb1 and/or Cldn8 and/or decreased expression levels of Nrp1, Ccr2, C1qb, Cd74, Vcam1, Cd180, Itgb2, Cd72 and/or St8sia4. The expression levels can be used for example to calculate a HTIC signature score. For example, as described below, a subject with a Signature Score Match (SSM) of >50% wherein greater than 50% of the biomarkers are modulated in the same way as in TICs or a SSM calculated according to the formula below wherein the SSM is >0, expresses the HTICS signature (i.e. HTICS+) and is predicted to have a poor outcome.

Similarly it is demonstrated herein that not having a HTIC signature (i.e. HTICS−) which comprises having a decreased expression level of Aurkb, Ccna2, Scrn1, Npy, Atp7b, Chaf1b, Ccbn1 and Cldn8 and increased expression levels of Nrp1, Ccr2, C1qb, Cd74, Vcam1, Cd180, Itgb2, Cd72 and St8sia4, predicts a good outcome compared to patients who have the HTICS signature (i.e. HTICS+) It is also demonstrated that decreased expression of Aurkb, Ccna2, Scrn1, Npy, Atp7b, Chaf1b, Ccnb1, Cldn8 and Kif11, Plk1, Chek1 and Mphosph6, and increased expression of Nrp1, Ccr2, C1qb, Cd74, Vcam1, Cd180, Itgb2, Cd72, St8sia4 Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86, is indicative of good prognosis and/or good treatment response to chemotherapy compared to HTICS+ subjects. It is further demonstrated that HER2+ ER− subjects predicted to have a good prognosis do not significantly benefit from anti HER2 therapies such as trastuzumab. A subject is predicted to be HTICS-negative for example if the subject has a SSM <50% wherein less than 50% of the biomarkers are modulated in the same way as in TICs or has a SSM calculated according to the formula below wherein the SSM is <0.

The term "HTIC signature score" also referred to as "score for signature match" as used herein means for two or more HTIC signature biomarkers, a sum of the HTIC signature biomarker expression levels. For example, the HTIC signature score can be calculated according to the following formula:

$$\text{Score for Signature Match (SSM)} = \Sigma(I_n X_n/|X_n|)/\Sigma(|I_n|)$$

Where I is the gene index for each biomarker (n)−1 is used for HITCS biomarkers which are up-regulated genes in TICs and −1 for down-regulated genes in TICs. X is the log 2 transformed and median-centered gene expression value for each biomarker (n) of the patient. SSM≥0 was considered to be a match to the signature. The SSM can also for example be calculated as a percent match wherein if greater than 50% of the biomarkers are up/down regulated in the same way as in TICs, the sample is considered to be a match. A person skilled in the art would understand that other methods can be used to determine based on the expression levels of the HTICS biomarkers, if a subject falls into a high risk or low risk class and has a poor or good outcome including for example correlation methods such as Pearson's correlation.

The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. For example, hybridization in 6.0× sodium chloride/sodium citrate (SSC) at about 45° C., followed by a wash of 2.0×SSC at 50° C. may be employed.

The term "primer" as used herein refers to a polynucleotide, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less. The factors involved in determining the appropriate length of primer are readily known to one of ordinary skill in the art.

The term "polynucleotide", "nucleic acid" and/or "oligonucleotide" as used herein refers to a sequence of nucleotide or nucleoside monomers consisting of naturally occurring bases, sugars, and intersugar (backbone) linkages, and is intended to include DNA and RNA which can be either double stranded or single stranded, represent the sense or antisense strand.

The term "probe" as used herein refers to a nucleic acid sequence that will hybridize to a nucleic acid target sequence. In one example, the probe hybridizes to a biomarker RNA or a nucleic acid sequence complementary to the biomarker RNA. The length of probe depends for example, on the hybridization conditions and the sequences of the probe and nucleic acid target sequence. The probe can be for example, at least 15, 20, 25, 50, 75, 100, 150, 200, 250, 400, 500 or more nucleotides in length.

A person skilled in the art would recognize that "all or part of" of a particular probe or primer can be used as long as the portion is sufficient for example in the case a probe, to specifically hybridize to the intended target and in the case of a primer, sufficient to prime amplification of the intended template.

The term "reference expression profile" as used herein refers to a suitable comparison profile, for example a polypeptide or nucleic acid reference profile that comprises the expression levels of 2 or more HTIC signature biomarkers selected from from Aurkb, Ccna2, Scrn1, Npy, Atp7b, Chaf1b, Ccnb1, Cldn8, Nrp1, Ccr2, C1qb, Cd74, Vcam1, Cd180, Itgb2, Cd72 St8sia4, Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86, with known outcome. For example, it is demonstrated herein that subjects with increased expression levels of Aurkb, Ccna2, Scrn1, Npy, Atp7b, Chaf1b, Ccnb1 and Cldn8 and decreased expression levels of Nrp1, Ccr2, C1qb, Cd74, Vcam1, Cd180, Itgb2, Cd72 and St8sia4 have poor outcome compared to patients who do not have the HTIC signature signature. For example, the "reference expression profile" can be a RNA expression profile or a polypeptide profile. As the expression products of nucleic acid transcripts, polypeptide levels can be expected to correspond to nucleic acid transcript levels, for example mRNA levels, The reference expression profile is an expression signature (e.g. polypeptide or nucleic acid gene expression levels and/or pattern) of two or a plurality of genes (e.g. for example 4 genes), associated with outcome in Her2+ breast cancer patients.

The term "sample" as used herein refers to any breast biological fluid, breast cell or tissue or fraction thereof from a subject that can be assessed for biomarker expression products, polypeptide expression products or nucleic acid expression products, including for example an isolated RNA fraction, optionally mRNA for nucleic acid biomarker determinations and a protein fraction for polypeptide biomarker determinations, and includes for example fresh tissue, frozen cells/tissue and fixed cells/tissue including formalin fixed, paraffin embedded (FFPE) samples. The sample can for example be a test sample which is a patient sample to be tested or a control sample which is a sample with known outcome used for comparison.

The term "sequence identity" as used herein refers to the percentage of sequence identity between two or more polypeptide sequences or two or more nucleic acid sequences that have identity or a percent identity for example about 70% identity, 80% identity, 90% identity, 95% identity, 98% identity, 99% identity or higher identity or a specified region. To determine the percent identity of two or more amino acid sequences or of two or more nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, word_length=3 to obtain amino acid sequences homologous to a protein molecule of the present disclosure. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). The percent identity between two sequences can be determined using techniques similar to those described above, with or without allowing gaps. In calculating percent identity, typically only exact matches are counted.

The term "similar" in the context of a biomarker level as used herein refers to a subject biomarker level that falls within the range of levels associated with a particular class for example associated with poor outcome or good outcome. Accordingly, "detecting a similarity" refers to detecting a biomarker level that falls within the range of levels associated with a particular class. In the context of a reference profile, "similar" refers to the reference profile associated with poor or good outcome or treatment response that shows a number of identities and/or degree of changes with the subject expression profile.

The term "most similar" in the context of a reference profile refers to a reference profile that shows the greatest number of identities and/or degree of changes with the subject expression profile.

The term "specifically binds" as used herein refers to a binding reaction that is determinative of the presence of the biomarker (e.g. polypeptide or nucleic acid) often in a heterogeneous population of macromolecules. For example, when the biomarker specific reagent is an antibody, specifically binds refers to the specified antibody binding with greater affinity to the cognate antigenic determinant than to another antigenic determinant, for example binds with at least 2, at least 3, at least 5, or at least 10 times greater specificity; and when a probe, specifically binds refers to the specified probe under hybridization conditions binds to a particular gene sequence at least 1.5, at least 2 at least 3, or at least 5 times background.

The term "subject" as used herein refers to any member of the animal kingdom, preferably a human being.

The phrase "therapy" or "treatment" as used herein, refers to an approach aimed at obtaining beneficial or desired results, including clinical results and includes medical procedures and applications including for example chemotherapy, pharmaceutical interventions, surgery, radiotherapy and naturopathic interventions as well as test treatments for treating breast cancer for example Her2+ breast cancer. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

Further, the definitions and embodiments described are intended to be applicable to other embodiments herein described for which they are suitable as would be understood by a person skilled in the art. For example, in the above passages, different aspects of the invention are defined in more detail. Each aspect so defined can be combined with any other aspect or aspects unless clearly indicated to the contrary. In particular, any feature indicated as being preferred or advantageous can be combined with any other feature or features indicated as being preferred or advantageous.

II. Methods and Uses

HER2$^+$ breast cancer (BC) is a highly aggressive disease commonly treated with chemotherapy and anti-HER2 drugs, including trastuzumab. There is currently no way to predict which HER2$^+$ BC patients will benefit from these treatments. Previous prognostic signatures for HER2$^+$ BC were developed irrespective of the subtype or the hierarchical organization of cancer in which only a fraction of cells, tumor-initiating cells (TICs), can sustain tumor growth.

It was hypothesized that to be highly predictive, a prognostic signature for HER2$^+$:ERα$^-$ BC should reflect gene expression in enriched TICs for this particular subtype. The development of a prognostic signature (HTICS) for HER2$^+$:ERα$^-$ BC based on transcriptional profiling of highly purified TICs from a mouse model for this subtype is described.

Serial dilution and single cell transplantation assays were used to identify MMTV-Her2/Neu mouse mammary TICs as CD24$^+$:JAG1$^-$ at a frequency of 2-4.5%. A 17-gene Her2-TIC-enriched signature (HTICS), generated on the basis of differentially expressed genes in TIC versus non-TIC fractions and trained on one HER2$^+$ BC cohort, predicted clinical outcome on multiple independent HER2$^+$ cohorts. HTICS included up-regulated genes involved in S/G2/M transition and down-regulated genes involved in immune-response. Its prognostic power was independent of other predictors, stratified lymph node$^+$ HER2$^+$ BC into low and high-risk subgroups (e.g. good and poor outcome groups), and was specific for HER2$^+$:ERα$^-$ patients (10-year overall survival of 83.6% for HTICS$^-$ and 24.0% for HTICS$^+$ tumors (hazard ratio=5.57; P=0.002)). Retrospective analyses revealed that patients with HTICS$^-$ HER2$^+$:ERα$^-$ tumors have good clinical outcome and did not significantly benefit from trastuzumab. In contrast, patients with HTICS$^+$ HER2$^+$:ERα$^-$ tumors resisted chemotherapy but responded to chemotherapy plus trastuzumab. HTIC signature is therefore a prognostic signature for HER2$^+$:ERα$^-$ BC that can be used to identify low risk patients that may not need anti-HER2 therapy such as trastuzumab, and high risk patients that would benefit from anti-HER2 therapy.

Accordingly an aspect of the disclosure includes a method of predicting outcome in a subject with breast cancer, optionally Her2+ breast cancer, comprising:

a. determining an expression level of 2 or more HTIC signature biomarkers selected from Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72, St8sia4 Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86 in a test sample from the subject; and b. comparing the expression level of the 2 or more biomarkers with a control; and c. identifying the subject as having an increased likelihood of poor outcome or a good outcome according to a difference or a similarity in the expression level of the 2 or more biomarkers between the test sample and the control.

In an embodiment, the 2 or more biomarkers are selected from Aurkb, Ccna2, Scrn1, Npy, Atp7b, Chaf1b, Ccnb1, Cldn8, Nrp1, Ccr2, C1qb, Cd74, Vcam1, Cd180, Itgb2, Cd72 and St8sia4.

For example it is demonstrated herein that patients with Her2+ breast cancer tumours that have upregulated (e.g. increased) expression levels of Aurkb, Ccna2, Scrn1, Npy, Atp7b, Chaf1b, Ccnb1 and Cldn8 and downregulated (e.g. decreased) expression levels of Nrp1, Ccr2, C1qb, Cd74, Vcam1, Cd180, Itgb2, Cd72 and St8sia4 have poor outcome, for example have decreased metastasis free survival (MFS) compared to patients with Her2+ breast cancer tumours that do not have the HTIC signature associated with poor outcome. Conversely, HTICS$^-$ HER2$^+$:ERα$^-$ tumors (e.g. BC tumours that do not have the HTIC signature associated with poor outcome) have good clinical outcome.

The control can be for example a reference profile of the 2 or more biomarkers associated with a particular outcome and/or treatment response. A patient which expresses levels of the 2 or more HTIC signature biomarkers that is most similar to a subject with a poor outcome reference signature is classified as having a poor outcome and a patient which expresses levels of the 2 or more HTIC signature biomarkers that is most similar to a subject with a good outcome reference signature is classified as having a good outcome.

In another aspect the disclosure includes a method of identifying a subject with poor outcome Her2+ breast cancer comprising:

a. determining an expression level of 2 or more HTIC signature biomarkers selected from Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72, St8sia4 Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86. in a test sample from the subject; and b. comparing the expression level of the 2 or more biomarkers with a control; and c. identifying the subject as having poor outcome Her2+ breast cancer according to a difference or a similarity in the expression level of the 2 or more biomarkers between the test sample and the control.

Another aspect of the disclosure includes a method of identifying a subject with good outcome Her2+ breast cancer comprising:

a. determining an expression level of 2 or more HTIC signature biomarkers selected from Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72, St8sia4 Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86. in a test sample from the subject; and b. comparing the expression level of the 2 or more biomarkers with a control; and c. identifying the subject as having good outcome Her2+ breast cancer according to a difference or a similarity in the expression level of the 2 or more biomarkers between the test sample and the control.

A further aspect includes a method of identifying whether a subject has a high risk or low risk HER2+ ERα negative breast cancer, the method comprising:

a. determining an expression level of 2 or more HTIC signature biomarkers selected from Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72, St8sia4, Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86 in a test sample from the subject; and b. comparing the expression level of the 2 or more biomarkers with a control; and c. identifying the subject as having high risk HER2+ ERα negative breast cancer or low risk Her2+ ERα negative breast cancer according to a difference or a similarity in the expression level of the 2 or more biomarkers between the test sample and the control.

In an embodiment an increased expression level of Aurkb, Ccna2, Scrn1, Npy, Atp7b, Chaf1b, Ccnb1 and/or Cldn8 and a decreased expression of Nrp1, Ccr2, C1qb, Cd74, Vcam1, Cd180, Itgb2, Cd72 and/or St8sia4 is indicative of an increased likelihood of a poor outcome and/or high risk Her2+ ERα negative breast cancer. In another embodiment, a decreased expression level of Aurkb, Ccna2, Scrn1, Npy, Atp7b, Chaf1b, Ccnb1 and/or Cldn8 and an increased expression of Nrp1, Ccr2, C1qb, Cd74, Vcam1, Cd180, Itgb2, Cd72 and/or St8sia4 is indicative of an increased likelihood of a good outcome and/or low risk Her2+ ERα negative breast cancer.

In an embodiment, an increase in the expression of Aurkb, Ccna2, Scrn1, Npy, Atp7b, Chaf1b, Ccnb1, Cldn8, Kif11, Plk1, Chek1 and/or Mphosph6, and decreased expression of Nrp1, Ccr2, C1qb, Cd74, Vcam1, Cd180, Itgb2, Cd72, St8sia4, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and/or Ly86 predicts an increased likelihood of a poor outcome and/or high risk Her2+ ERα negative breast cancer. In another embodiment, a decrease in the expression of Aurkb, Ccna2, Scrn1, Npy, Atp7b, Chaf1b, Ccnb1, Cldn8, Kif11, Plk1, Chek1 and/or Mphosph6, and an increased expression of Nrp1, Ccr2, C1qb, Cd74, Vcam1, Cd180, Itgb2, Cd72, St8sia4, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and/or Ly86 predicts an increased likelihood of a good outcome and/or low risk Her2+ ERα negative breast cancer.

In an embodiment, the expression levels of the 2 or more biomarkers is compared to the control by calculating a HTIC signature score.

Accordingly an embodiment includes a method of predicting outcome in a subject with Her2+ breast cancer and/or diagnosing a high risk HER2+:ERα negative breast cancer subject comprising:

a. determining a HTIC signature comprising determining an expression level of 2 or more HTIC signature biomarkers selected from Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72, St8sia4 Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86. in a test sample from the subject; and b. calculating a HTIC signature score, the HTIC signature score comprising a sum of the 2 or more HTICs biomarker expression levels;

c. identifying the subject as having a poor outcome and/or a high risk HER2+:ERα negative breast cancer when the HTIC signature score is greater than a selected cut-off or control or identifying the subject as having a good outcome and/or a low risk HER2+:ERα negative breast cancer when the HTIC signature score is less than a selected cut-off or control.

For example, the expression level of two or more HTICS biomarkers is determined in a sample of a subject, as well as the expression of one or more internal normalization standards. The ratio of the HTICs biomarker to the internal normalization standard would be computed (e.g. a normalized expression would be determined) and used to compare for example to a HTICS+ or HTICS– reference profile and/or used to calculate a SSM as described herein. The test sample SSM is above a selected threshold or cut-off, the subject would predicted to have poor outcome and if below a selected threshold or cut-off, a good outcome.

In an embodiment, the formula described in Example 2 is used. A person skilled in the art would recognize that if a different gene index is used, for example if –1 is assigned for genes that are increased and 1 is assigned for genes that are decreased, the group of subjects above and below a selected threshold would be reversed compared to if –1 is assigned for genes that are decreased and 1 is assigned for genes that are increased.

In an embodiment, the expression level of a HTICS biomarker is compared to one or more internal normalization markers, for example to provide a ratio. Normalization is a commonly used technique for comparing expression levels between samples. The ratio is then compared for example to a control or cut-off value or used to calculate a composite score for comparison to cut-off value, such as a preselected cut-off value.

In an embodiment, the subject is ERα negative. In an embodiment, the subject has mutated p53.

The HTIC signature is also for example predictive for treatment response. For example, Her2+; ERα+breast cancer subjects that expressed the HTIC signature (e.g. HTIC$^+$) had poor response to conventional chemotherapy. Accordingly, a further aspect includes a method of predicting treatment response to chemotherapy in a subject with Her2+ ERα– breast cancer comprising:

a. measuring an expression level of 2 or more HTIC signature biomarkers selected from Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72, St8sia4 Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86. in a test sample from the subject; and b. comparing the expression level of the 2 or more biomarkers with a control; and c. predicting a treatment response to chemotherapy for the subject according to a difference or a similarity in the expression level of the 2 or more biomarkers between the test sample and the control. The method can be used for example to select a treatment that is suitable for the class identified.

Accordingly in an embodiment, the method comprises a method of selecting a treatment for a subject with a Her2+ ERα negative breast cancer comprising a. determining an expression level of 2 or more HTIC signature biomarkers selected from Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72, St8sia4 Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86. in a test sample from the subject;

b. comparing the expression level of the 2 or more HTIC signature biomarkers with a control; and c. selecting a treatment suitable according to the expression level of the 2 or more HTIC signature biomarkers.

For example, it is also demonstrated herein that for HTIC signature negative patients adjuvant trastuzumab treatment did not have significant effect for preventing metastasis and/or relapse. This patient group may not need aggressive chemotherapy/trastuzumab treatment. HTICS-negative patients and in particularly those with cardiac problems may benefit from not receiving trastuzumab as first line of therapy.

HTICs positive patients benefited from trastuzumab treatment had reduced metastasis and/or relapse. Such high risk patients should be prioritized for anti Her2 therapy such as trastuzumab—and/or pertuzumab—a new anti-HER2 neutralizing antibody—as well as other anti-HER therapies including for example lapatinib.

In another embodiment, is provided a method of identifying subjects afflicted with Her2+ ERα− breast cancer that benefit from anti-Her2+ therapy, the method comprising:

a. determining an expression level of 2 or more HTIC signature biomarkers selected from Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72, St8sia4 Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86. in a test sample from the subject;

b. comparing the expression level of the 2 or more biomarkers with a control; and c. identifying the subject as having an increased likelihood of benefiting or not benefiting from anti-Her2 therapy according to a difference or a similarity in the expression level of the 2 or more biomarkers between the test sample and the control.

In an embodiment, a subject with a HTICs positive signature (e.g. having a SSM score above a selected cut-off is administered an anti Her2 therapy.

In an embodiment, the 2 or more HTIC signature biomarkers comprise 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 biomarkers selected from HTIC signature biomarkers Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72, St8sia4 Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86.

In an embodiment, the 2 or more HTICS biomarkers are selected from Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72 and St8sia4.

In another embodiment, the method further comprises determining an expression level of 1 or more biomarkers selected from Kif11, Plk1, Chek1, Mphosph6, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and Ly86.

In an embodiment, an increase in the expression of Aurkb, Ccna2, Scrn1, Npy, Atp7b, Chaf1b, Ccnb1, Cldn8, Kif11, Plk1, Chek1 and/or Mphosph6, and/or decreased expression of Nrp1, Ccr2, C1qb, Cd74, Vcam1, Cd180, Itgb2, Cd72, St8sia4, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and/or Ly86 predicts poor outcome or poor treatment response.

In an embodiment, a decrease in the expression of Aurkb, Ccna2, Scrn1, Npy, Atp7b, Chaf1b, Ccnb1, Cldn8, Kif11, Plk1, Chek1 and/or Mphosph6, and/or an increase in the expression of Nrp1, Ccr2, C1qb, Cd74, Vcam1, Cd180, Itgb2, Cd72, St8sia4, Coro1a, Ccl5, Cd3e Hcls1, Vav1, Plek, Arhgdib, Il2rg, Sash3, Lck, Il2rb, Cybb, Cd79b, Sell, Ccnd2, Tnfrsf1b, Rftn1, Rac2 and/or Ly86 predicts good outcome or good treatment response to for example traditional chemotherapy and/or anti-Her2 therapy. In yet another embodiment, an increase in the expression of two or more HTIC signature biomarkers selected from Aurkb, Ccna2, Scrn1, Npy, Atp7b, Chaf1b, Ccnb1 and Cldn8 predicts poor outcome or poor treatment response.

In a further embodiment, a decrease in the expression of 2 or more HTIC signature biomarkers selected from Nrp1, Ccr2, C1qb, Cd74, Vcam1, Cd180, Itgb2, Cd72 and St8sia4 predicts poor outcome or poor treatment response.

In another embodiment, comparing the expression level of the 2 or more biomarkers with the control comprises calculating a signature score match (SSM) and comparing to a selected cut-off level.

In an embodiment, the signature score match is calculated according to the following:

$$\text{Score for Signature Match (SSM)} = \Sigma(I_n X_n / |X_n|) / \Sigma(|I_n|),$$

where I is the gene index; 1 for up-regulated genes in TICs and −1 for down-regulated genes; X is the log 2 transformed and optionally normalized and/or median-centered gene expression value of the patient.

For example, in an embodiment a subject with a SSM≥0 is considered to be a match to the HTIC signature and have poor outcome. In an embodiment, the SSM is >−0.1, >0.1, >0.2 or 0.3. The greater the selected SSM the greater the match to the signature.

In an embodiment, the selected cut-off level, calculated as a SSM, is 0. In an embodiment, the cut off level calculated as an SSM is greater than 0.2.

In another embodiment, a subject SSM greater than the cut-off level predicts poor outcome or poor treatment response and a subject SSM less than the cut-off is indicative or good outcome or traditional chemotherapy treatment response.

In an embodiment, poor outcome is reduced overall survival, disease free survival and/or metastasis free survival.

In another embodiment, good outcome is increased overall survival, disease free survival and/or metastasis free survival.

In yet a further embodiment, the expression level of the 2 or more biomarkers in the test sample is a normalized expression level, normalized with one or more endogenous normalization genes to determine the relative expression of each biomarker, which is used to calculate a SSM for the subject test sample, the SSM is used to classify the subject as having a poor outcome or a good outcome.

In an embodiment, the control for example the control cut off level comprises the median, or corresponds to the lowest 50%, 40%, 30%, 20% or 10% expression levels in in a population of subjects (e.g. control population) with known good outcome.

In an embodiment, the increase in expression of one or more of the biomarkers is at least 10%, at least 20%, at least 30%, at least 40%, at least 50%, at least 60%, at least 70%, at least 80%, at least 90%, at least 100%, at least 1.5 fold, at least 2 fold, at least 3 fold, at least 4 fold or at least 5 fold increased compared to a control.

Similarity can be assessed for example by determining if the similarity between an expression profile and a reference profile is above or below a predetermined cut off or threshold.

Accordingly, in another embodiment, the method comprises:

a) calculating a measure of similarity between an expression profile and one or more reference expression profiles, the expression profile comprising the expression levels of a first plurality of biomarkers in a sample taken from the subject; the one or more reference expression profiles associated with poor or good outcome comprising, for each biomarker of the plurality, the average or median expression level of the gene in a population of subjects associated with the reference expression profile; the plurality of biomarkers comprising two or more of the HTIC biomarkers; and b) classifying the subject as having a poor outcome if the expression profile has a high similarity to the reference expression profile associated with poor outcome or has a higher similarity to the reference expression profile associated with poor outcome than to the reference expression profile associated good outcome or classifying the subject as having a good outcome if the expression profile has a low similarity to the reference expression profile reference expression profile associated with poor outcome or has a higher similarity to the reference expression profile associated with good outcome than to the reference expression profile associated with poor outcome; wherein the expression profile has a high similarity to the reference expression profile associated with poor outcome if the similarity to the reference profile associated with poor outcome is above a predetermined threshold, or has a low similarity to the reference profile associated with poor outcome if the similarity to the reference expression profile associated with poor outcome is below the predetermined threshold.

In an embodiment, the expression level determined is a nucleic acid expression level.

For example, determining the biomarker expression level can comprise use of quantitative PCR, such as quantitative RT-PCR, serial analysis of gene expression (SAGE), microarray, digital molecular barcoding technology, such as Nanostring analysis or Northern Blot or other probe based or amplification based assay.

Determining the biomarker expression level can comprise amplification of the nucleic acid expression level using a primer or primer set and/or using probe hybridization based methods such as an array and/or digital molecular barcoding technology (e.g. nanostring technology).

For example, Nanostring, probe-based assay, and Q-RT-PCR can be used to detect and measure gene expression levels in formalin-fixed, paraffin embedded samples.

In an embodiment, where the sample comprises RNA derived from a fresh and/or frozen sample, quantification can be by microarray and/or nanostring technology. In an embodiment, where the sample is a clinical sample, the use of nanostring technology is preferred.

In an embodiment, the biomarker detection agent is a probe.

In an embodiment, the probe is to Aurkb and binds to a sequence in NM_004217, for example binding or binding within nucleotides 615-715. In an embodiment, the probe comprises at least 10, at least 15 at least 20, at least 25 nucleotides, at least 30, at least 35, at least 40, at least 45, at least 50, at least 55, at least 60, at least 65, at least 70, at least 75, at least 80, at least 85 or at least 90 nucleotides of SEQ ID NO:1. In an embodiment, the probe comprises and/or consists essentially of the nucleotide sequence of SEQ ID NO:1.

In an embodiment, the probe is to Ccn2 and binds to a sequence in NM_001237, for example binding or binding within nucleotides 1210-1310. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:2. In an embodiment, the probe comprises and/or consists essentially of the nucleotide sequence of SEQ ID NO:2.

In an embodiment, the probe is to Scrn1 and binds to a sequence in NM_014766, for example binding or binding within nucleotides 2045-2145. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:3. In an embodiment, the probe comprises and/or consists essentially of the nucleotide sequence of SEQ ID NO:3.

In an embodiment, the probe is to Npy and binds to a sequence in NM_000905, for example binding or binding within nucleotides 270-370. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:4. In an embodiment, the probe comprises and/or consists essentially of the nucleotide sequence of SEQ ID NO:4.

In an embodiment, the probe is to Atp7b and binds to a sequence in NM_000053 for example binding or binding within nucleotides 675-775. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:5. In an embodiment, the probe comprises and/or consists essentially of the nucleotide sequence of SEQ ID NO:5.

In an embodiment, the probe is to Chaf1b and binds to a sequence in NM_005441, for example binding or binding within nucleotides 795-895. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:6. In an embodiment, the probe comprises and/or consists essentially of the nucleotide sequence of SEQ ID NO:6.

In an embodiment, the probe is to Ccnb1 and binds to a sequence in NM_031966, for example binding or binding within nucleotides 715-815. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:7. In an embodiment, the probe comprises and/or consists essentially of the nucleotide sequence of SEQ ID NO:7.

In an embodiment, the probe is to Cldn8 and binds to a sequence in NM_199328, for example binding or binding within nucleotides 805-905. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:8. In an embodiment, the probe comprises and/or consists essentially of the nucleotide sequence of SEQ ID NO:8.

In an embodiment, the probe is to Nrp1 and binds to a sequence in NM_003873, for example binding or binding within nucleotides 370-470. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:9. In an embodiment, the probe comprises and/or consists essentially of the nucleotide sequence of SEQ ID NO:9.

In an embodiment, the probe is to Ccr2 and binds to a sequence in NM_000647, for example binding or binding within nucleotides 20-120. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:10. In an embodiment, the probe comprises and/or consists essentially of the nucleotide sequence of SEQ ID NO:10.

In an embodiment, the probe is to C1qb and binds to a sequence in NM_000491, for example binding or binding within nucleotides 819-919. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:11. In an embodiment, the probe comprises and/or consists essentially of the nucleotide sequence of SEQ ID NO:11.

In an embodiment, the probe is to CD74 and binds to a sequence in NM_004355, for example binding or binding within nucleotides 964-1064. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:12. In an embodiment, the probe comprises and/or consists essentially of the nucleotide sequence of SEQ ID NO:12.

In an embodiment, the probe is to Vcam1 and binds to a sequence in NM_001078, for example binding or binding within nucleotides 2535-2635. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:13. In an embodiment, the probe comprises and/or consists essentially of the nucleotide sequence of SEQ ID NO:13.

In an embodiment, the probe is to CD180 and binds to a sequence in NM_005582, for example binding or binding within nucleotides 20-120. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:14. In an embodiment, the probe comprises and/or consists essentially of the nucleotide sequence of SEQ ID NO:14.

In an embodiment, the probe is to Itgb2 and binds to a sequence in NM_000211, for example binding or binding within nucleotides 520-620. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:15. In an embodiment, the probe comprises and/or consists essentially of the nucleotide sequence of SEQ ID NO:15.

In an embodiment, the probe is to Cd72 and binds to a sequence in N NM_001782, for example binding or binding within nucleotides 1044-1144 In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:16. In an embodiment, the probe comprises and/or consists essentially of the nucleotide sequence of SEQ ID NO:16.

In an embodiment, the probe is to St8sia4 and binds to a sequence in NM_175052, for example binding or binding within nucleotides695-795. In an embodiment, the probe comprises at least 10, at least 15, at least 20, at least 25, at least 30, at least 35, at least 40, at least 45, at least 50, at least 55, at least 60, at least 65, at least 70, at least 75, at least 80, at least 85 or at least 90 nucleotides of SEQ ID NO:17. In an embodiment, the probe comprises and/or consists essentially of the nucleotide sequence of SEQ ID NO:17.

Figure 16:
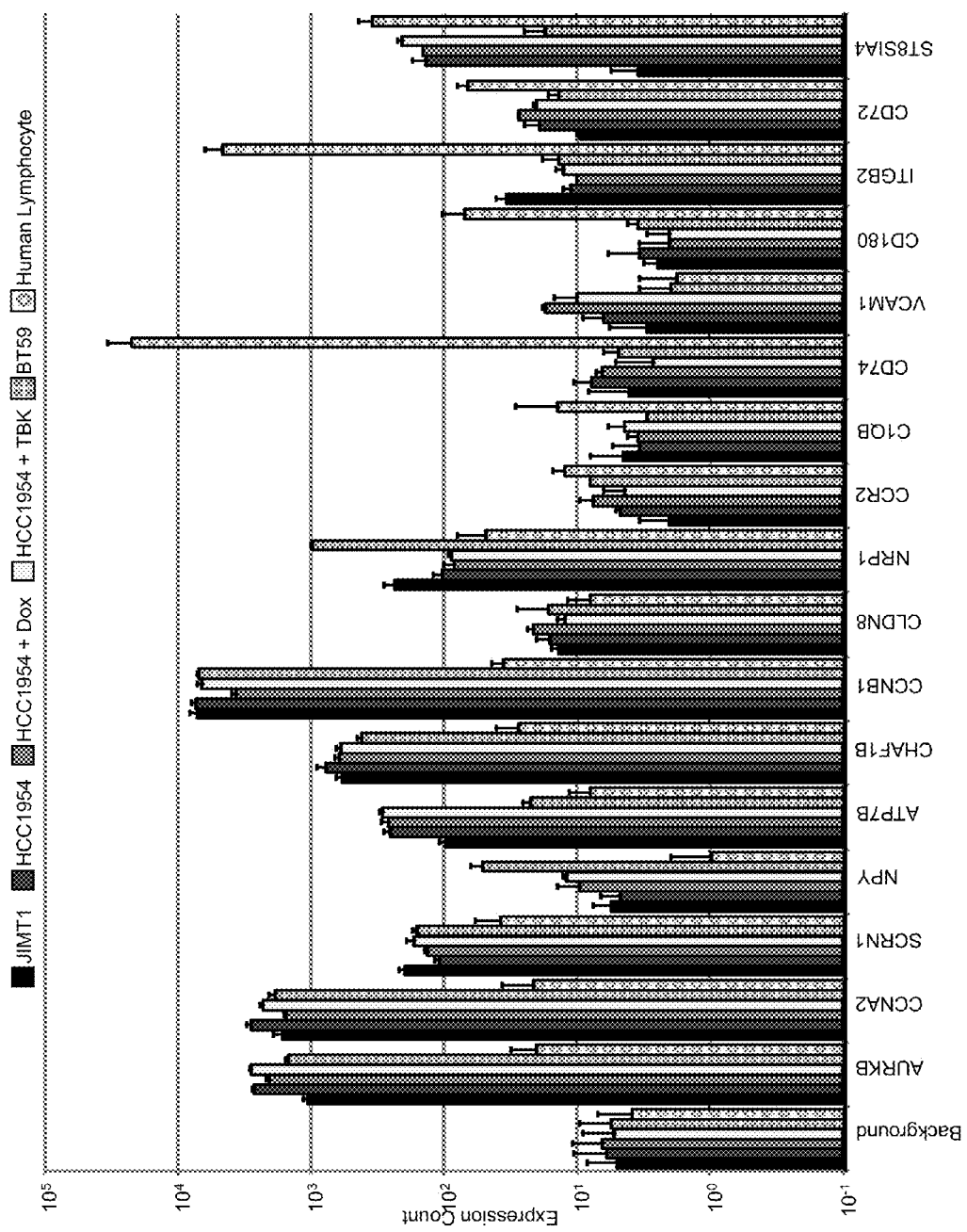
FIG. 16. Significant Nanostring Detection Demonstrated for Every Gene in HTICS in Human Cells.
Figure 17:
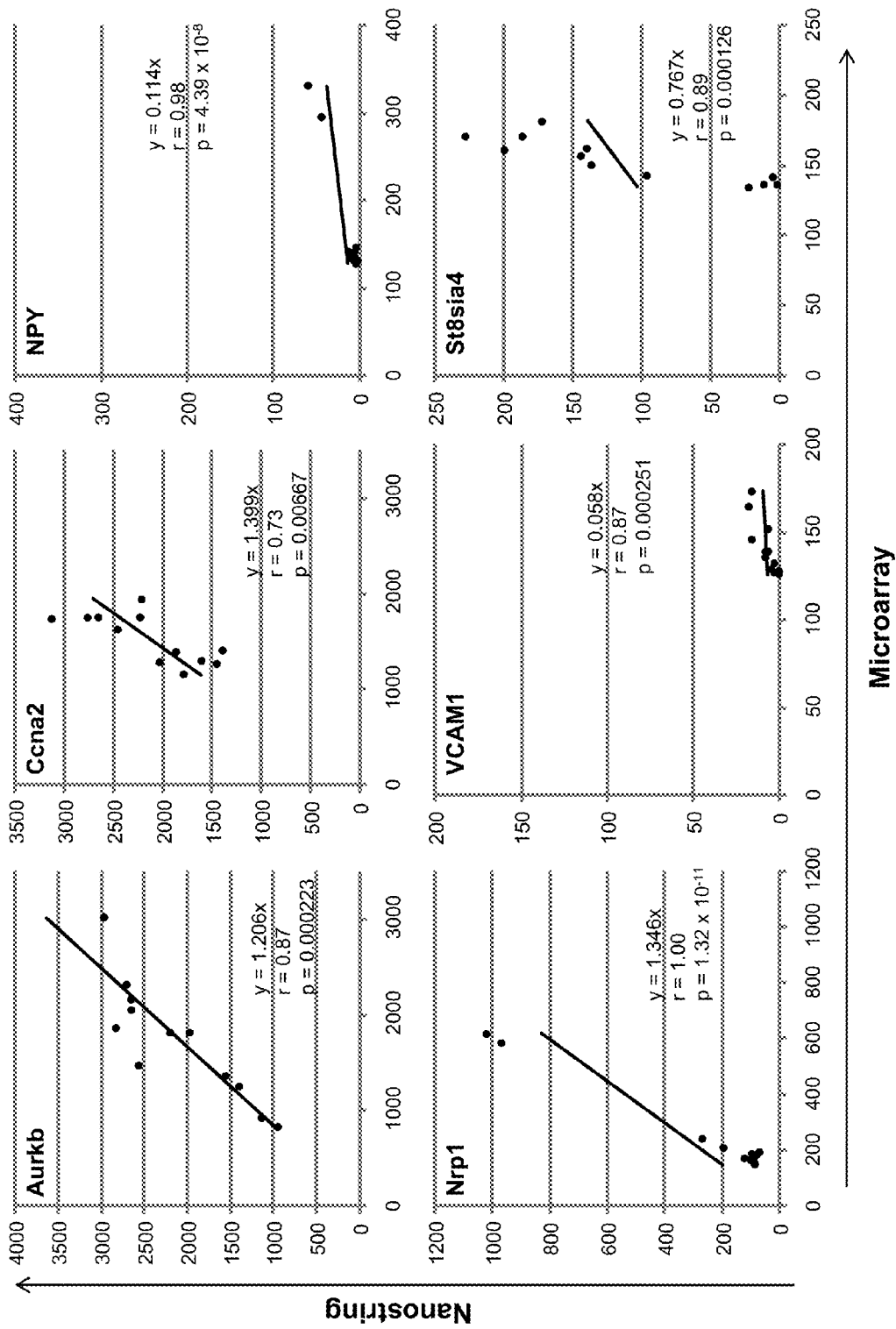
FIG. 17. Representative Examples of Correlation Analysis of HTICS Genes Expression by Nanostring vs Microarray in Human Breast Cancer Cell Lines.

As demonstrated in FIG. 17, microarray and nanostring assays show positive and consistent correlation in RNA from human breast cancer cell lines. FIG. 16 demonstrates significant nanostring detection for each of the HTICS genes in human cells. The probes described are optionally used in nanostring methods and/or microarray methods.

In still another embodiment, the expression level determined is a polypeptide level.

For example, the biomarker expression level can be determined using an antibody that specifically binds to the polypeptide and assaying the polypeptide level by optionally immunohistochemistry.

In an embodiment, the method comprises first obtaining a sample.

A further aspect of the disclosure includes a method of treating a breast cancer subject in need thereof comprising:
  a. obtaining a test sample from the subject;
  b. predicting the outcome and/or treatment response according to a method described herein; and
  c. administering to the subject a treatment suitable according to the predicted outcome or treatment response.

In an embodiment where the subject is predicted to have a poor outcome (e.g. HTICS+), the treatment comprises adjuvant anti-Her2 treatment.

In an embodiment, where the subject is predicted to have a good outcome (e.g. HTICS), the treatment excludes adjuvant anti-Her2 treatment, for example comprises chemotherapy treatment.

In an embodiment, the anti-Her2 treatment is selected from trastuzumab, Lapatinib, pertuzumab and other anti-HER2 agents.

In an embodiment, the chemotherapy is selected from fluorouracil/epirubicin or adriamycin/cyclophosphamide-taxol and other BC regimens.

The expression levels of the HTIC signature biomarkers can be determined using an RNA microarray on fresh tumor biopsies or NanoString assay on formalin fixed, paraffin-embedded (FFPE) and/or fresh tumour biopsies.

Also provided are uses of the HTIC signature biomarkers for diagnosing, prognosing, selecting a treatment, and treating breast cancer.

An aspect provides use of a HTIC signature for treating a subject with breast cancer, the method comprising predicting the subject's outcome and/or treatment response according to a method described herein; wherein the predicted outcome determines a treatment suitable for treating the subject.

Accordingly a further aspect includes an array comprising, for each of a plurality of HTIC signature biomarkers selected from Aurkb, Ccna2, Scrn1, Npy, Atp7b, Chaf1b, Ccnb1, Cldn8, Nrp1, Ccr2, C1qb, Cd74, Vcam1, Cd180, Itgb2, Cd72 and St8sia4, one or more polynucleotide probes complementary and hybridizable to an expression product of the HTIC signature biomarker.

In an embodiment, the array consists of, for each of a plurality of HTIC signature biomarkers selected from Aurkb, Ccna2, Scrn1, Npy, Atp7b, Chaf1b, Ccnb1, Cldn8, Nrp1, Ccr2, C1qb, Cd74, Vcam1, Cd180, Itgb2, Cd72 and St8sia4, and one or more positive and/or negative assay controls; one or more polynucleotide probes complementary and hybridizable to an expression product of the HTIC signature biomarker.

The plurality of polynucleotide probes are for example coupled to a solid support, such as a slide or glass plate. The solid support can be for example a silicon, a plastic, a glass, a ceramic, a rubber, a metal, a polymer, a paper material and/or a combination thereof. The array can be used to identify expression levels of 2 or more HTICS biomarkers, under hybridization conditions where discriminations can be made between matched and mismatched oligonucleotide probes.

In an embodiment, the array is an antibody array comprising, for each of a plurality of HTIC signature biomarkers selected from Aurkb, Ccna2, Scrn1, Npy, Atp7b, Chaf1b, Ccnb1 Cldn8, Nrp1, Ccr2, C1qb, Cd74, Vcam1, Cd180, Itgb2, Cd72 and St8sia4, one or more antibodies specific for a polypeptide expression product of the HTIC signature biomarker.

A further aspect includes a kit for use with the method described herein, comprising at least two biomarker specific agents, such as polynucleotide probes, each of which detects or can be used to determine the expression level of a HTIC signature biomarker selected from Aurkb, Ccna2, Scrn1, Npy, Atp7b, Chaf1b, Ccnb1, Cldn8, Nrp1, Ccr2, C1qb, Cd74, Vcam1, Cd180, Itgb2, Cd72 and St8sia4, a container and optionally a kit control.

In an embodiment, the kit comprises an array described herein, a kit control; and optionally instructions for use.

In another embodiment, the kit further comprises reagents for qRT-PCR. For example, the kit can comprise the kit comprise one or more of PCR buffer, dNTPs, polymerase and $MgCl_2$ In a further embodiment, the biomarker specific reagent is a probe, or primer set that amplifies a nucleic acid transcript of the biomarker.

In an embodiment, the kit comprises a Gene Expression Panel comprising probes to two or more HTICS biomarkers. In yet another embodiment, the kit further comprises reagents for digital molecular barcoding technology In an embodiment, the kit comprises one or more probes specific for one or more HTIC signature biomarkers disclosed herein, for example comprising 10 or more nucleotides of any one of SEQ ID NO: 1-17.

In an embodiment, the kit comprises one or more nanostring probes for each of the HTICS biomarkers and optionally probes for 1, 2, 3, 4 or 5 internal standardization markers (e.g. internal control genes).

The kit can also comprise sterile vessels for obtaining a sample, and the vessel can be uniquely labelled. The kit can also comprise a sample preservation fluid, for example for formaldehyde fixing etc, that prevents degradation of the sample until analysis.

The methods or parts thereof described herein can be computer implemented. In an embodiment, the method further comprises: displaying or outputting to a user interface device, a computer readable storage medium, or a local or remote computer system, the classification produced by the classifying step disclosed herein; and/or an indication of the likelihood of recurrence or a value (such as a risk score) corresponding to the likelihood of recurrence. In another embodiment, the method comprises displaying or outputting a result of one of the steps to a user interface device, a computer readable storage medium, a monitor, or a computer that is part of a network.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present application:

EXAMPLES

Example 1

HTICS identifies a subgroup of $HER2^+:ER\alpha^-$ patients that does not respond well to conventional chemotherapy but benefits from trastuzumab, and may therefore be used to identify and prioritize high-risk $HER2^+:ER\alpha^-$ patients for anti-HER2 therapy.

Results

Enrichment of Her2/Neu TICs in $CD24^+:JAG1^-$ fraction. In this study, we used a mouse model of $HER2^+$ BC, MMTV-Her2/Neu, which sprouts mammary tumors with similar characteristics as the human disease (13). Previously, mammary TICs were identified in this model in the $CD31^-$, CD45, $TER119^-$ (lineage depleted—$lin^-$), $7AAD^-$ (live), $CD24^+$ cell fraction at a frequency of ~1/300 (14). The cell surface markers CD49f, Sca-1, CD29, CD90, CD18 and CD14 failed to subdivide the $CD24^+$ cell population for enrichment of TICs (14, 15). We found that mechanical rather than enzymatic dissociation improved recovery of Her2/Neu TICs ~3 folds to 1/84 (FIG. 1A). As levels of the Notch-ligand Jagged1 (JAG1) can predict outcome in BC (16), we tested for expression of Jagged1 and its receptor Notch1 in $lin^-$ $CD24^+$ cells by flow cytometry. Interestingly, both Jagged1 and Notch1 independently subdivided the $CD24^+$ fraction into two populations (FIG. 1B). Immunostaining of Neu tumors confirmed widespread expression of Jagged1 (FIG. 1C).

To test whether these antigens could enrich TICs, tumor cells were sorted on the basis of CD24 plus JAG1 or Notch1 expression, serially diluted and transplanted into mammary glands of syngeneic mice. TIC frequency varied from tumor to tumor but was consistently higher in $CD24^+:JAG1^-$ relative to $CD24^+:JAG1^+$ cells in 6 different tumors (FIG. 1D). Overall TIC frequency in the $CD24^+:JAG1^-$ fraction was 1/47 (~2%) as compared to 1/172 in the $CD24^+:JAG1^+$ population (3.6 fold enrichment) and 1/455 in the $lin^-$ population (9.7 fold enrichment). TICs were also enriched 2.4 fold in the $CD24^+:Notch1^-$ fraction relative to $CD24^+$: $Notch1^+$ (FIG. 1D; top). Flow cytometry profiles of secondary tumors arising after transplantation of either $CD24^+$: $JAG1^-$ or $CD24^+:JAG1^+$ cells were similar to primary tumors (FIG. S1A), suggesting the presence of some contaminating CD24$^+$:JAG1$^-$ TICs in the CD24$^+$:JAG1$^+$ fraction, or that both fractions contained TICs, albeit at different frequencies, and that the JAG1$^-$ and JAG1$^+$ states were interconnected.

Figure 7:
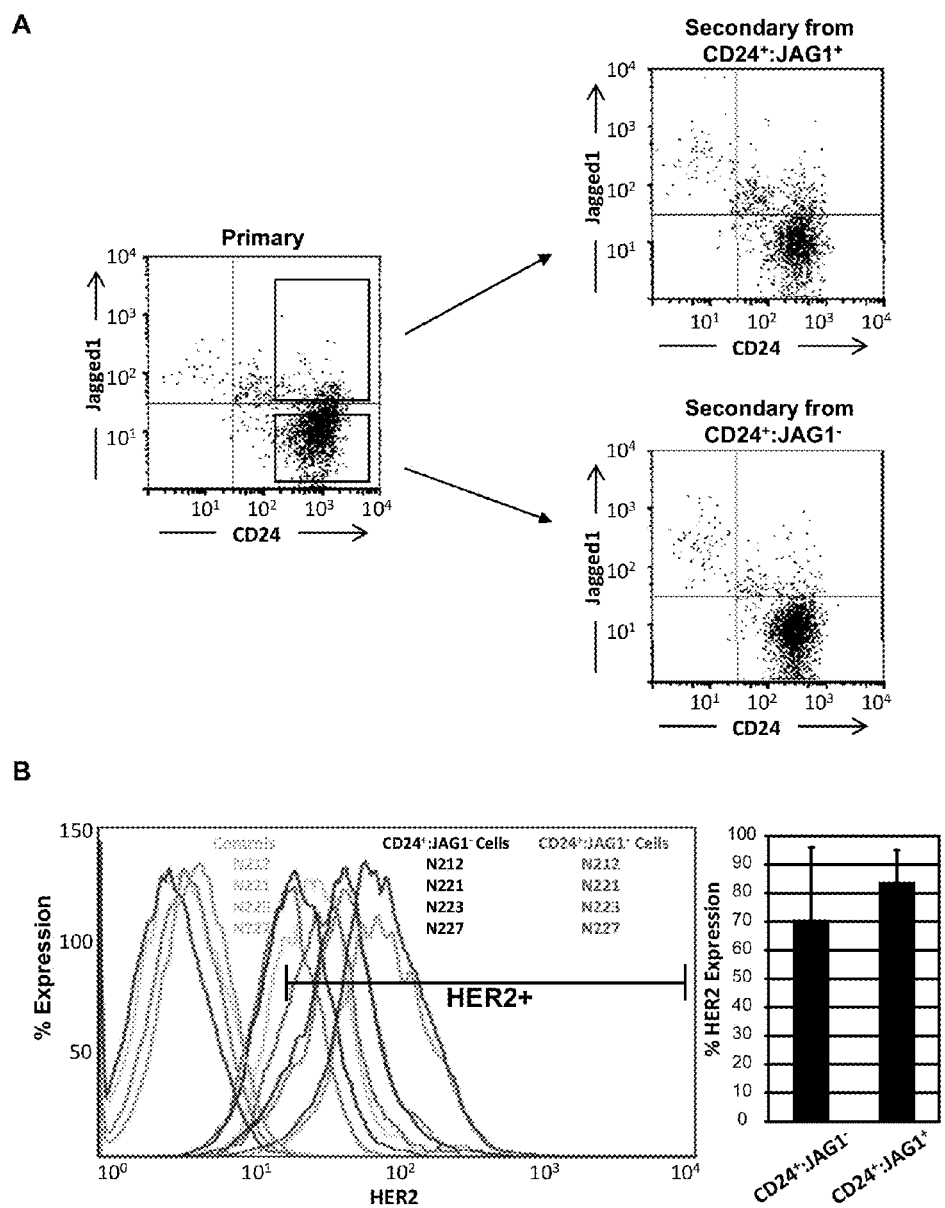
FIG. 7. (A) TICs in $CD24^+$:$JAG1^+$ and $CD24^+$:$JAG1^-$ fractions regenerate the cellular complexity of Neu mammary tumors. Left, Flow cytometry profile of a primary Neu tumor and gated $CD24^+$:$JAG1^+$ and $CD24^+$:$JAG1^-$ cells used for transplantation. Right, Flow cytometry profiles of secondary tumors derived from transplantation of 500 $CD24^+$:$JAG1^+$ (top) or $CD24^+$:$JAG1^-$ (bottom) cells, demonstrating that both fractions regenerated the cellular complexity seen in primary Neu tumors. (B) Similar expression of HER2 in $CD24^+$:$JAG1^-$ and $CD24^+$:$JAG1^+$ fractions. Left, levels of HER2/NEU expression in $CD24^+$:$JAG1^-$ and $CD24^+$:$JAG1^+$ populations estimated by flow cytometry analysis of 4 independent tumors (N212, N221, N223 and N227). Right, average expression of HER2/NEU in the $CD24^+$:$JAG1^-$ and $CD24^+$:$JAG1^+$ fractions based on the flow cytometry analysis (n=4).
Figure 8:
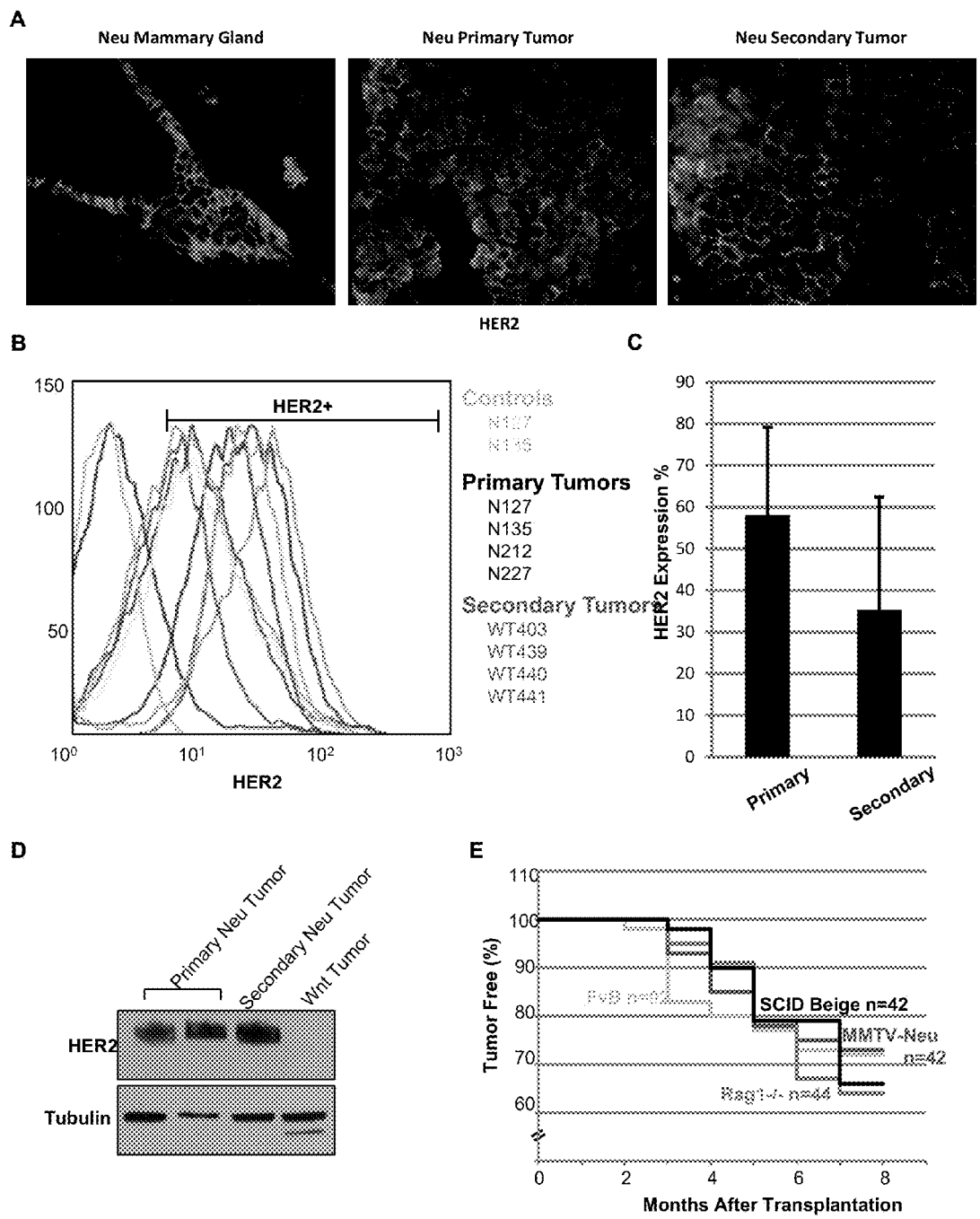
FIG. 8. Expression of HER2/NEU in primary and secondary MMTV-Neu tumors, and transplantation efficiency in isogenic versus immuno-compromised mice. (A) Representative immunofluorescent staining for HER2/NEU in MMTV-Neu mammary gland, primary and secondary tumors. DAPI was used to stain nuclei. (B) HER2/NEU expression quantified by flow cytometry, comparing four primary tumors (N127, N135, N212 and N227) to four secondary tumors induced in FvB host (WT403, WT439, WT440, and WT441). (C) Percentage of HER2/NEU expression in the primary and secondary tumors shown in panel B, demonstrating non-statistically significant reduction in protein expression in secondary tumors. (D) Western blot analysis for HER2/NEU in primary and secondary tumors. Protein lysate from a MMTV-Wnt1 tumor was used as negative control. Tubulin served as a loading control. (E) Kaplan-Meier tumor-free curve for sorted MMTV-Neu $CD24^+$ tumor cells transplanted into the mammary glands of 3-5 week-old syngeneic FvB mice (n=92 injection), MMTV-Neu mice (n=42), immuno-deficient $Rag1^{-/-}$ (n=44) and SCID Beige mice (n=42), demonstrating that transplantation efficiency of MMTV-Neu tumor cells is similar in immuno-competent and immuno-compromised mice.

The HER2/NEU and NOTCH1 pathways antagonize each other (17). However, we found that HER2/NEU expression in 4 independent tumors was not statistically different in CD24$^+$:JAG1$^+$ relative to CD24$^+$:JAG1$^-$ cells (FIG. 7), indicating that JAG1 does not significantly affect HER2/NEU expression in this mouse model. It was previously reported that the MMTV-Her2/Neu transgene, which encodes rat Her2/Neu (13, 18), elicits immuno-rejection or immuno-editing response in transplanted mice, leading to silencing of the transgene in secondary tumors (19). However, secondary tumors expressed HER2 at comparable levels as primary tumors, and incidence of tumor formation was as high in isogenic immuno-competent recipient mice as in immuno-compromised mice (FIG. 8), Thus, at least following transplantation of a small number of lin$^-$ cells (≤50) the rat Her2/Neu transgene does not induce overt immuno-rejection in mice.

Her2/Neu TICs are Functionally Stable

Figure 2:
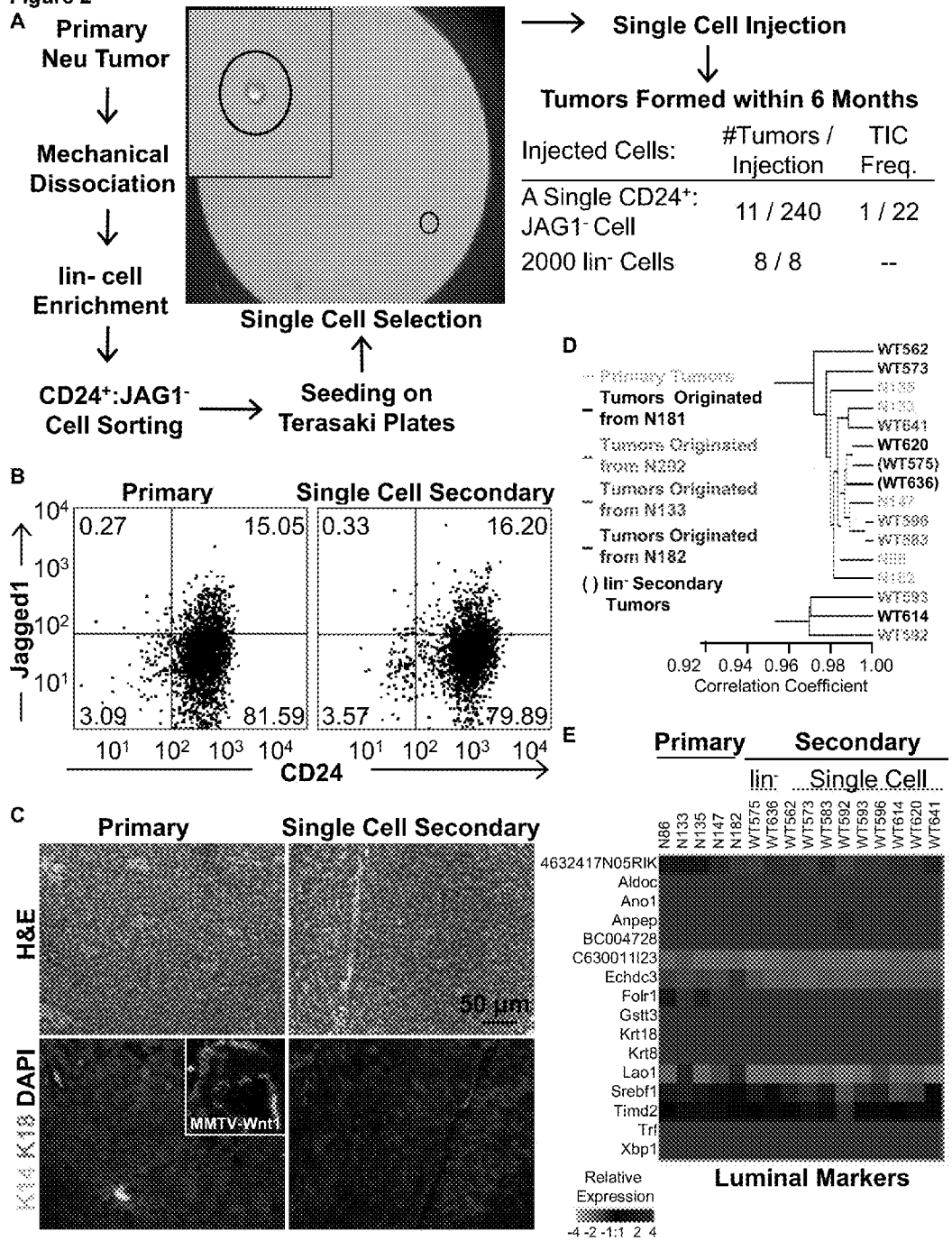
FIG. 2. $CD24^+$:$JAG1^-$ TICs are functionally stable. (A) Scheme for single cell transplantation assays. (B) Representative flow cytometry profiles for CD24 and Jagged1 of primary and single ($CD24^+$:$JAG1^-$) cell-derived Neu tumors. (C) Histology and marker analysis of primary and single cell-derived tumors: Keratin 14 (K14) and 18 (K18). Inlets—positive staining of Keratin14 plus Keratin18 in MMTV-Wnt1 tumors. (D) Cluster analysis of primary, $lin^-$-derived and single cell-derived Neu tumors showing close clustering with >0.95 correlation coefficient. (E) Heatmap of representative luminal and Her2/neu genes in indicated tumors.

Cancer heterogeneity due to clonal evolution and functional instability of TICS can lead to occurrence of distinct secondary tumors (20), complicating generation of TIC-based prognostic signatures. To test for functional stability of CD24$^+$:JAG1$^-$ Her2/Neu TICs, we performed single cell transplantation assays as depicted in FIG. 2A. Tumors (n=4; N133, N181, N182, N202) were mechanically dissociated, lineage-depleted and sorted for single, live (PI negative), CD24$^+$:JAG1$^-$ cells. Sorted cells were seeded, 1 cell per well, into Terasaki plates, which have a conical flat bottom, facilitating identification of wells with single cells (FIG. 2A, inlet). Content of each well containing a single cell was mixed with matrigel and injected into the #4 mammary gland of 4-5 week old FvB female mouse. For each tumor, we performed 60 single cell injections. The entire procedure, from tumor resection to transplantation took ~12 hrs. Of 240 injections, 11 mice developed mammary tumors within 6 months (average latency 3.9 months) with an overall frequency of 1/22 (~4.6%) (FIG. 2A). TIC frequency for the four individual tumors was 1/30 for N133 (i.e. 2 tumors/60 single cell injections), 1/30 for N181 (2/60), 1/20 for N182 (3/60), and 1/15 for N202 (4/60). As control, we injected female mice with 2000 lin$^-$ tumor cells; all injected mice in this group developed tumors (termed lin$^-$-derived tumors).

Figure 9C:
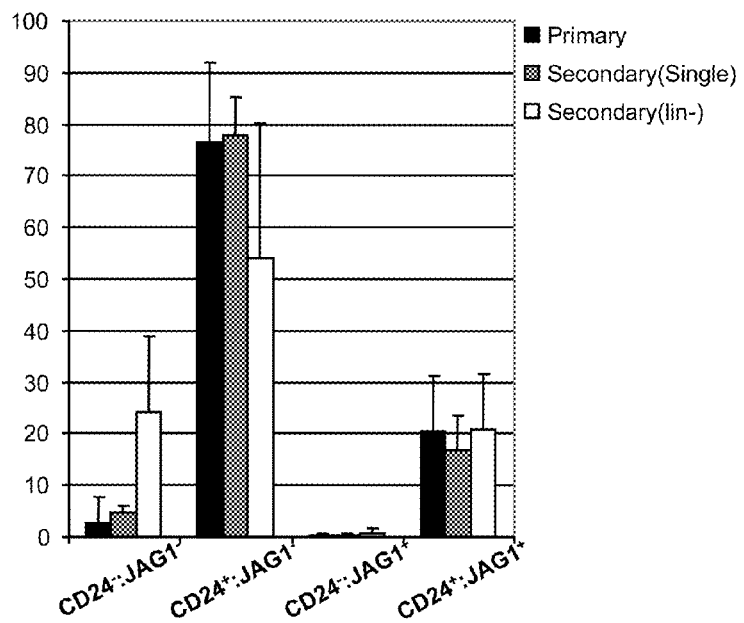
FIG. 9. Single cell derived tumors are indistinguishable from primary MMTV-Neu tumors. (A-B) Representative flow cytometry profiles for CD24 plus CD49f, Sca1 or Jagged1 of representative primary, $lin^-$-derived and single ($CD24^+$:$JAG1^-$) cell-derived Neu tumors. The outlier WT614 exhibits high level of CD24-JAG1 double positive cell population but similar profiles for CD24-Sca1 and CD24-CD49f. (C) Distribution of cells according to CD24-JAG1 expression is similar in single cell-derived and primary tumors. Graphic presentation (top) and numerical data (bottom) for CD24-JAG1 expression in primary versus $lin^-$ derived or single ($CD24^+$:$JAG1^-$) cell-derived secondary tumors, showing similar distribution of $CD24^+$:$JAG1^-$ and $CD24^+$:$JAG1^+$ cells across multiple samples. (D-E) Histology (H&E staining) and immunofluorescentanalysis of representative primary, $lin^-$-derived and single cell-derived tumors for Keratin14 (K14), Keratin18 (K18), Vimentin and HER2/NEU. DAPI was used to label nuclei. Note similar histology and marker expression in the various tumors including the WT614 outlier. (F-H) Representative microarray expression profiles of primary, lin⁻-derived and single cell-derived Neu tumors showing that single cell derived tumors exhibit similar gene profiles and cluster together. Heatmaps for selected genes representing (F) the luminal gene cluster, basal and proliferation markers; (G) the HER2 signaling pathway; (H) cell-cycle markers. (I-K) Differentially expressed genes identified by microarray analysis of single cell-derived tumors versus primary and lin⁻-derived MMTV-Neu tumors. (I) A heatmap for 20 genes (of the 25,600 genes on the Illumina chip) with significant difference in expression ($\geq 2$) in single cell-derived tumors versus primary or lin⁻-derived tumors. (J) Genes with significant decrease of expression ($\leq 0.5 \times$) in single cell-derived tumors. (K) Genes with significant increase of expression ($\geq 2.0 \times$) in single cell-derived tumors. Note abundance of interferon-associated factors: Ifl27, Ly6a, Ly6c, Cc19, H2-T10, H2-Q8, H2-M3.
Figure 9F:
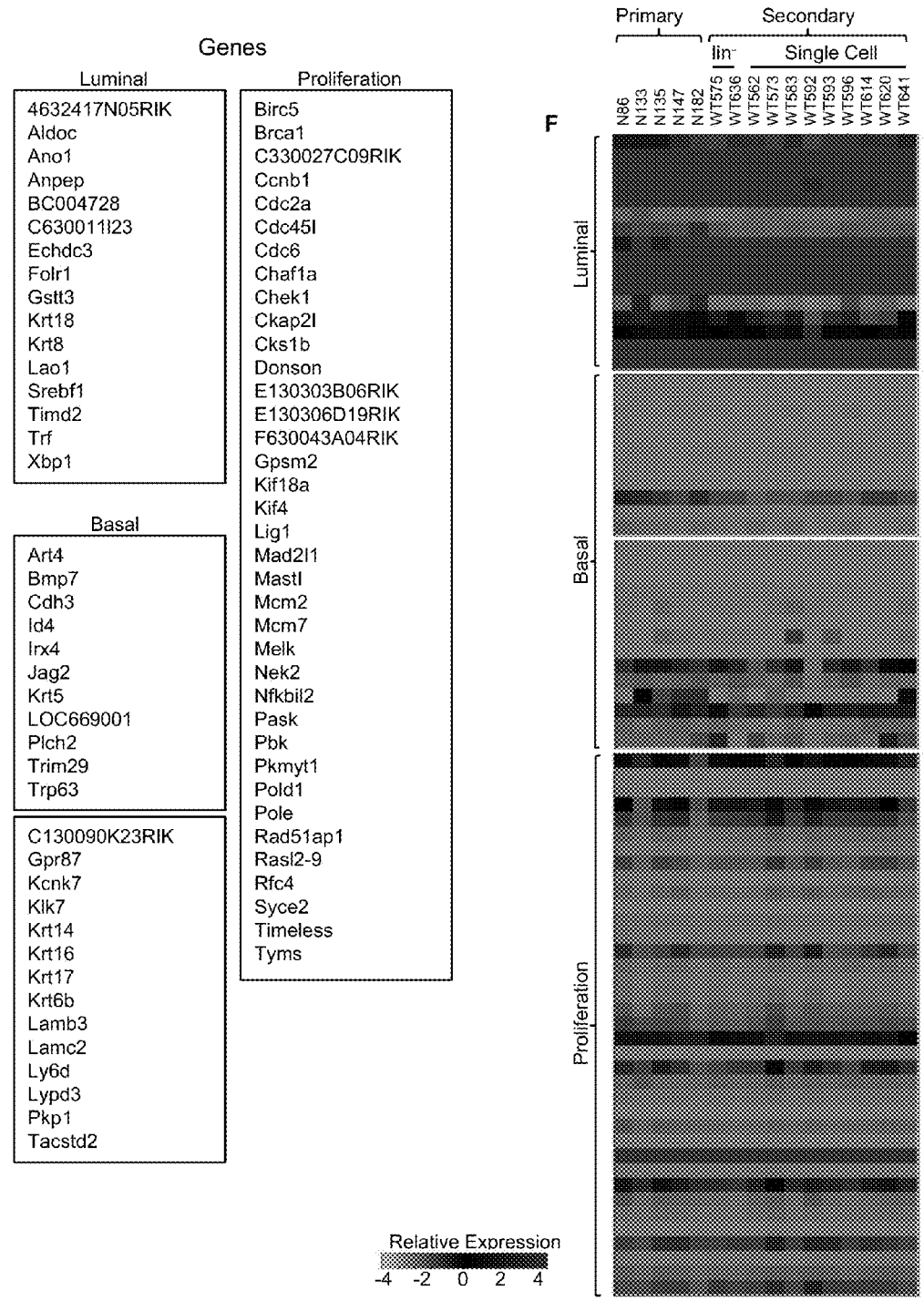

We next determined whether individual secondary tumors were similar to the tumors from which they were derived as well as to other primary and secondary tumors. With the exception of one single-cell derived tumor, WT614, all exhibited similar flow cytometry profiles for CD24 plus Sca1, CD49f or JAG1, as did primary and lin$^-$-derived tumors (FIG. 2B; FIGS. 9A-C). Notably, single cell derived tumors gave rise not only to CD24$^+$:JAG1$^-$ but also to CD24$^+$:JAG1$^+$ cells, indicating that they could expand and regenerate the cellular complexity found in Her2/Neu tumors. The outlier, WT614, showed an expanded CD24$^+$:JAG1$^+$ fraction, but similar profiles for CD24-Sca1 and CD24-CD49f (FIG. 9A-C). The single cell-derived tumors, like primary Her2/Neu tumors and bulk lin$^-$-derived tumors, exhibited a similar histology of poorly differentiated adenocarcinoma as well as similar expression of HER2 and the luminal marker cytokeratin 18, with no expression of K14 or vimentin (FIG. 2C, FIG. 9D-E). Finally, transcriptional profiling and hierarchical clustering revealed that tumors derived from single cell injections (n=9), injections of lin$^-$ cells (n=2), as well as primary tumors (n=5) clustered together with a correlation coefficient of over 0.95, indicating a high degree of similarity among samples (FIG. 2D-E; FIG. 9F-H). Only 16 genes, enriched in interferon-associated factors, were differentially expressed in single cell-derived tumors relative to primary lesions (FIG. 9I-K). Thus, CD24$^+$:Jag1$^-$ Her2/Neu TICs are functionally stable and their frequency is ~2% (serial dilution) to 4.6% (single cell transplantation).

The CD24$^+$:JAG1$^-$ Her2/Neu TIC Fraction is Enriched in Cell Division-associated Pathways and Depleted for Differentiation Pathways To gain an insight into molecular regulations that determine Her2$^+$ TIC function, we analyzed genes and pathways specifically expressed in TIC-enriched cell populations. Four independent MMTV-Neu primary mammary tumors (N250, N261, N283, N222/N229) were harvested, lin$^-$ cells were sorted according to CD24 and JAG1 expression and subjected to gene expression microarray analysis. With the exception of CD24 which, as expected, was elevated in TICs, expression of several luminal markers was high and similar in TIC and non-TIC fractions, whereas expression of basal-markers was generally low in both fractions (FIG. 3A).

Using Gene Set Enrichment Analysis (GSEA) software (21) and "Functional Enrichment Maps" to visualize the results (22), we identified marked differences in pathway activity in CD24$^+$:JAG1$^-$/TIC versus CD24$^-$/non-TIC populations, with 262 up-regulated and 492 down-regulated gene-sets (FIG. 3B). Gene-sets enriched in the TIC fraction included pathways associated with cell division; the non-TIC fraction was enriched in pathways associated with differentiation as well as immune response and angiogenesis.

Generation of a HER2 TIC-enriched Signature (HTICS)

Figure 10:
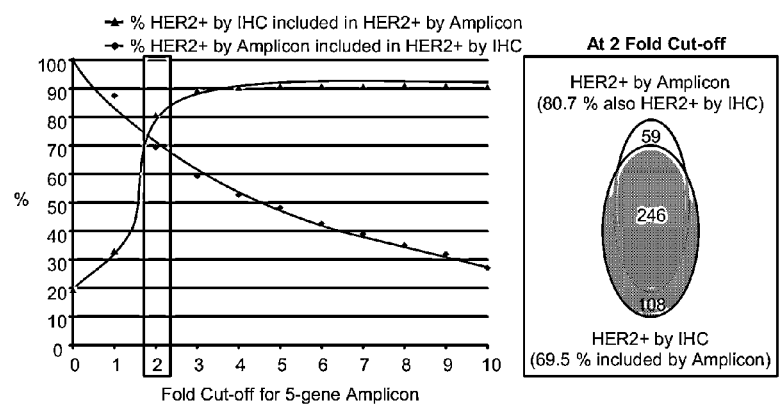
FIG. 10. Comparison of HER2$^+$ patient selection by IHC (Table 1B) versus the 5-gene HER2 amplicon (Table 1C). Samples from 11 published cohorts were combined and the percentage overlap between the two methods of choosing HER2$^+$ patients was calculated at increasing cut-off values of the 5 HER2 gene amplicon (Table 1C: ErbB2, Stard3, Perld1, Grb7, & C17orf37). Left, black line: % of HER2$^+$ patients selected by the amplicon that is also HER2$^+$ based on IHC. Gray line: % of total HER2$^+$ patients selected by IHC included in the selected samples. With higher cut-off, less HER2$^+$ samples are included in the study. Right, optimal percentage is achieved at 2-fold cut-off: 80.7% of selected samples are both HER2$^+$ by amplicon and by IHC, while 69.5% of total HER2$^+$ by IHC samples are included.

To generate a Her2/Neu TIC-enriched prognostic signature we analyzed publicly available cohorts with clinical outcomes and microarray expression data from RNA extracted from fresh tumor biopsies (Table 1A). Since HER2 status as determined by immunostaining was not available for most cohorts, we used 2-fold increase in expression of ≥3 of 5 genes on the HER2 amplicon (HER2/ErbB2, Stard3, Perld1, Grb7, & C17orf37) as the basis to collate HER2$^+$ patients. This criterion, previously used to generate HDPP (23), selected 69.5% of HER2 patients as determined by IHC (FIG. 10).

Figure 4:
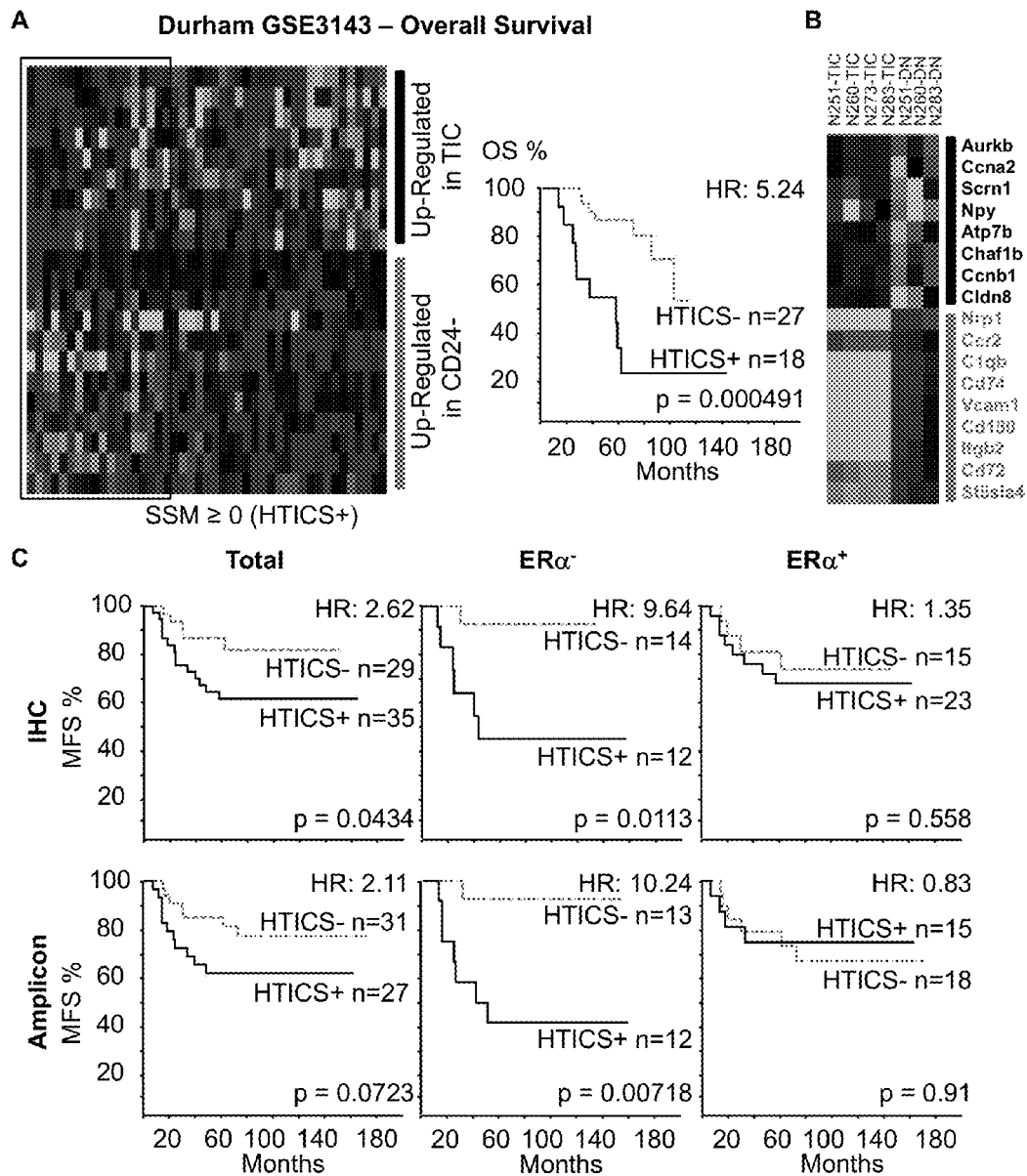
FIG. 4. Generation of a Her2/Neu TIC-enriched prognostic signature (HTICS). (A) Left, gene expression heatmap of 45 $HER2^+$ patients with descending "Score for Signature Match" (SSM) using GSE3143 as a training cohort, with patients who match (solid line) or do not match (dashed line) HTICS. Right, SSM>0 cutoff was selected to evaluate predictive power by Kaplan-Meier analysis. HR, hazard ratio. (B) HTICS differentiates TIC versus non-TIC mammary tumor fractions. The 17-gene HTICS is shown on the right. (C) Metastasis free survival (MFS) curves and HRs using HTICS for $HER2^+$, $HER2^+$:$ERα^-$ and $HER2^+$:$ERα^+$ patients collated from GSE2034 and GSE2603 on the basis of IHC (top) or 5-gene HER2 amplicon (bottom).

We first identified differentially expressed genes (329) that showed ≥2 fold increase or decrease in enriched TIC versus non-TIC fractions with a significant P value (≤0.05). 284 of these genes were found on a human overall survival (OS) cohort (GSE3143), which we used to train the signature. We classified patients using a "Score for Signature Match (SSM)" algorithm, modified from reference (9) (Material and Methods in Example 2). Without training, the 284 genes could separate HER2$^+$ patients in the GSE3143 cohort into poor and good prognosis groups with a hazard ratio (HR) of 2.54 (P=0.072, FIG. 11A). After testing for association and significance of each gene to patient outcome, a 40-gene signature was derived which could stratify patients with HR of 3.53 (P=0.00742, FIG. 11A). Further optimization resulted in a 17 Her2 TIC-enriched Signature, which we termed HTICS. Gene expression heatmap of 45 HER2$^+$ patients with descending SSM scores in the training cohort using HTICS is shown (FIG. 4A, left panel). A SSM>0 cutoff was selected to evaluate its predictive power by Kaplan-Meier analysis. On this training cohort, tumors expressing HTICS had a reduced OS relative to tumors that did not express the signature (HR=5.24; P=0.000491; FIG.

4B). HTICS was specific to HER2$^+$ tumors; its predictive power for all BC subtypes or for HER2-negative tumors was statistically insignificant (FIG. 11B).

HTICS consists of 8 up-regulated (Aurkb, Ccna2, Scrn1, Npy, Atp7b, Chaf1b, Ccnb1, Cldn8) and 9 down-regulated genes (Nrp1, Ccr2, C1qb, Cd74, Vcam1, Cd180, Itgb2, Cd72, St8sia4; FIG. 4B; FIG. 11C). The up-regulated subset includes genes associated with passage through the S/G2/M phase of the cell cycle (Aurkb, cyclinB1, Cyclin A2; Chaf1b). Down-regulated in HTICS are genes involved in cell adhesion, angiogenesis and immune-response.

HTICS Predicts Clinical Outcome for HER2$^+$:ERα$^-$ BC Patients Treated with Chemotherapy We initially evaluated the prognostic power of HTICS using two metastasis-free survival (MFS) cohorts (n=64) with annotated HER2 expression data determined by IHC. HTICS$^+$ patients exhibited poor MFS with HR of 2.62 relative to the HTICS-negative group (P=0.043; FIG. 4C). As MMTV-Neu tumors are ERα-negative, we determined the effect of ERα-expression on the predictive power of HTICS. Remarkably, HTICS predicted 10-year MFS of 83.6% for signature-negative and 46.3% for signature-positive HER2$^+$:ERα$^-$ patients (HR=9.64; P=0.01), and was not predictive for the HER2$^+$:ERα$^+$ group (FIG. 4C, top). Importantly, similar results were obtained when patients from these cohorts were collated on the basis of the 5 gene HER2 amplicon, with MFS of 83.6% and 41.7% for HTICS$^-$ and HTICS$^+$HER2$^+$:ERα$^-$ groups, respectively (HR=10.24; P=0.007; FIG. 4C, bottom).

Figure 5:
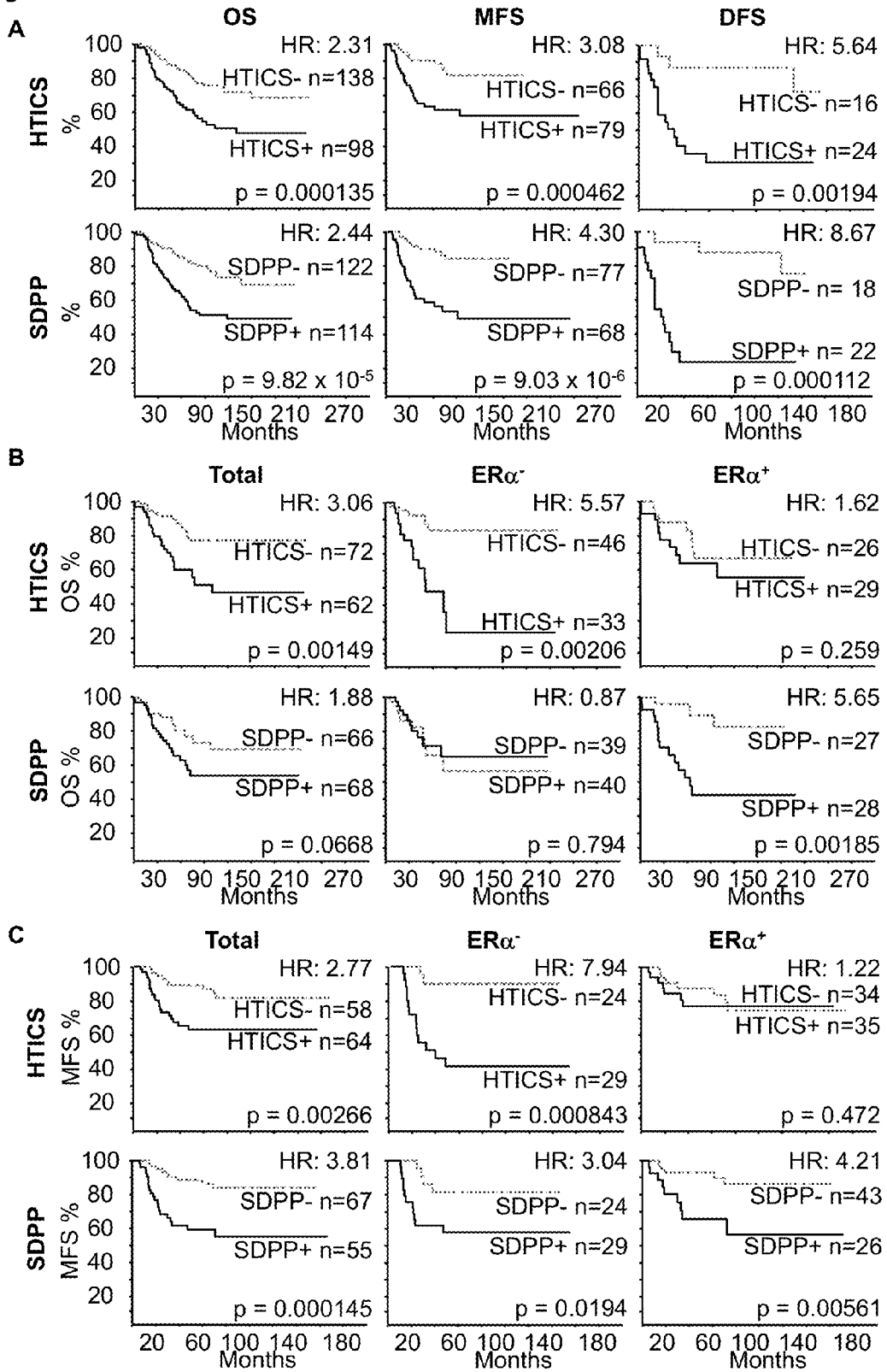
FIG. 5. HTICS predicts clinical outcome for $HER2^+$:$ERα^-$ BC patients treated with chemotherapy; SDPP predicts clinical outcome for $HER2^+$:$ERα^+$ patients. (A) Kaplan-Meier analyses of combined overall survival (OS), metastasis free survival (MFS) or Disease-free survival (DFS) using HTICS or SDPP. (B-C) Kaplan-Meier analyses on OS (B) and MFS (C) cohorts with known ERα status.

Next we extended our analysis to other MFS, OS and DFS cohorts (excluding the training cohort) using the 5-gene HER2 amplicon to identify HER2$^+$ patients. HTICS predicted OS, MFS and DFS for HER2$^+$ patients with HR of 2.1, 3 and 5.6, respectively (P<0.002, FIG. 5A). Moreover, for cohorts with available ERα data, HTICS predicted clinical outcomes for HER2$^+$:ERα$^-$ patients with a 10-year OS of 83.6% versus 24.0% (HR=5.57; P=0.002) and MFS of 90.9% versus 47.2% (H=7.94; P=0.00084)(FIG. 5B-C).

HTICS may identify patients with poor prognosis or poor response to chemotherapy. To address this question, we performed a retrospective analysis on cohorts of patients treated or not with conventional chemotherapy (FIG. 11D). There was a tendency of HER2$^+$ and HER2$^+$:ERα$^+$, but not HER2$^+$:ERα$^-$ patients, to benefit from chemotherapy. HTICS$^-$ HER2$^+$:ERα$^-$ survived better than the HTICS$^+$ HER2$^+$:ERα$^-$ patients both in treated and untreated settings. We note that retrospective analyses may miss subtle benefits that can only be observed in prospective studies. Nonetheless, our signature clearly identifies high-risk HER2$^+$:ERα$^-$ patients with bad prognosis and poor response to conventional chemotherapy.

The tumor suppressor p53 is a transcriptional activator of ERα; mutation in p53 correlates with reduced ERα expression and bad prognosis (24). In a patient cohort with available p53 status (n=32), the predictive power of HTICS was elevated in the p53 mutant arm (HR=5.78, P=0.0136) compared to the whole population (HR=3.4, P=0.028) or the p53 wild type arm (HR=2.34, P=0.414; FIG. 11E), suggesting that this signature can discriminate clinical outcome for HER2$^+$ patients depending not only on ERα but also on p53 status.

Figure 12A:
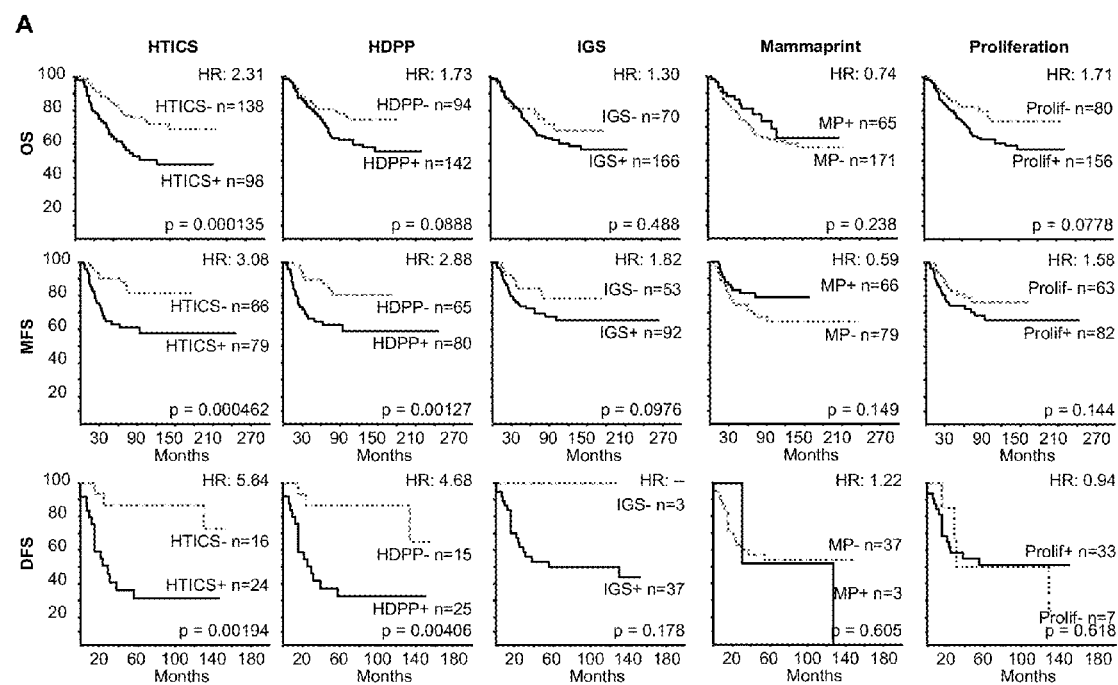
FIG. 12. Predictive powers of HTICS versus HDPP, IGS, MammaPrint and proliferation signatures. (A) OS, MFS and DFS Kaplan-Meier curves of HER2$^+$ patients based on HTICS, HDPP, IGS, MammaPrint and proliferation signature. (B-C) Kaplan-Meier OS (B) and MFS (C) curves of HER2$^+$, HER2$^+$:ERα$^-$ and HER2$^+$:ERα$^+$ patients based on HTICS, HDPP, IGS, MammaPrint and proliferation signature.
Figure 12B:
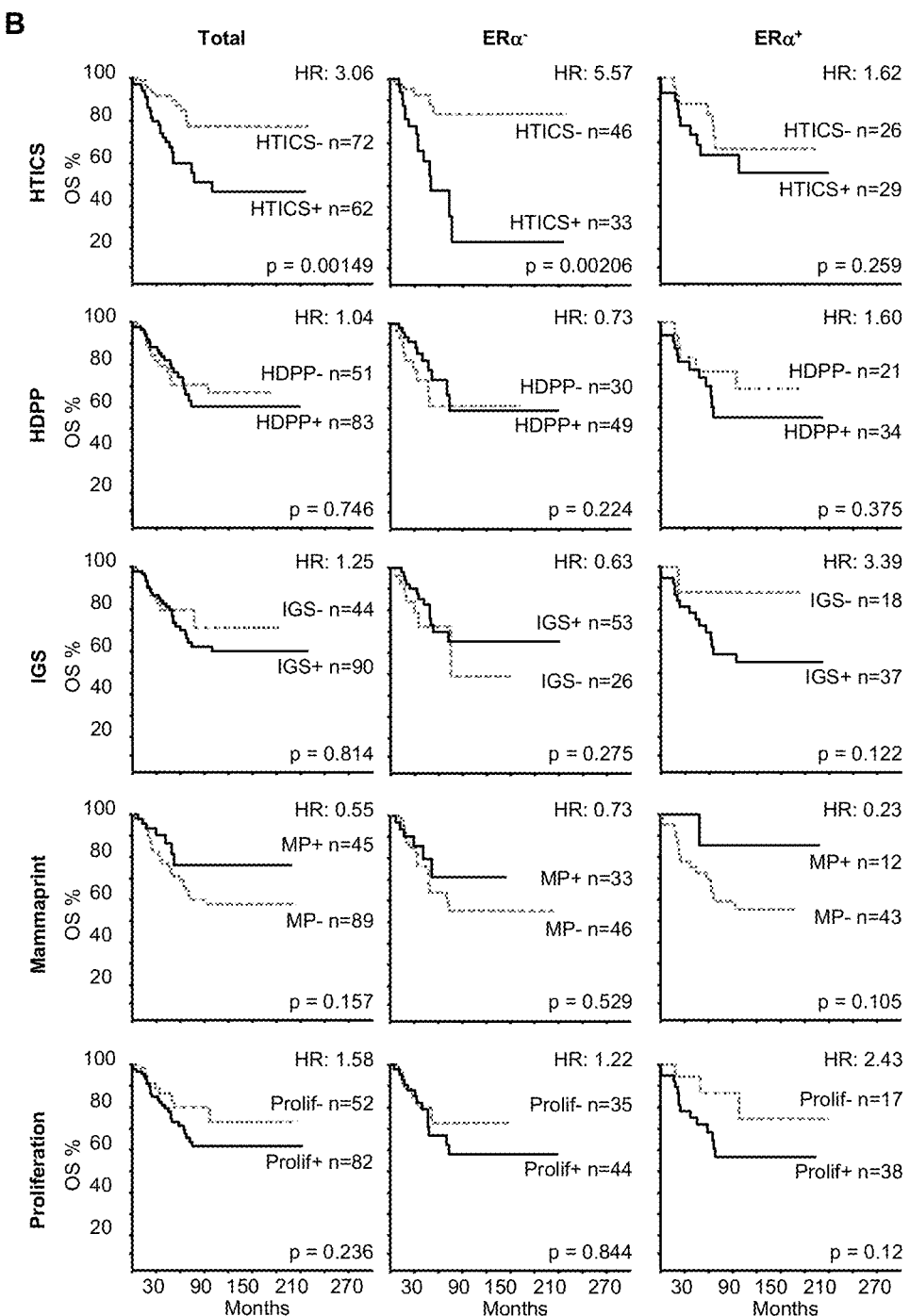
Figure 12C:
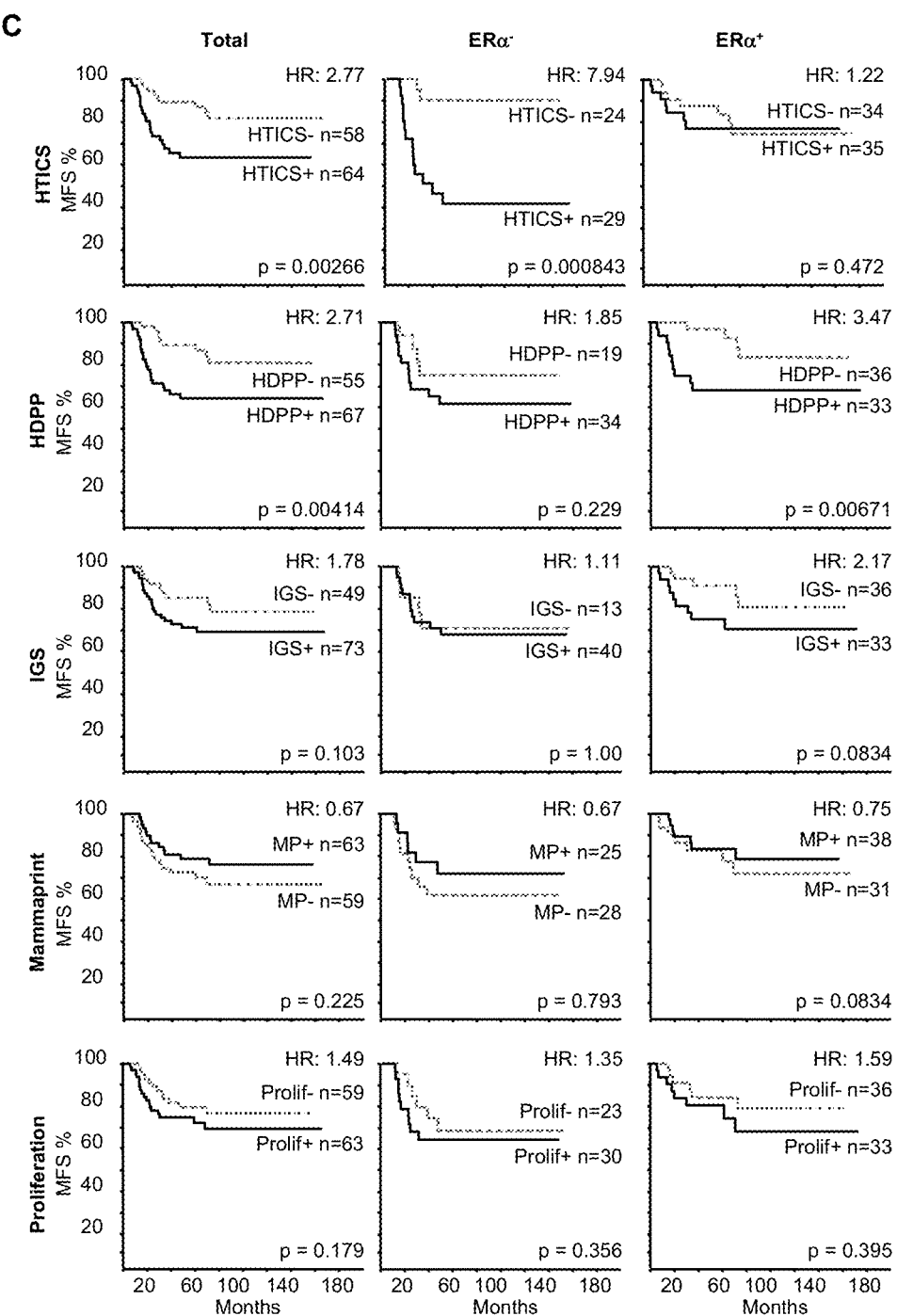

HTICS Predicts Clinical Outcome for HER2$^+$:ERα$^-$ Patients; SDPP for HER2$^+$:ERα$^+$ Next we compared HTICS predictive power to other signatures (Table 1D-H). The stroma-derived prognostic predictor (SDPP; (12)), was highly predictive for HER2$^+$ BC patients (FIG. 5A). This predictive power was proportional to the ERα$^+$ to ERα$^-$ ratio in these cohorts. Indeed, SDPP was not (OS, P=0.794) or only moderately informative (MFS, HR=3.0; P<0.02) for HER2$^+$:ERα$^-$ patients but was highly predictive for HER2$^+$:ERα$^+$ patients with HR=5.65 for OS (P=<0.002) and HR=4.21 (P<0.01) for MFS (FIG. 5B-C). Thus, together HTICS and SDPP can be used to predict clinical outcome for the two HER2$^+$ BC subtypes. For HER2$^+$:ERα$^+$ patients, a HER2-derived prognostic predictor (HDPP) (23), was also predictive for MFS better than HTICS with HR of 3.47 (P<0.007; FIG. 12). In contrast, a 70 gene/mammaPrint (9), IGS (11), and BC proliferation signatures (25) performed poorly on both HER2$^+$:ERα$^+$ and HER2$^+$:ERα$^-$ patients (FIG. 12).

HTICS Predicts Clinical Outcome Independently of Other Predictors Including Node Status Next, we performed bi- and multivariate analyses of HER2$^+$ and HER2$^+$:ERα$^-$ patients to determine the effect, if any, of chemotherapy, tumor grade, tumor size, age at detection and lymph node involvement on the prediction power of HTICS. HTICS was highly predictive independently of these other variables (FIG. 13). The other most potent predictor was lymph node status with HRs of 3.28 and 8.29 in bi- and multivariate analysis of HER2$^+$:ERα$^-$ patients, respectively. In the bivariate analysis, HTICS could further subdivide node$^+$ tumors into high and low risk groups with HR of 5.2 or compounded HR of 3.28× 5.2=17.0.

Figure 6:
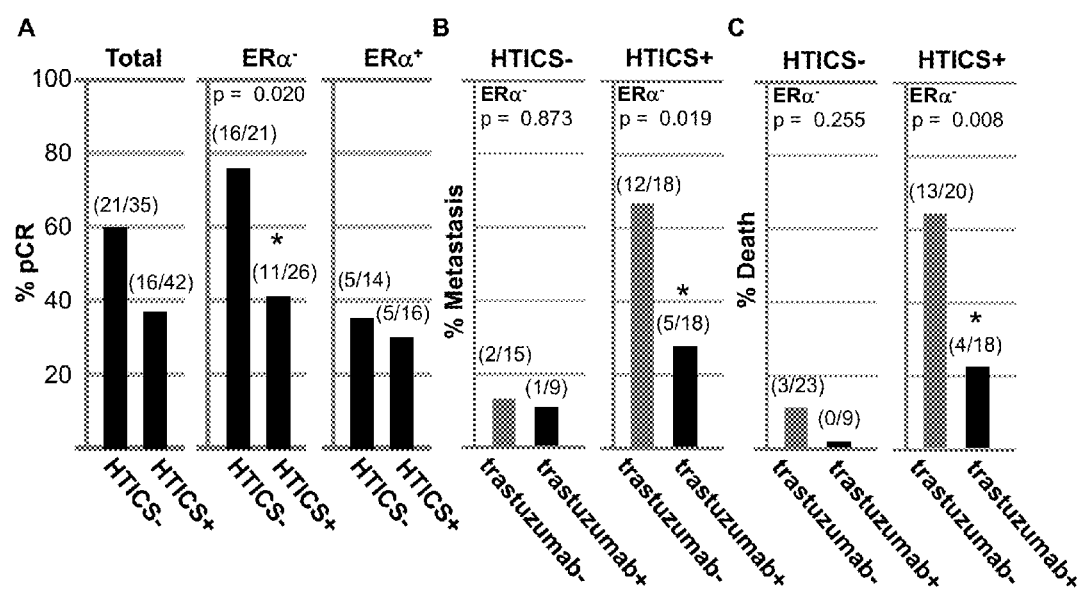
FIG. 6. HTICS predicts response of $HER2^+$:$ERα^-$ BC patients to trastuzumab. (A) Pathological Complete response (pCR) data for $HER2^+$, $HER2^+$:$ERα^-$ and $HER2^+$:$ERα^+$ patients treated with chemotherapy/trastuzumab. (B-C) Fractions of patients that developed metastasis (B) or died (C) 4-years post-surgery in trastuzumab-untreated patients ($trastuzumab^-$) selected from publicly available cohorts (FIG. 5C), versus patients treated with neoadjuvant chemotherapy plus trastuzumab ($trastuzumab^+$).

HTICS Predicts Clinical Outcome for HER2$^+$:ERα$^-$ BC Patients Treated with Neoadjuvant Chemotherapy Plus Trastuzumab The aforementioned results indicate that HTICS$^+$ patients do not respond well to conventional chemotherapy. We next sought to determine their response to trastuzumab. Only one patient cohort (n=27) of neoadjuvant chemotherapy plus trastuzumab with microarray data and pathological complete response (pCR) is publicly available (GSE22358-(26)). We combined it with a new dataset with clinical data (pCR, MFS and OS) from 50 HER2$^+$ patients who were treated with neoadjuvant chemotherapy (fluorouracil/epirubicin or adriamycin/cyclophosphamide-taxol) plus trastuzumab at the MD Anderson Cancer Center and monitored in the past 7.5 years. This group of HER2$^+$ patients included 32 ERα$^-$ and 18 ERα$^+$ tumors. HTICS$^+$ HER2$^+$:ERα$^-$ patients exhibited significantly worse pCR (11/26=42%) relative to the HTICS$^-$ group (16/21=76%; P=0.0195; FIG. 6; FIG. 14A).

Whereas none of the HTICS$^-$ HER2$^+$:ERα$^-$ patients died during this 7.5 year period; all 5 patients who died had HTICS$^+$ tumors. However, due to the small size of the group and relatively short follow-up, the results were not statistically significant (P=0.08; FIG. 14B). Similar trend of poor prognosis was observed for MFS (FIG. 14B).

To begin to assess benefits from trastuzumab, we retrospectively determined the fraction of HER2$^+$:ERα$^-$ patients that developed metastasis within 48 months post-surgery in the publicly available trastuzumab-untreated (n=33, FIG. 5C) versus neoadjuvant chemo/trastuzumab-treated patients (n=27, FIG. 6A). For HTICS$^-$ patients, trastuzumab did not have a significant effect with 2/15 (13%) developing metastasis in the trastuzumab-negative group versus 1/9 (11%) in the chemo plus trastuzumab group (P=0.873; FIG. 6B). In contrast, for HTICS$^+$ patients, 12/18 (66%) relapsed in the chemo group compared to 5/18 (27%) in the chemo/trastuzumab group (FIG. 6B). Despite the caveat of comparing independent patient cohorts, the results were highly significant (P=0.019), indicating that trastuzumab reduced metastasis in HTICS$^+$ HER2$^+$:ERα$^-$ patients 2.4 fold (66%/27%). Similarly, no statistically significant difference in OS was found in trastuzumab-untreated versus chemo/trastuzumab-treated HTICS⁻ HER2⁺:ERα⁻ patients (P=0.255; FIG. 6C). In contrast, for HTICS⁺ patients, 13/20 (65%) died in the untreated compared to 4/18 (22%) in the chemo/trastuzumab treated cohorts (2.95 fold increase in OS; P=0.008). Together these results suggest that HTICS⁺ HER2⁺:ERα⁻ patients benefit from trastuzumab and should be prioritized for anti-HER2 therapy.

Discussion

We report on the generation of a prognostic signature (HTICS) that can identify a high-risk HER2⁺:ERα⁻ BC subgroup, which, in retrospective analysis, resists chemotherapy but responds to chemotherapy plus trastuzumab. The signature was generated based on highly enriched TICs from a mouse model of HER2⁺:ERα⁻ BC. A critical step was to demonstrate by single cell transplantation assays that Her2⁺ TICs are similar and stable, hence analysis of a few primary tumors is broadly informative. As the TIC-enriched fraction contains only a small percentage of TICS (2-4.6%), most cells in this fraction represent early progenitors whose expression pattern likely reflect the proportion of TICs in the tumor. Genes associated with the ability of a single cell to self-renew and form a tumor at an otherwise normal site following transplantation into recipient mice, may also endow it with the ability to form micrometastases at distal sites and acquire the necessary genetic changes needed for full macrometastases in human (27). Indeed, 4 of the 8 up-regulated genes in HTICS are directly involved in cell cycle progression, DNA replication and mitosis. In addition, HTICS includes down-regulated genes involved in immune response; this may allow TICs to evade immune surveillance, enhancing dissemination and metastasis.

In our retrospective analysis, chemo plus trastuzumab treatment improved MFS 2.4 fold and OS 2.9 fold compared to trastuzumab-untreated therapy. Thus, HTICS can identify high-risk patients that may be prioritized for chemo/trastuzumab therapy. This may be particularly relevant to low-income countries where trastuzumab therapy is not publicly available; HTICS⁺ can provide an objective criterion and an incentive for signature-positive patients to undergo trastuzumab therapy. In contrast, the effect of trastuzumab on HTICS⁻ patients was insignificant for both MFS and OS cohorts over a 4-year period. We stress that our results do not justify at this stage withholding trastuzumab therapy from HTICS⁻ patients. A prospective analysis of large cohorts is urgently needed to assess small benefits, if any, of trastuzumab in this group. Clearly, the lack of large, prospective cohorts with clinical outcome and microarray data from RNA derived from fresh tumor biopsies is a major limitation. Large cohorts of formalin fixed, paraffin-embedded BC tissues with clinical outcome are available. NanoString technology can be used to assess gene expression on paraffin-embedded specimens (28),

TABLE 1

| DataSets | Treated | Regiment | Systemic Chemo Therapy |
|---|---|---|---|
| A. Therapeutic Regiments | | | |
| Training | | | |
| GSE3143 | N/A | N/A | N/A |
| OS | | | |
| GSE1456 | Yes | CMF, tamoxifen, goserelin | Yes |
| GSE3494 | Yes | Endocrine Therapy | No |
| GSE7390 | N/A | N/A | No |
| GSE16446 | Yes | Epirubicin | Yes |
| GSE18229 | Yes | Chemotherapy (not specified) | Yes |
| GSE20685 | Yes | CMF, CAF, Taxane | Yes |
| MFS | | | |
| GSE2034 | Yes | Radiotherapy | No |
| GSE2603 | Yes | Radiotherapy | No |
| GSE5327 | N/A | N/A | N/A |
| GSE6532 | Yes | tamoxifen | Yes |
| GSE11121 | Yes | Radiotherapy | No |
| GSE25066 | Yes | taxane-anthracycline | Yes |
| DFS | | | |
| GSE4922 | Yes | Endocrine Therapy | No |
| GSE12093 | Yes | tamoxifen | Yes |

| B. HER2 IHC Status Determination | |
|---|---|
| DataSets | HER2 IHC Method |
| GSE24185 | Positive/Negative |
| GSE22358 | Positive/Negative |
| GSE25066 | Positive/Negative |
| GSE2603 | Positive/Negative |
| GSE2034 | Positive/Negative |
| GSE5460 | Positive/Negative |
| GSE21653 | Positive/Negative |
| GSE26639 | Positive/Negative |
| GSE19697 | Positive/Negative |
| GSE17907 | Positive/Negative |
| GSE16446 | IHC >3 and IHC = 2 with Fish > 3 |
| GSE20194 | IHC >3 and IHC = 2 with Fish > 4 |

TABLE 1-continued

| Gene | Gene Name | RefSeq | |
|---|---|---|---|
| C. HER2 Amplicon | | | |
| HER2 | v-erb-b2 erythroblastic leukemia viral oncogene homolog 2, neuro/glioblastoma derived oncogene homolog (avian) | NM_001005862 | NM_004448 |
| Stard3 | StAR-related lipid transfer (START) domain containing 3 | NM_006804 | |
| Perld1 | per1-like domain containing 1 | NM_033419 | |
| Grb7 | growth factor receptor-bound protein 7 | NM_001030002 | NM_005310 |
| C17orf37 | chromosome 17 open reading frame 37 | NM_032339 | |
| D. HDPP | | | |
| GRB7 | growth factor receptor-bound protein 7 | NM_001030002 | NM_005310 |
| CXCR4 | chemokine (C-X-C motif) receptor 4 | NM_001008540 | NM_003467 |
| PERLD1 | per1-like domain containing 1 | NM_033419 | |
| LAD1 | ladinin 1 | NM_005558 | |
| PLAU | plasminogen activator, urokinase | NM_002658 | |
| SPTBN2 | spectrin, beta, non-erythrocytic 2 | NM_006946 | |
| IRF6 | interferon regulatory factor 6 | NM_006147 | |
| PKP3 | plakophilin 3 | NM_007183 | |
| PXDN | peroxidasin homolog (Drosophila) | NM_012293 | |
| SLK | STE20-like kinase (yeast) | NM_014720 | |
| COL8A1 | collagen, type VIII, alpha 1 | NM_001850 | NM_020351 |
| LTBP1 | latent transforming growth factor beta binding protein 1 | NM_000627 | NM_206943 |
| CD55 | CD55 molecule, decay accelerating factor for complement (Cromer blood group) | NM_000574 | NM_001114752 |
| CASP6 | caspase 6, apoptosis-related cysteine peptidase | NM_001226 | NM_032992 |
| ELMO3 | engulfment and cell motility 3 | NM_024712 | |
| COMP | cartilage oligomeric matrix protein | NM_000095 | |
| DDEF2 | ArfGAP with SH3 domain, ankyrin repeat and PH domain 2 | NM_001135191 | NM_003887 |
| INHBA | inhibin, beta A | NM_002192 | |
| ZNF609 | zinc finger protein 609 | NM_015042 | |
| S100A11 | S100 calcium binding protein A11 | NM_005620 | |
| SH3YL1 | SH3 domain containing, Ysc84-like 1 (S. cerevisiae) | NM_015677 | |
| HSPBP1 | HSPA (heat shock 70 kDa) binding protein, cytoplasmic cochaperone 1 | NM_001130106 | NM_012267 |
| KPNA3 | karyopherin alpha 3 (importin alpha 4) | NM_002267 | |
| ZNF281 | zinc finger protein 281 | NM_012482 | |
| GLRX2 | glutaredoxin 2 | NM_016066 | NM_197962 |
| SENP5 | SUMO1/sentrin specific peptidase 5 | NM_152699 | |
| C12orf29 | chromosome 12 open reading frame 29 | NM_001009894 | |
| C7orf25 | chromosome 7 open reading frame 25 | NM_001099858 | NM_024054 |
| LPGAT1 | lysophosphatidylglycerol acyltransferase 1 | NM_014873 | |
| PEX11B | peroxisomal biogenesis factor 11 beta | NM_003846 | |
| UBE2G1 | ubiquitin-conjugating enzyme E2G 1 (UBC7 homolog, yeast) | NM_003342 | |
| MTHFR | 5,10-methylenetetrahydrofolate reductase (NADPH) | NM_005957 | |
| TCF7 | transcription factor 7 (T-cell specific, HMG-box) | NM_001134851 | NM_001134852 |
| AFP | alpha-fetoprotein | NM_001134 | |
| PRKCA | protein kinase C, alpha | NM_002737 | |
| FAIM3 | Fas apoptotic inhibitory molecule 3 | NM_001142472 | NM_001142473 |
| SNF1LK2 | salt-inducible kinase 2 | NM_015191 | |
| RAC2 | ras-related C3 botulinum toxin substrate 2 (rho family, small GTP binding protein Rac2) | NM_002872 | |
| FLNC | filamin C, gamma (actin binding protein 280) | NM_001127487 | NM_001458 |
| GYPC | glycophorin C (Gerbich blood group) | NM_002101 | NM_016815 |
| GAS7 | growth arrest-specific 7 | NM_001130831 | NM_003644 |
| GLTSCR1 | glioma tumor suppressor candidate region gene 1 | NM_015711 | |
| ADD3 | adducin 3 (gamma) | NM_001121 | NM_016824 |
| PTPRCAP | protein tyrosine phosphatase, receptor type, C-associated protein | NM_005608 | |
| CD3D | CD3d molecule, delta (CD3-TCR complex) | NM_000732 | NM_001040651 |
| ABCD4 | ATP-binding cassette, sub-family D (ALD), member 4 | NM_005050 | NR_003256 |
| SEMA6A | MRNA, clone: FBR89, from chromosome 5q21-q22 | NM_020796 | |
| KLF9 | Kruppel-like factor 9 | NM_001206 | |
| CYorf15B | chromosome Y open reading frame 15B | NM_032576 | |
| LTBP4 | latent transforming growth factor beta binding protein 4 | NM_001042544 | NM_001042545 |
| CLCN7 | chloride channel 7 | NM_001114331 | NM_001287 |
| KIRREL | kin of IRRE like (Drosophila) | NM_018240 | |
| ST3GAL2 | ST3 beta-galactoside alpha-2,3-sialyltransferase 2 | NM_006927 | |
| CDON | Cdon homolog (mouse) | NM_016952 | |
| MAP4 | microtubule-associated protein 4 | NM_001134364 | NM_001134365 |
| FYN | P59fyn(T) = OKT3-induced calcium influx regulator [human, Jurkat J6 T cell line, mRNA Partial, 1605 nt] | NM_002037 | NM_153047 |
| CD69 | CD69 molecule | NM_001781 | |
| ITGA4 | integrin, alpha 4 (antigen CD49D, alpha 4 subunit of VLA-4 receptor) | NM_000885 | |
| C11orf57 | chromosome 11 open reading frame 57 | NM_001082969 | NM_001082970 |
| EPB41 | erythrocyte membrane protein band 4.1 (elliptocytosis 1, RH-linked) | NM_004437 | NM_203342 |

TABLE 1-continued

| | | | |
|---|---|---|---|
| SFRS5 | splicing factor, arginine/serine-rich 5 | NM_001039465 | NM_006925 |
| PRSS12 | protease, serine, 12 (neurotrypsin, motopsin) | NM_003619 | |
| SDPR | serum deprivation response (phosphatidylserine binding protein) | NM_004657 | |
| ETS1 | v-ets erythroblastosis virus E26 oncogene homolog 1 (avian) | NM_001143820 | NM_005238 |
| SLC25A42 | Hypothetical protein MGC26694, mRNA (cDNA clone IMAGE: 5302893) | NM_178526 | |
| BMP4 | bone morphogenetic protein 4 | NM_001202 | NM_130850 |
| ZAP70 | zeta-chain (TCR) associated protein kinase 70 kDa | NM_001079 | NM_207519 |
| PELI2 | pellino homolog 2 (Drosophila) | NM_021255 | |
| GPX3 | glutathione peroxidase 3 (plasma) | NM_002084 | |
| PDE2A | phosphodiesterase 2A, cGMP-stimulated | NM_001143839 | NM_002599 |
| NDN | necdin homolog (mouse) | NM_002487 | |
| PPP5C | protein phosphatase 5, catalytic subunit | NM_006247 | |
| EDNRB | endothelin receptor type B | NM_000115 | NM_001122659 |
| ARIH2 | TRIAD1 mRNA, 3' untranslated region | NM_006321 | |
| TMEFF1 | transmembrane protein with EGF-like and two follistatin-like domains 1 | NM_003692 | |
| TLE4 | transducin-like enhancer of split 4 (E(sp1) homolog, Drosophila) | NM_007005 | |
| DPYSL2 | dihydropyrimidinase-like 2 | NM_001386 | |
| C17orf68 | chromosome 17 open reading frame 68 | NM_025099 | |
| STXBP1 | syntaxin binding protein 1 | NM_001032221 | NM_003165 |
| SH3BP5 | SH3-domain binding protein 5 (BTK-associated) | NM_001018009 | NM_004844 |
| CLSTN3 | calsyntenin 3 | NM_014718 | |
| RASIP1 | Ras interacting protein 1 | NM_017805 | |
| FAM46A | family with sequence similarity 46, member A | NM_017633 | |
| PIM1 | pim-1 oncogene | NM_002648 | |
| ARHGAP19 | Rho GTPase activating protein 19 | NM_032900 | |
| OSBPL3 | oxysterol binding protein-like 3 | NM_015550 | NM_145320 |
| COLEC12 | collectin sub-family member 12 | NM_130386 | |
| ITM2A | integral membrane protein 2A | NM_004867 | |
| FGF2 | fibroblast growth factor 2 (basic) | NM_002006 | |
| HMHA1 | histocompatibility (minor) HA-1 | NM_012292 | |
| PLAC8 | placenta-specific 8 | NM_001130715 | NM_001130716 |
| SLC16A7 | solute carrier family 16, member 7 (monocarboxylic acid transporter 2) | NM_004731 | |
| MAP7D3 | MAP7 domain containing 3 | NM_024597 | |
| ATP8B2 | ATPase, class I, type 8B, member 2 | NM_001005855 | NM_020452 |
| SOCS1 | suppressor of cytokine signaling 1 | NM_003745 | |
| CX3CR1 | chemokine (C-X3-C motif) receptor 1 | NM_001337 | |
| TGFBR3 | transforming growth factor, beta receptor III | NM_003243 | |
| WDHD1 | WD repeat and HMG-box DNA binding protein 1 | NM_001008396 | NM_007086 |
| STAT5A | signal transducer and activator of transcription 5A | NM_003152 | |
| MLXIPL | MLX interacting protein-like | NM_032951 | NM_032952 |
| CRMP1 | collapsin response mediator protein 1 | NM_001014809 | NM_001313 |
| SNCA | synuclein, alpha (non A4 component of amyloid precursor) | NM_000345 | NM_007308 |
| SEMA7A | semaphorin 7A, GPI membrane anchor (John Milton Hagen blood group) | NM_003612 | |
| RBP4 | retinol binding protein 4, plasma | NM_006744 | |
| DMN | synemin, intermediate filament protein | NM_015286 | NM_145728 |
| TF | transferrin | NM_001063 | |
| ANPEP | alanyl (membrane) aminopeptidase | NM_001150 | |
| ALAS2 | aminolevulinate, delta-, synthase 2 | NM_000032 | NM_001037967 |
| TSPAN7 | tetraspanin 7 | NM_004615 | |
| GPC3 | glypican 3 | NM_004484 | |
| S100B | S100 calcium binding protein B | NM_006272 | |
| SOX10 | SRY (sex determining region Y)-box 10 | NM_006941 | |
| E. IGS | | | |
| CLTC | clathrin, heavy chain (Hc) | NM_004859 | |
| LDHA | lactate dehydrogenase A | NM_001135239 | NM_005566 |
| PGK1 | phosphoglycerate kinase 1 | NM_000291 | |
| SSR1 | signal sequence receptor, alpha | NM_003144 | |
| COPB2 | coatomer protein complex, subunit beta 2 (beta prime) | NM_004766 | NR_023350 |
| PLP2 | proteolipid protein 2 (colonic epithelium-enriched) | NM_002668 | |
| RAD23B | RAD23 homolog B (S. cerevisiae) | NM_002874 | |
| PSMA5 | proteasome (prosome, macropain) subunit, alpha type, 5 | NM_002790 | |
| ICMT | isoprenylcysteine carboxyl methyltransferase | NM_012405 | |
| DPF2 | D4, zinc and double PHD fingers family 2 | NM_006268 | |
| JTV1 | JTV1 gene | NM_006303 | |
| CSTF1 | cleavage stimulation factor, 3' pre-RNA, subunit 1, 50 kDa | NM_001033521 | NM_001033522 |
| GNPDA1 | glucosamine-6-phosphate deaminase 1 | NM_005471 | |
| NSF | N-ethylmaleimide-sensitive factor | NM_006178 | |
| MAPK14 | mitogen-activated protein kinase 14 | NM_001315 | NM_139012 |
| STK39 | serine threonine kinase 39 (STE20/SPS1 homolog, yeast) | NM_013233 | |
| RNF8 | ring finger protein 8 | NM_003958 | NM_183078 |
| HS2ST1 | heparan sulfate 2-O-sulfotransferase 1 | NM_001134492 | NM_012262 |
| CNOT4 | CCR4-NOT transcription complex, subunit 4 | NM_001008225 | NM_013316 |
| STAM | signal transducing adaptor molecule (SH3 domain and ITAM motif) 1 | NM_003473 | |

TABLE 1-continued

| | | | |
|---|---|---|---|
| SRP54 | signal recognition particle 54 kDa | NM_003136 | |
| ELP4 | elongation protein 4 homolog (S. cerevisiae) | NM_019040 | |
| KDELR3 | KDEL (Lys-Asp-Glu-Leu) endoplasmic reticulum protein retention receptor 3 | NM_006855 | NM_016657 |
| KLHL20 | kelch-like 20 (Drosophila) | NM_014458 | |
| THEM2 | thioesterase superfamily member 2 | NM_018473 | |
| AMMECR1 | Alport syndrome, mental retardation, midface hypoplasia and elliptocytosis chromosomal region gene 1 | NM_001025580 | NM_015365 |
| AGPS | alkylglycerone phosphate synthase | NM_003659 | |
| ATXN3 | ataxin 3 | NM_001127696 | NM_001127697 |
| PAK2 | p21 protein (Cdc42/Rac)-activated kinase 2 | NM_002577 | |
| CSNK2A1 | casein kinase 2, alpha 1 polypeptide | NM_001895 | NM_177559 |
| CASP8 | caspase 8, apoptosis-related cysteine peptidase | NM_001080124 | NM_001080125 |
| ATIC | 5-aminoimidazole-4-carboxamide ribonucleotide formyltransferase/IMP cyclohydrolase | NM_004044 | |
| TUBB | tubulin, beta | NM_178014 | |
| EIF4E2 | eukaryotic translation initiation factor 4E family member 2 | NM_004846 | |
| PLAA | phospholipase A2-activating protein | NM_001031689 | NM_004253 |
| GSK3B | glycogen synthase kinase 3 beta | NM_002093 | |
| ARPC5 | actin related protein 2/3 complex, subunit 5, 16 kDa | NM_005717 | |
| DNAJC13 | DnaJ (Hsp40) homolog, subfamily C, member 13 | NM_015268 | |
| PDE8A | phosphodiesterase 8A | NM_002605 | NM_173454 |
| GAPDH | glyceraldehyde-3-phosphate dehydrogenase | NM_002046 | |
| SNX6 | sorting nexin 6 | NM_021249 | NM_152233 |
| NOL8 | nucleolar protein 8 | NM_017948 | NR_024020 |
| GTF3C3 | general transcription factor IIIC, polypeptide 3, 102 kDa | NM_012086 | |
| DNMT3A | DNA (cytosine-5-)-methyltransferase 3 alpha | NM_022552 | NM_153759 |
| NUP37 | nucleoporin 37 kDa | NM_024057 | |
| SCNM1 | sodium channel modifier 1 | NM_024041 | XM_001721083 |
| DBR1 | debranching enzyme homolog 1 (S. cerevisiae) | NM_016216 | |
| RAB23 | RAB23, member RAS oncogene family | NM_016277 | NM_183227 |
| C7orf25 | chromosome 7 open reading frame 25 | NM_001099858 | NM_024054 |
| C10orf7 | cell division cycle 123 homolog (S. cerevisiae) | NM_006023 | |
| ISGF3G | interferon regulatory factor 9 | NM_006084 | |
| CAP350 | centrosomal protein 350 kDa | NM_014810 | |
| ALKBH | alkB, alkylation repair homolog 1 (E. coli) | NM_006020 | |
| DKFZP564K0822 | EGFR-coamplified and overexpressed protein | NM_030796 | |
| HAN11 | WD repeat domain 68 | NM_005828 | |
| KIAA0436 | prolyl endopeptidase-like | NM_001042385 | NM_001042386 |
| AFURS1 | ATPase type 13A3 | NM_024524 | |
| PNAS-4 | family with sequence similarity 152, member A | NM_016076 | |
| KIAA0276 | DCN1, defective in cullin neddylation 1, domain containing 4 (S. cerevisiae) | NM_001040402 | NM_015115 |
| KIAA0052 | Superkiller viralicidic activity 2-like 2 (S. cerevisiae) (SKIV2L2), mRNA | NM_015360 | |
| DNAPTP6 | viral DNA polymerase-transactivated protein 6 | NM_001100422 | NM_001100423 |
| NUCKS | nuclear casein kinase and cyclin-dependent kinase substrate 1 | NM_022731 | |
| FLJ10774 | N-acetyltransferase 10 (GCN5-related) | NM_024662 | |
| C16orf33 | small nuclear ribonucleoprotein 25 kDa (U11/U12) | NM_024571 | |
| FLJ10587 | chromosome 17 open reading frame 71 | NM_018149 | |
| HSPC163 | cornichon homolog 4 (Drosophila) | NM_014184 | |
| FLJ20530 | integrator complex subunit 8 | NM_017864 | |
| ETAA16 | Ewing tumor-associated antigen 1 | NM_019002 | |
| FLJ12439 | chromosome 1 open reading frame 163 | NM_023077 | |
| FLJ12806 | axin interactor, dorsalization associated | NM_022831 | |
| C11orf17 | chromosome 11 open reading frame 17 /// NUAK family, SNF1-like kinase, 2 | NM_020642 | NM_030952 |
| METTL2 | methyltransferase like 2A /// methyltransferase like 2B | NM_001005372 | NM_018396 |
| DNAJB1 | DnaJ (Hsp40) homolog, subfamily B, member 1 | NM_006145 | |
| CIRBP | cold inducible RNA binding protein | NM_001280 | NR_023312 |
| CD59 | CD59 molecule, complement regulatory protein | NM_000611 | NM_001127223 |
| LRPAP1 | low density lipoprotein receptor-related protein associated protein 1 | NM_002337 | |
| SH3BGRL | SH3 domain binding glutamic acid-rich protein like | NM_003022 | |
| EMP1 | epithelial membrane protein 1 | NM_001423 | |
| SNRPN | small nuclear ribonucleoprotein polypeptide N /// SNRPN upstream reading frame | NM_003097 | NM_005678 |
| SFPQ | splicing factor proline/glutamine-rich (polypyrimidine tract binding protein associated) | NM_005066 | |
| TPD52 | tumor protein D52 | NM_001025252 | NM_001025253 |
| LTF | lactotransferrin | NM_002343 | |
| MGP | matrix Gla protein | NM_000900 | |
| KLF10 | Kruppel-like factor 10 | NM_001032282 | NM_005655 |
| STC2 | stanniocalcin 2 | NM_003714 | |
| BCL2 | B-cell CLL/lymphoma 2 | NM_000633 | NM_000657 |
| WFDC2 | WAP four-disulfide core domain 2 | NM_006103 | |
| MAPT | microtubule-associated protein tau | NM_001123066 | NM_001123067 |
| NEBL | nebulette | NM_006393 | NM_213569 |
| CEBPD | CCAAT/enhancer binding protein (C/EBP), delta | NM_005195 | |
| HNMT | histamine N-methyltransferase | NM_001024074 | NM_001024075 |

TABLE 1-continued

| | | | |
|---|---|---|---|
| MMP7 | matrix metallopeptidase 7 (matrilysin, uterine) | NM_002423 | |
| MLF1 | myeloid leukemia factor 1 | NM_001130156 | NM_001130157 |
| MAFF | v-maf musculoaponeurotic fibrosarcoma oncogene homolog F (avian) | NM_012323 | NM_152878 |
| GTPBP1 | GTP binding protein 1 | NM_004286 | |
| ZBTB20 | zinc finger and BTB domain containing 20 | NM_015642 | |
| SCGN | secretagogin, EF-hand calcium binding protein | NM_006998 | |
| LRP2 | low density lipoprotein-related protein 2 | NM_004525 | |
| ERBB4 | v-erb-a erythroblastic leukemia viral oncogene homolog 4 (avian) | NM_001042599 | NM_005235 |
| ERN1 | endoplasmic reticulum to nucleus signaling 1 | NM_001433 | |
| NDEL1 | nudE nuclear distribution gene E homolog (*A. nidulans*)-like 1 | NM_001025579 | NM_030808 |
| PRSS16 | protease, serine, 16 (thymus) | NM_005865 | |
| APLP2 | amyloid beta (A4) precursor-like protein 2 | NM_001142276 | NM_001142277 |
| FLNB | filamin B, beta (actin binding protein 278) | NM_001457 | |
| GABARAPL1 | GABA(A) receptor-associated protein like 1 | NM_031412 | |
| SWAP70 | SWAP-70 protein | NM_015055 | |
| CXCL2 | chemokine (C-X-C motif) ligand 2 | NM_002089 | |
| HSPA2 | heat shock 70 kDa protein 2 | NM_021979 | |
| KIAA0146 | KIAA0146 | NM_001080394 | |
| WEE1 | WEE1 homolog (*S. pombe*) | NM_003390 | |
| AIM1 | absent in melanoma 1 | NM_001624 | |
| ELL2 | elongation factor, RNA polymerase II, 2 | NM_012081 | |
| ETS1 | v-ets erythroblastosis virus E26 oncogene homolog 1 (avian) | NM_001143820 | NM_005238 |
| DUSP10 | dual specificity phosphatase 10 | NM_007207 | NM_144728 |
| LARS | leucyl-tRNA synthetase | NM_020117 | |
| FAM53C | family with sequence similarity 53, member C | NM_001135647 | NM_016605 |
| ECHDC2 | enoyl Coenzyme A hydratase domain containing 2 | NM_018281 | |
| IER5 | immediate early response 5 | NM_016545 | |
| ETNK1 | ethanolamine kinase 1 | NM_001039481 | NM_018638 |
| PILRB | paired immunoglobin-like type 2 receptor beta | NM_013440 | NM_175047 |
| TOB2 | transducer of ERBB2, 2 | NM_016272 | |
| CHPT1 | Cholinephosphotransferase | NM_020244 | |
| MAST4 | KIAA0303 gene | NM_015183 | NM_198828 |
| PBP | phosphatidylethanolamine binding protein 1 | NM_002567 | |
| DKFZP586A0522 | methyltransferase like 7A | NM_014033 | |
| VIL2 | ezrin | NM_001111077 | NM_003379 |
| GOLGIN-67 | golgi autoantigen, golgin subfamily a, 8A | NM_181077 | XM_001714558 |
| C5orf18 | receptor accessory protein 5 | NM_005669 | |
| NPD014 | chromosome 1 open reading frame 63 | NM_020317 | |
| CG018 | BRCA2 region, mRNA sequence CG018 | NM_001079691 | NM_052818 |
| DKFZP564D172 | family with sequence similarity 172, member A | NM_032042 | |
| DHRS4 | dehydrogenase/reductase (SDR family) member 4 /// dehydrogenase/reductase (SDR family) member 4 like 2 | NM_021004 | NM_198083 |
| DHRS6 | 3-hydroxybutyrate dehydrogenase, type 2 | NM_020139 | |
| B7-H4 | V-set domain containing T cell activation inhibitor 1 | NM_024626 | |
| 40610 | membrane-associated ring finger (C3HC4) 8 | NM_001002265 | NM_001002266 |
| CDW92 | solute carrier family 44, member 1 | NM_080546 | |
| F. Proliferation | | | |
| Birc5 | baculoviral IAP repeat-containing 5 | NM_001012270 | NM_001012271 |
| aurkb | aurora kinase B | NM_004217 | |
| cdc6 | cell division cycle 6 homolog (*S. cerevisiae*) | NM_001254 | |
| cks2 | CDC28 protein kinase regulatory subunit 2 | NM_001827 | |
| traip | TRAF interacting protein | NM_005879 | |
| chek1 | CHK1 checkpoint homolog (*S. pombe*) | NM_001114121 | NM_001114122 |
| pttg1 | pituitary tumor-transforming 1 | NM_004219 | |
| dnmt1 | DNA (cytosine-5-)-methyltransferase 1 | NM_001130823 | NM_001379 |
| nasp | nuclear autoantigenic sperm protein (histone-binding) | NM_002482 | NM_152298 |
| ung | uracil-DNA glycosylase | NM_003362 | NM_080911 |
| cdc7 | cell division cycle 7 homolog (*S. cerevisiae*) | NM_001134419 | NM_001134420 |
| fen1 | flap structure-specific endonuclease 1 | NM_004111 | |
| mcm3 | minichromosome maintenance complex component 3 | NM_002388 | |
| mcm4 | minichromosome maintenance complex component 4 | NM_005914 | NM_182746 |
| mcm5 | minichromosome maintenance complex component 5 | NM_006739 | |
| mcm6 | minichromosome maintenance complex component 6 | NM_005915 | |
| orc1l | origin recognition complex, subunit 1-like (yeast) | NM_004153 | |
| pcna | proliferating cell nuclear antigen | NM_002592 | NM_182649 |
| prim1 | primase, DNA, polypeptide 1 (49 kDa) | NM_000946 | |
| rfc1 | replication factor C (activator 1) 1, 145 kDa | NM_002913 | |
| rrm1 | ribonucleotide reductase M1 | NM_001033 | |
| rrm2 | ribonucleotide reductase M2 polypeptide | NM_001034 | |
| top2a | topoisomerase (DNA) II alpha 170 kDa | NM_001067 | |
| mad2l1 | MAD2 mitotic arrest deficient-like 1 (yeast) | NM_002358 | |
| cenpe | centromere protein E, 312 kDa | NM_001813 | |
| bub1 | budding uninhibited by benzimidazoles 1 homolog (yeast) | NM_004336 | |
| ctps | CTP synthase | NM_001905 | |
| dhfr | dihydrofolate reductase | NM_000791 | |
| tyms | thymidylate synthetase | NM_001071 | |
| ccna2 | cyclin A2 | NM_001237 | |

TABLE 1-continued

| | | | |
|---|---|---|---|
| ccnb1 | cyclin B1 | NM_031966 | |
| ccne1 | cyclin E1 | NM_001238 | NM_057182 |
| ccnf | cyclin F | NM_001761 | |
| cdc20 | cell division cycle 20 homolog (*S. cerevisiae*) | NM_001255 | |
| ddx11 | DEAD/H (Asp-Glu-Ala-Asp/His) box polypeptide 11 (CHL1-like helicase homolog, *S. cerevisiae*) | NM_004399 | NM_030653 |
| e2f3 | E2F transcription factor 3 | NM_001949 | |
| mki67 | antigen identified by monoclonal antibody Ki-67 | NM_002417 | |
| pkmyt1 | protein kinase, membrane associated tyrosine/threonine 1 | NM_004203 | NM_182687 |
| plk1 | polo-like kinase 1 (*Drosophila*) | NM_005030 | |
| timp1 | TIMP metallopeptidase inhibitor 1 | NM_003254 | |
| cdc25c | cell division cycle 25 homolog C (*S. pombe*) | NM_001790 | NM_022809 |
| cenpf | centromere protein F, 350/400ka (mitosin) | NM_016343 | |
| mapk13 | mitogen-activated protein kinase 13 | NM_002754 | |
| exosc9 | exosome component 9 | NM_001034194 | NM_005033 |
| myb | v-myb myeloblastosis viral oncogene homolog (avian) | NM_001130172 | NM_001130173 |

G. SDPP

| | | | |
|---|---|---|---|
| GZMA | granzyme A (granzyme 1, cytotoxic T-lymphocyte-associated serine esterase 3) | NM_006144 | |
| CD8A | CD8a molecule | NM_001768 | NM_171827 |
| CD52 | CD52 molecule | NM_001803 | |
| CD247 | CD247 molecule | NM_000734 | NM_198053 |
| CD48 | CD48 molecule | NM_001778 | |
| PLEK | pleckstrin | NM_002664 | |
| RUNX3 | runt-related transcription factor 3 | NM_001031680 | NM_004350 |
| GIMAP5 | GTPase, IMAP family member 5 | NM_018384 | |
| LCP1 | lymphocyte cytosolic protein 1 (L-plastin) | NM_002298 | |
| F2RL2 | coagulation factor II (thrombin) receptor-like 2 | NM_004101 | |
| SLC40A1 | solute carrier family 40 (iron-regulated transporter), member 1 | NM_014585 | |
| FRZB | frizzled-related protein | NM_001463 | |
| RAI2 | retinoic acid induced 2 | NM_021785 | |
| HOXA10 | homeobox A10 | NM_018951 | NM_153715 |
| ITGBL1 | Osteoblast specific cysteine-rich protein | NM_004791 | |
| OGN | osteoglycin | NM_014057 | NM_024416 |
| C21ORF34 | chromosome 21 open reading frame 34 | NM_001005732 | NM_001005733 |
| ADRA2A | adrenergic, alpha-2A-, receptor | NM_000681 | |
| CXCL14 | chemokine (C-X-C motif) ligand 14 | NM_004887 | |
| SPP1 | OPN-a | NM_000582 | NM_001040058 |
| HRASLS | HRAS-like suppressor | NM_020386 | |
| VGLL1 | vestigial like 1 (*Drosophila*) | NM_016267 | |
| ADM | adrenomedullin | NM_001124 | |
| C6ORF168 | chromosome 6 open reading frame 168 | NM_032511 | |
| SNTG2 | syntrophin, gamma 2 | NM_018968 | |

H. Mammaprint

| | | | |
|---|---|---|---|
| ALDH4A1 | aldehyde dehydrogenase 4 family, member A1 | NM_003748 | NM_170726 |
| FGF18 | fibroblast growth factor 18 | NM_003862 | |
| LOC100131053 | hypothetical LOC100131053 | XM_001720101 | XM_001722035 |
| BBC3 | BCL2 binding component 3 | NM_001127240 | NM_001127241 |
| EBF4 | early B-cell factor 4 | NM_001110514 | XM_001713721 |
| SCUBE2 | signal peptide, CUB domain, EGF-like 2 | NM_020974 | |
| RUNDC1 | RUN domain containing 1 | NM_173079 | |
| WISP1 | WNT1 inducible signaling pathway protein 1 | NM_003882 | NM_080838 |
| GSTM3 | glutathione S-transferase mu 3 (brain) | NM_000849 | NR_024537 |
| ZNF385B | zinc finger protein 385B | NM_001113397 | NM_001113398 |
| RTN4RL1 | reticulon 4 receptor-like 1 | NM_178568 | |
| PECI | peroxisomal D3,D2-enoyl-CoA isomerase | NM_006117 | NM_206836 |
| TGFB3 | transforming growth factor, beta 3 | NM_003239 | |
| STK32B | serine/threonine kinase 32B | NM_018401 | |
| MS4A7 | membrane-spanning 4-domains, subfamily A, member 7 | NM_021201 | NM_206938 |
| AP2B1 | adaptor-related protein complex 2, beta 1 subunit | NM_001030006 | NM_001282 |
| DHX58 | DEXH (Asp-Glu-X-His) box polypeptide 58 | NM_024119 | |
| C20orf46 | chromosome 20 open reading frame 46 | NM_018354 | |
| ESM1 | endothelial cell-specific molecule 1 | NM_001135604 | NM_007036 |
| CCNE2 | cyclin E2 | NM_057749 | |
| Egln1 | egl nine homolog 1 (*C. elegans*) | NM_022051 | |
| CENPA | centromere protein A | NM_001042426 | NM_001809 |
| LIN9 | lin-9 homolog (*C. elegans*) | NM_173083 | |
| PRC1 | protein regulator of cytokinesis 1 | NM_003981 | NM_199413 |
| PALM2-AKAP2 | PALM2-AKAP2 readthrough transcript | NM_007203 | NM_147150 |
| NMU | neuromedin U | NM_006681 | |
| IGFBP5 | insulin-like growth factor binding protein 5 | NM_000599 | |
| PITRM1 | pitrilysin metallopeptidase 1 | NM_014889 | |
| HRASLS | HRAS-like suppressor | NM_020386 | |
| TMEFF1 | transmembrane protein with EGF-like and two follistatin-like domains 1 | NM_003692 | |
| MCM6 | minichromosome maintenance complex component 6 | NM_005915 | |
| RECQL5 | RecQ protein-like 5 | NM_001003715 | NM_001003716 |
| CDCA7 | cell division cycle associated 7 | NM_031942 | NM_145810 |

TABLE 1-continued

| | | | |
|---|---|---|---|
| RFC4 | replication factor C (activator 1) 4, 37 kDa | NM_002916 | NM_181573 |
| ORC6L | origin recognition complex, subunit 6 like (yeast) | NM_014321 | |
| SLC2A3 | solute carrier family 2 (facilitated glucose transporter), member 3 | NM_006931 | |
| GPR126 | G protein-coupled receptor 126 | NM_001032394 | NM_001032395 |
| FBXO31 | F-box protein 31 | NM_024735 | NR_024568 |
| DCK | deoxycytidine kinase | NM_000788 | |
| DTL | denticleless homolog (*Drosophila*) | NM_016448 | |
| COL4A2 | collagen, type IV, alpha 2 | NM_001846 | |
| MELK | maternal embryonic leucine zipper kinase | NM_014791 | |
| ZNF880 | N/A | N/A | |
| MTDH | Metadherin, mRNA (cDNA clone IMAGE: 4124124) | NM_178812 | |
| UCHL5 | ubiquitin carboxyl-terminal hydrolase L5 | NM_015984 | |
| RAB6B | RAB6B, member RAS oncogene family | NM_016577 | |
| GPR180 | G protein-coupled receptor 180 | NM_180989 | |
| LPCAT1 | lysophosphatidylcholine acyltransferase 1 | NM_024830 | XM_001717124 |
| SERF1A | small EDRK-rich factor 1A (telomeric) /// small EDRK-rich factor 1B (centromeric) | NM_021967 | NM_022968 |
| CDC42BPA | CDC42 binding protein kinase alpha (DMPK-like) | NM_003607 | NM_014826 |
| NDC80 | NDC80 homolog, kinetochore complex component (*S. cerevisiae*) | NM_006101 | |
| GMPS | guanine monphosphate synthetase | NM_003875 | |
| ECT2 | epithelial cell transforming sequence 2 oncogene | NM_018098 | |
| LOC100134229 | hypothetical protein LOC100134229 | NR_024451 | XM_001716864 |
| MMP9 | matrix metallopeptidase 9 (gelatinase B, 92 kDa gelatinase, 92 kDa type IV collagenase) | NM_004994 | |
| OXCT1 | 3-oxoacid CoA transferase 1 | NM_000436 | |
| GNAZ | guanine nucleotide binding protein (G protein), alpha z polypeptide | NM_002073 | |
| FLT1 | fms-related tyrosine kinase 1 (vascular endothelial growth factor/vascular permeability factor receptor) | NM_002019 | |
| EXT1 | exostoses (multiple) 1 | NM_000127 | |
| C16orf61 | chromosome 16 open reading frame 61 | NM_020188 | |
| DIAPH3 | diaphanous homolog 3 (*Drosophila*) | NM_001042517 | NM_030932 |
| QSOX2 | quiescin Q6 sulfhydryl oxidase 2 | NM_181701 | |
| LOC286052 | hypothetical protein LOC286052 | N/A | |
| NUSAP1 | nucleolar and spindle associated protein 1 | NM_001129897 | NM_016359 |
| LOC744491 | N/A | N/A | |
| TSPYL5 | TSPY-like 5 | NM_033512 | |

TABLE 2

Additional HTICS Biomarkers

| Gene | Gene ID | Accession | Name |
|---|---|---|---|
| *Up regulated:* | | | |
| Kif11 | 3832 | NM_004523.3 | kinesin family member 11 |
| Plk1 | 5347 | NM_005030.3 | polo-like kinase 1 (*Drosophila*) |
| Chek1 | 1111 | NM_001274.4 | CHK1 checkpoint homolog (*S. pombe*) |
| Mphosph6 | 10200 | NM_005792.2 | M-phase phosphoprotein 6 |
| *Down regulated:* | | | |
| Coro1a | 11151 | NM_007074.2 | coronin, actin binding protein, 1A |
| Ccl5 | 6352 | NM_002985.2 | chemokine (C-C motif) ligand 5 |
| Cd3e | 916 | NM_000733.3 | CD3e molecule, epsilon (CD3-TCR complex) |
| Hcls1 | 3059 | NM_005335.4 | hematopoietic cell-specific Lyn substrate 1 |
| Vav1 | 7409 | NM_005428.2 | vav 1 guanine nucleotide exchange factor |
| Plek | 5341 | NM_002664.2 | pleckstrin |
| Arhgdib | 397 | NM_001175.4 | Rho GDP dissociation inhibitor (GDI) beta |
| Il2rg | 3561 | NM_000206.1 | interleukin 2 receptor, gamma (severe combined immunodeficiency) |
| Sash3 | 54440 | NM_018990.3 | SAM and SH3 domain containing 3 |
| Lck | 3932 | NM_005356.3 | lymphocyte-specific protein tyrosine kinase |
| Il2rb | 3560 | NM_000878.2 | interleukin 2 receptor, beta |
| Cybb | 1536 | NM_000397.3 | cytochrome b-245, beta polypeptide |
| Cd79b | 974 | NM_021602.2 | CD79b molecule, immunoglobulin-associated beta |
| Sell | 6402 | NM_000655.3 | selectin L |
| Ccnd2 | 894 | NM_001759.3 | cyclin D2 |
| Tnfrsf1b | 7133 | NM_001066.2 | tumor necrosis factor receptor superfamily, member 1B |
| Rftn1 | 23180 | NM_015150.1 | raftlin, lipid raft linker 1 |
| Rac2 | 5880 | NM_002872.3 | ras-related C3 botulinum toxin substrate 2 (rho family, small GTP binding protein Rac2) |
| Ly86 | 9450 | NM_004271.3 | lymphocyte antigen 86 |

Example 2

Animal, histology, TIC analysis, the generation of HTICS and Kaplan-Meier analysis were performed as described in (14, 29) and FIGS. 7 to 14. TIC frequency was calculated using L-Calc software from www.stemcell.com. Microarray data were normalized using RMA method via Partek software. Score for Signature Match (SSM) was calculated using:

$$SSM=\Sigma(I_n X_n/|X_n|)/\Sigma(|I_n|)$$

Where I is gene index; 1 for up-regulated genes in TICs; −1 for down-regulated genes. X is log 2 transformed and median-centered gene expression value of the patient. SSM≥0 was considered a match. Hazard ratios were calculated using COX Proportional Hazards Survival Regression. Heatmaps and dendrograms were generated by JAVA treeview.

Supplementary Materials and Methods

Mice, Tumor Harvesting, Single Cell Preparation and Enrichment of Lin⁻ Epithelial Cells Mammary tumors (0.5-1.0 cm diameter) and glands were dissected from MMTV-Neu mice (30), fixed in 4% paraformaldehyde and analyzed as described (31, 32). To generate single cell suspension by the enzymatic method, a portion of the tumor was minced into small pieces with sterile razor blade, washed in PBS, digested in 100 U/ml collagenase/hyaluronidase (StemCell Technology, #07912) for 1 hour at 37° C. with occasional mixing, and washed once with 5×HBSS (Sigma, phenol red free, #H4891)+2% FBS & 1 mM EDTA (HFE). For the mechanical method, minced tumor tissue was resuspended in 10 ml HFE and passed through an 18-gauge needle 5 times. Single cell suspensions from enzymatic or mechanical preparations were centrifuged at 1000 rpm, supernatant discarded, and pellet resuspended in 10 ml HFE followed by passing through a 40 μm cell strainer (BD Falcon, #352340). Selective depletion of endothelial (anti-CD31, BD PharMingen) and hematopoietic cells (anti-CD45 and anti-TER119, StemCellTechnologies) was accomplished with magnetic beads using a Mammary Stem Cell Enrichment kit from StemCell Technology (#19757). We found that the inclusion of anti-CD140a antibodies to deplete fibroblasts was not necessary for Neu tumors (n=4).

Flow Cytometry Analysis and Sorting

For flow cytometry, we used anti-CD49f conjugated with R-phycoerythrin (CD49f-PE, clone GoH3, 5 μl/million cells, BD Pharmingen #555736), anti-CD24 conjugated with fluorescein isothiocyanate (CD24-FITC, clone M1/69, 0.25 μg/million cells, BD Pharmingen #553261), anti-Sca1 conjugated with R-phycoerythrin (Sca1-PE, clone E13-161.7, 0.25 μg/million cells, BD Pharmingen #553108), rabbit-anti-Jagged1 (Cell Signaling, clone 28H8, 1:250 dilution, #2620), biotin-anti-Notch1 (BioLegend, clone mN1A, 1:250 dilution, #629104), and mouse-anti-HER2 (CalBiochem, clone Ab-4, 1:250 dilution, #0P16). For Jagged1, we used secondary biotin-anti-rabbit antibody (Vector, #BA-1000) followed by APC-Streptavidin (BD Pharmingen, #554067); Notch1, APC-Streptavidin; and HER2, anti-mouse-Ig conjugated with R-phycoerythrin (BD Pharmingen, #559940). Cells were suspended in HBSS+2% FBS & 1 mM EDTA (HFE) at 5 million cells/ml and incubated with indicated antibodies and cell-viability markers on ice for 30 minutes. After 3× washes in HFE, cells were re-suspended in HFE at 5 million cells/ml and kept on ice pending analysis. Single (fixed FSC-A/FSC-W ratio) and live cells (PI- or 7AAD-negative) were gated for analysis and sorting. For flow cytometry analysis, 7AAD (BD Pharmigen, Cat #51-68981E) was used as the viability marker with FACSCalibur (Becton Dickinson, San Jose, Calif.). For sorting, Propidium Iodide (PI; BD Pharmigen, Cat #550825) was used for selecting live cells in 13 color FACSAria (Becton Dickinson, San Jose, Calif.) with 488 nm Blue laser at 20 PSI, HSC-UHN Flow Cytometry Facility (Toronto).

Histology and Immunofluorescence Staining

Tissue sections were deparaffinized twice with xylene for 10 minutes each and sequentially hydrated with 100%, 90%, 70% and 50% ethanol in PBS. For antigen retrieval, slides were boiled in a microwave in 10 mM Sodium Citrate solution, pH6.0, for ≥10 min followed by 30 min gradual cooling at RT. Sections were incubated with M.O.M-™Mouselg blocking reagent for one hour (Vector® M.O.M™ Immunodetection kit, Vector Laboratories, CA, Cat #2202) followed by incubation with primary antibodies diluted in M.O.M™ in a humidified chamber at 4° C. overnight. Secondary antibodies (goat anti rabbit Alexa 488 and goat anti mouse Alexa 568, both 1:200 dilution) plus DAPI were added for 1 hr at RT. The slides were mounted with DakoCytomation fluorescence medium. Primary antibodies were against mouse keratin18 (K18, 1:200 dilution, Fitzgerald, #RD1-PR061028), keratin14 (K14, 1:200 dilution, Panomics, #E2624), HER2 (CalBiochem, 1:200 dilution, #OP16), Jagged1 (CellSignaling, 1:200 dilution, #2620), Vimentin (SantaCruz, 1:200 dilution, #SC32322). We note that TIC frequency is reproducibly higher (2 fold) after positive immuno-selection with EasySep beads compared with cell sorting. However, as opposed to FACS, which allows single cell purification, immuno-purification gives rise to clumps of 2 or more cells.

Transplantation

For picking single cells, CD24⁺:JAG1⁻ cells were diluted to 1 cell/10 μl and 10 μl was seed into each well on Terasaki plates. After 30 min to allow cells for settling on the bottom of each well, the presence of a single cell/well was confirmed by microscopic examination. Single cells in 10 μl were mixed with 10 μl matrigel (BD Bioscience #356234) on ice. Samples (total 20 μl) were injected into #4 mammary glands of 3-5 week old FVB, Rag1$^{-/-}$, SCID-Beige (Jackson; Charles River) or MMTV-Neu female mice under isoflurane anesthesia. Liquid bandage (NewSkin #1310206) was applied to prevent sample leakage; wounds were closed by 9 mm autoclip (Clay Adams Brand #427631) and removed 2 weeks post-surgery.

Microarray Analysis

Microarray analysis was carried out using Illumina Mouse Ref-8 v2 with 500 ng of total RNA at the Centre for Applied Genomics (HSC, Toronto). Total RNA from tumor tissue was prepared using the double Trizol method. In short, tumor samples were minced using a razor blade, resuspended in 1 ml Trizol and incubated on ice for 20 min. 200 μl of chloroform was added and samples shaken at 1200 rpm for 10 minutes at RT. After centrifuging the samples at 13000 rpm for 10 minutes, the upper aqueous layer was transferred to a new tube and RNA precipitated with 600 μl isopropanol. Samples were centrifuged at 13000 rpm for 10 minutes at 4° C. and supernatants removed. RNA pellets were air-dried, 5 minutes, resuspended in 100 μl of RNAse-free H₂O, and Trizol purification procedure repeated once. Microarray data was first normalized by Quantile method using BeadStudio (Illumina) with the pooled result of primary MMTV-Neu tumors as reference group to generate a list of genes with significant differential expression.

Microarray data are archived at GEO (GSE29616) and can be viewed at:
http://www.ncbi.nlm.nih.gov/geo/query/acc.cgi?acc=GSE29616)

Generation and Analysis of HER2 Signature

To generate a list of differentially expressed genes, five independent primary mammary tumors from MMTV-Neu model (N250, N261, N283, N222, N229) were harvested and tumor cells were mechanically dissociated into single cell suspension. Cells from each tumor (with the exception of N222 and N229, which were combined in a 1:1 ratio to obtain enough cells) were FACS sorted into TIC/CD24$^+$:JAG1$^-$ and non-TIC/CD24$^-$ fractions. Total RNA purified from the 8 samples using PicoPure RNA Isolation Kit (Arcturus) was subject by Affymetrix Mouse Gene 1.0 st microarray analysis at the Centre of Applied Genomics (HSC, Toronto). Data are archived at GEO (GSE29590):
http://www.ncbi.nlm.nih.gov/geo/query/acc.cgi?acc=GSE29590

Microarray data were normalized using RMA method via Partek software and log 2 transformed gene expression values were obtained. Paired t-test statistics were performed between the TIC and CD24$^-$ fractions to identify significantly ($p<0.05$) and differentially (>2.0 fold) expressed genes. 73 genes were significantly up-regulated in the TIC fraction and 256 genes significantly up-regulated in the CD24$^-$ fraction. The prognostic value of each gene was assessed using GSE3143 dataset as a training set. Out of total 329 differentially regulated (TICs vs non-TICs) mouse genes, 284 human genes were found in the GPL8300 platform of GSE3143 dataset. The expression data was median-centered for each gene with all the samples in the cohort. Selection of HER2$^+$ patients was based on a published method using the 5 genes in the HER2 amplicon (ErbB2, Stard3, Perld1, Grb7, & C17orf37). A patient was considered to be HER2$^+$ if at least 3 of the 5 genes were expressed 2-folds above median, We tested the method with 11 published databases containing HER2 IHC results (GSE24185, GSE22358, GSE25066, GSE2603, GSE5460, GSE21653, GSE26639, GSE19697, GSE17907, GSE16446, &GSE20194; FIG. 13) and determined that at 2-fold cut-off, 80.7% of the amplicon-selected patients were also HER2$^+$ by IHC and 69.5% of total IHC HER2$^+$ samples were included.

Using all 284 genes differentially regulated in TICs, the HER2$^+$ patients were divided into two groups using the formula:

Score for Signature Match (SSM)=
$\Sigma(I_n X_n/|X_n|)/\Sigma(|I_n|)$

Where I is the gene index; 1 for up-regulated genes in TICs and −1 for down-regulated genes. X is the log 2 transformed and median-centered gene expression value of the patient. SSM≥0 was considered to be a match to the signature. Using these criteria, the 284 differentially regulated TIC genes identify a group of HER2$^+$ patients with poor prognosis (HR=2.54, P=0.072, FIG. 14A) in the GSE3143 dataset. To further improve the signature, HER2$^+$ patients were divided into poor (overall survival: OS=1) and good (OS=0). Ward's Agglomerative Clustering divided the poor group of HER2$^+$ patients into two subgroups, Cluster1 with the average survival of 34 months, and Cluster2 with average survival of 48 months. We used a scoring algorithm that calculates the association of the expression of the gene to a particular patient group:

Gene Association (GA)=$(\Sigma X_i/|X_i|)/n$

Where X is the expression of the gene and n is the number of patients in the given group. For up-regulated genes in TICs, a criterion of GA score>0.5 in cluster1 or cluster2 was used, and 10 genes were found to be qualified. For down-regulated genes, we set the criterion to be GA score<−0.5 in cluster1 or cluster2, and also a positive association of GA>0.3 with good-prognosis group. 48 down-regulated genes met this criterion. The combined 40 genes were used to analyze patient prognosis and an improved prediction was achieved (HR=3.53, P=0.00742, FIG. 14A). Finally, we performed progressive elimination analysis by adjusting the cut-off value for the GA score with good-prognosis group of patients. For up-regulated genes, a cut-off of GA<0.2 was determined for both cluster1 and cluster2, and 8 genes (Aurkb, Cldn8, Npy, Atp7b, Chaf1b, Scrn1, Ccna2, &Ccnb1) were selected. For down-regulated genes, a cut-off was set at GA>0.4 for cluster1 and GA>0.3 for cluster2; 9 genes (Nrp1, Cd74, C1qb, Cd72, Vcam1, Itgb2, Cd180, Ccr2, & St8sia4) passed the criteria. The resulting 17-gene signature, HTICS, gave the best prediction on patient outcome in GSE3143 dataset (HR=5.24, p=0.000491, FIG. 4A).

To validate the signature, we used HTICS to analyze 6 datasets with overall survival data (GSE1456, GSE3494, GSE7390, GSE16446, GSE18229, & GSE20685) of which 4 also had ERα status (GSE3494, GSE7390, GSE16446, & GSE18229). In addition, the status of p53 mutation was provided by GSE3494. In addition, 6 datasets with metastasis-free survival data (GSE2034, GSE2603, GSE 5327, GSE6532, GSE11121, & GSE25066) were used 4 of which provided ERα status (GSE2034, GSE2603, GSE6532, & GSE25066). Finally, 2 datasets with disease-free survival data were analyzed (GSE4922 & GSE12093). Total of 14 datasets were included across 10 different Affymetrix and Agilent platforms (GPL8300, GPL96, GPL570, GPL885, GPL887, GPL1390, GPL1708, GPL5325, GPL6607, & GPL7504).

2 datasets with pathological complete response (pCR) information were analyzed: GSE22358 and the MD Anderson cohorts. For pCR analysis, only samples with complete responses (pCR) were considered to be success and all other responses (partial, minor, near-complete) were regarded as failure. SSM for HTICS was calculated for each sample and number of patients with success/failure in HTICS$^-$/HTICS$^+$ groups was assessed by chi-square test to determine significance. For post-surgery analysis, such as % metastasis and overall survival/MFS Kaplan-Meier curves, 2 samples (one HER2$^+$:ERα$^+$, one HER2$^+$:ERα$^-$) were removed from the MD Anderson cohort due to a different adjuvant chemotherapy regimens. For % metastasis analysis, HER2$^+$:ERα$^-$ samples from published cohorts were combined as Trastuzumab$^-$ group and used to compare to the Trastuzumab-treated (Trastuzumab$^+$) patients from MD Anderson. Statistical significance was calculated by chi-square test.

Each dataset was analyzed independently by obtaining RMA normalized expression value of the individual cohort for log 2 transformation and median-centering. HER2$^+$ patients were then selected by amplicon method for signature analysis with SSM algorithm. The comparison with additional signatures was done with SSM algorithm for all signatures to ensure equal comparison. Kaplan-Meier and Survival analysis were performed with PAST program (P. D. Ryan and Ø. Hammer, University of Oslo) and p-value was calculated by Wilcoxon method. Hazard ratios were obtained using the COX Proportional Hazards Survival Regression method. Heatmaps and dendrograms were generated by JAVA tree-view.

Pathway Analysis

Figure 3:
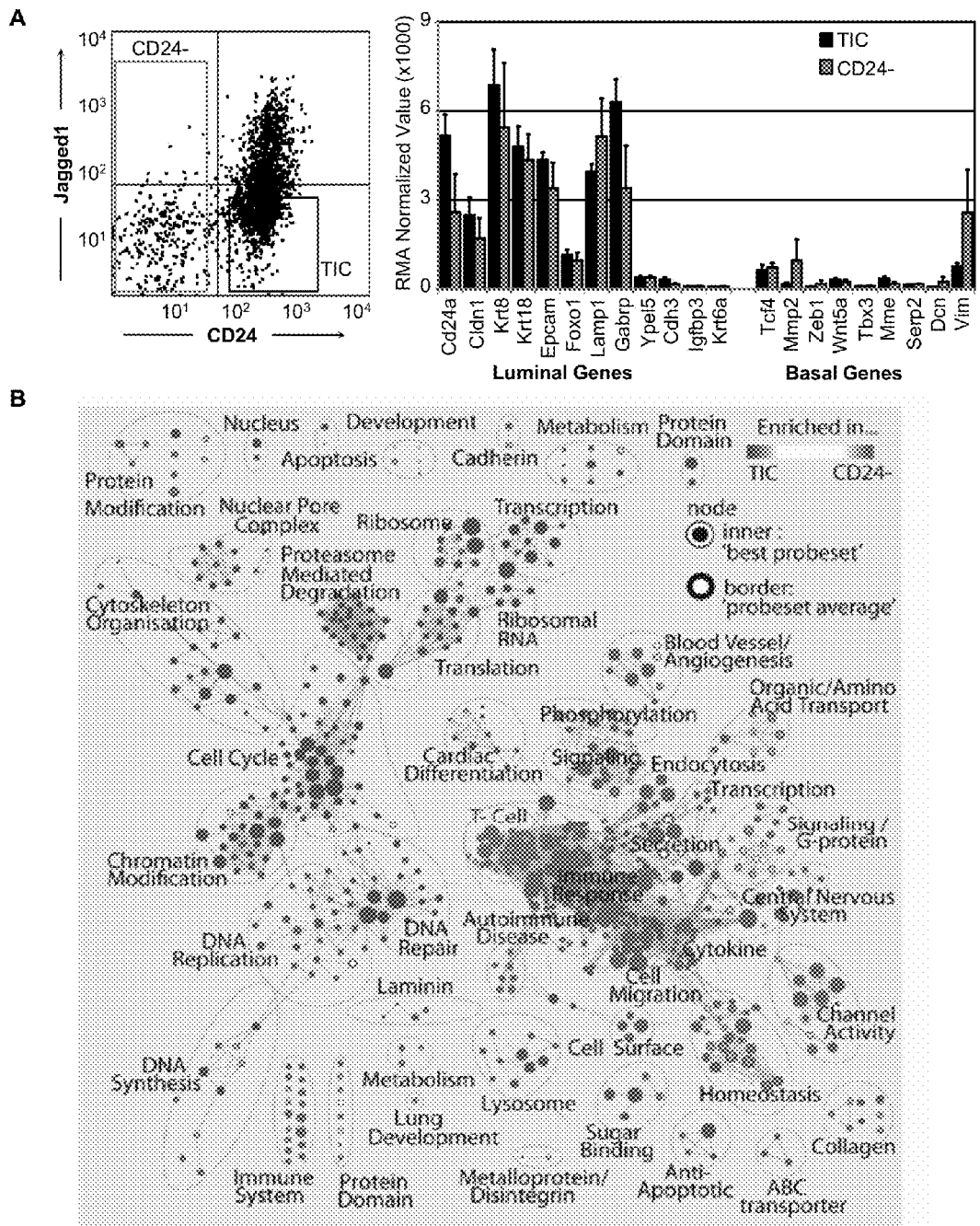
FIG. 3. TheHer2/Neu $CD24^+$:$JAG1^-$ TIC fraction is enriched in genes associated with dividing but not differentiating cells. (A) Left, gating conditions used to sort $lin^-$ MMTV-Her2/neu tumor cells. Right, expression of luminal and basal genes in $CD24^+$:$JAG1^-$ TICs versus non-TICs. (B) Functional enrichment map for TIC/$CD24^+$:$JAG1^-$ versus non-TIC/$CD24^-$ fractions revealing distinct pathways in each group. Nodes (circles) represent a significantly enriched pathways; clusters on the top and left indicates gene sets enriched in TIC, and bottom right clusters are in non-TIC fractions.

The data were analyzed by GSEA (33) using paired t-test comparing gene expression values in the TIC and CD24⁻ fractions, and parameters set to 2,000 gene-set permutations, gene-sets size between 15 and 500. An enrichment map (version 1.1 of Enrichment Map software (34)) was generated using enriched gene-sets with a nominal p-value <0.005, FDR<1% and the overlap coefficient set to 0.5. The databases included in the GSEA analyses were the Gene Ontology (GO), KEGG, PFAM, BIOCARTA and NCI databases. GO, PFAM and KEGG annotations were downloaded from Bioconductor (org.Mm.eg.db version 2.4.6, GO.db version 2.4.5, KEGG.db version 2.4.5). NCI annotations were downloaded from NCI website (http://pid.nci.nih.gov/, 2010-11-08) and BioCarta annotations downloaded from WhichGenes (2010-03-26). In FIG. 3, node size corresponds to the number of genes in the gene set, which are connected by edges when they have genes in common, with line width corresponding to the number of shared genes.

Additional Statistical Analysis

Paired samples were analyzed by student t-test. Significance of comparing multiple samples was calculated using ANOVA and the Bonferroni test for post hoc analysis. Differences between values were considered statistically significant at $P<0.05$. TIC frequency and 95% confidence intervals were calculated using L-Calc software from www.stemcell.com.

Example 3

Formalin fixed paraffin embedded (FFPE) tumor biopsies will be cut (3-5 scrolls) by pathologist. RNA will be extracted and used to perform the Nanostring assay for HTICS. The data will then be analyzed using to identify HTICS− and HTICS+ patients. Probes described in Table 3 and FIGS. 16 and 17 will be used for the analysis.

Example 4

Specialized program computing Survival Analysis was written in C++ language. Formulas of Log-rank method was used to calculate statistical significance and estimate hazard ratio (equations detailed in Chapter 2 of Kleinbaum, D. G. & Klein, M. 2005. Survival analysis: a self-learning text. Springer). The 1000 sets of randomly selected signatures were generated by atmospheric background noise using on-line engine at www.random.org. Each random signature has exactly the same number of genes as HTICS with 8 genes designated as up-regulated and 9 genes designated as down-regulated. HER2+ patients from 6 cohorts with MFS data (GSEs 2034, 2603, 5327, 6532, 11121, and 25066) and 2 cohorts with OS data (GSEs 16446 and 20685) were selected. Due to different microarray platforms containing different number of genes used for MFS and OS cohorts, the random sets of signatures were generated separately. HTICS ranked #2 and #12 in MFS and OS tests with HER2+ samples comparing to 1000 random signatures and had significant HR>2.0. With sufficient HER2+ER− samples in MFS cohorts, HTICS performs even better with significant HR>5.0 and ranked #2 compared to 1000 random signatures. The consistent good performance of HTICS (ranked #2 in both) is also evident from the fact that the #1 ranked signature in MFS HER2+ test was different from the #1 in MFS HER2+ER− test. See FIG. 15.

Example 5

Details of nanostring probes for each HTICS genes and cell types expressing them (as determined by nanostring assay) are described in Table 3.

TABLE 3

Cell Types (Breast Cancer or Stromal) Expressing HTICS genes and Corresponding Affymetrix Probe ID, Nanostring Probe Range and Sequence

| | HTICS | Entrez ID | RefSeq | Name | Expressing Cell Type | Range & Sequence | Affymetrix ID |
|---|---|---|---|---|---|---|---|
| Up-Regulated in TIC | Aurkb | 20877 | NM_004217<br>615-715 | Aurora Kinase B | Breast Cancer | AGATGCTCTAATGTACTGCCATGGAAGAAGGTGATTCACAGAGACATAAAGCCAGAAAATCTGCTCTTAGGGCTCAAGGGAGAGCTGAAGATTGCTGAC (SEQ ID NO: 1) | 209464_at |
| | Ccna2 | 12428 | NM_001237<br>1210-1310 | Cyclin A2 | Breast Cancer | CGGGACAAAGCTGGCCTGAATCATTAATACGAAAGACTGGATATACCCTGGAAAGTCTTAAGCCTTGTCTCATGGACCTTCACCAGACCTACCTCAAAGC (SEQ ID NO: 2) | 203418_at |
| | Scrn1 | 69938 | NM_014766<br>2045-2145 | Secernin 1 | Breast Cancer | TCCCATTTTCCATGCGCTGTGCTTATGTGTGGTGGACTGCCAGAGCTGCTTCCACTTACAGGAGAGCTGATAATTTGTTAGCTGGAACCTATTCACTTCCG (SEQ ID NO: 3) | 201462_at |
| | Npy | 109648 | NM_000905<br>270-370 | Neuropeptide Y | Breast Cancer | AGAGATATGGAAAACGATCCAGCCCAGAGACACTGATTTCAGACCTCTTGATGAGAGAAAGCACAGAAAATGTTCCCAGAACTCGGCTTGAAGACCCTGC (SEQ ID NO: 4) | 206001_at |
| | Atp7b | 11979 | NM_000053<br>675-775 | ATPase, Cu++ transporting, beta polypeptide | Breast Cancer | AGTCAAAGTCTCACTCAGCAACCAAGAGGCCGTCATCACTTATCTCATTCAGCCTTATCTCAGGGACCTCAGGACCATGTAAATGACATGGGATTT (SEQ ID NO: 5) | 204624_at |
| | Chaf1b | 110749 | NM_005441<br>795-895 | Chromatin assembly factor 1, subunit B | Breast Cancer | GGAGAGGCAAGAAGCTACCGGATGTTCACGACGCAGCATGAGTCTTTTCTTCCGTAGACTGAGTTTCACTCCCGACGATCTTTGCTTCTCACGCCAG (SEQ ID NO: 6) | 204775_at |
| | Ccnb1 | 268697 | NM_031966<br>715-815 | Cyclin B1 | Breast Cancer | AACTTGAGGAAGAGCAAGCAGTCAGACCAAAATACCTACTGGGTCGGGAAGTCACTGGAAACATGAGACGCCATCCTAATTGACTGGCTAGTAGGTTCA (SEQ ID NO: 7) | 214710_s_at |
| | Cldn8 | 54420 | NM_199328<br>805-905 | Claudin 8 | Breast Cancer | AGCTACAGATACTCGATACCTTCCCATGCACACCCAAAAAAGTTATCACACCGGAAAGAAGTCACCGAGCGTCTACTCCAGAAGTCAGTATGTGTAGT (SEQ ID NO: 8) | 214598_at |

TABLE 3-continued

Cell Types (Breast Cancer or Stromal) Expressing HTICS genes and Corresponding Affymetrix Probe ID, Nanostring Probe Range and Sequence

| | HTICS | Entrez ID | RefSeq | Expressing Cell Type | Name | Affymetrix ID |
|---|---|---|---|---|---|---|
| Up-Regulated in CD24- | Nrp1 Range&Sequence: | 18186 | NM_003873 370-470 | Breast Cancer & Stromal | Neuropilin 1 GCCTCGCTGCTTCTTTTCTTTTCTCCAAGACGGGCTGAGGATTGTACAGCTCTAGGCGGAGTTGGGCTCTTCGGATCGCTTAGATTCTCCTCTTTGCTGCATT (SEQ ID NO: 9) | 210510_s_at |
| | Ccr2 Range&Sequence: | 12772 | NM_000647 20-120 | Stromal | Chemokine (C-C motif) receptor 2 ACATTCTGTGTGCTCATATCATGCAAATTATCACTAGGAGGACAGAGAGTGGAAATGTTCCAGGTATAAAGACCCACAAGATAAAGAAGCTCAGAG (SEQ ID NO: 10) | 206978_at |
| | C1qb Range&Sequence: | 12260 | NM_000491 819-919 | Stromal | Complement component 1, q subcomponent binding protein AACTCACTACTGGGCATGGAGGGTGCCAACAGCATCTTTTTCCGGGTTCCTGCTCTTTCCAGATATGGAGGCCTGACCTGTGGGCTGCTTCACATCCACCC (SEQ ID NO: 11) | 202953_at |
| | CD74 Range&Sequence: | 16149 | NM_004355 964-1064 | Stromal | CD74 molecule TTCAGCCCCCAGCCCCTCCCCCAGTCCCCCATCTCCACCCTGTACCTCATCCCATGAGACCCCTGGTGCCTGGCTCTTTCGTCACCCTTGGACAAGACAAACCAAGTC (SEQ ID NO: 12) | 209619_at |
| | Vcam1 Range&Sequence: | 22329 | NM_001078 2535-2635 | Breast Cancer | Vascular cell adhesion molecule 1 CAGACTTCCCTGAATGTATTGAACTTGGAAAGAAAATGCCCATCTATGTCCCTGCTGTGAGCAAGAAGTCAAAGTAAAACTTGCTCGAAGAACAGTA (SEQ ID NO: 13) | 203868_s_at |
| | CD180 Range&Sequence: | 17079 | NM_005582 20-120 | Stromal | CD180 molecule GCATTTCTTGTTCCAAGATCACCCTTCTGAGTACCTCTCTGGCTGCCAAATTGCCAGGGCCTTCACAGTTTGATTCCATTTCTCAGCTCCAAGCATTAGG (SEQ ID NO: 14) | 206206_at |
| | Itgb2 Range&Sequence: | 16414 | NM_000211 520-620 | Stromal | Integrin, beta 2 CATCGACCTGTACTATCTGATGACCTCTCCTACTCCATGCTTGATGACCTCAGGAATGTCAAGAAGCTAGGTGGCGACCTGCTCCGGGCCCTCAACGAG (SEQ ID NO: 15) | 202803_s_at |
| | CD72 Range&Sequence: | 12517 | NM_001782 1044-1144 | Stromal | CD72 molecule GAAGTTGACTGATGATAACAACGCACTAGGACTTATGCTCAAAGCTCAAAATGTAACAAGGTACATAAAATGTAACAAGGTACATCATGGACTGAGTCAGAG (SEQ ID NO: 16) | 215925_s_at |
| | St8sia4 Range&Sequence: | 20452 | NM_175052 695-795 | Breast Cancer & Stromal | ST8 alpha-N-acetyl-neuraminide alpha-2,8-sialyltransferase 4 ATCTACATAGCCTCTACCTGAAGTTTCACCAATGAAGATCGCAGGTTTAAGACCTGTGCAGTTGTGGAAATTCTGGCATTCTGCATTCTGTTAGACAGTGAATG (SEQ ID NO: 17)Ê. | 206925_at |

The Nanostring assay detected significant signals for every gene in HTICS above background variation using Human Breast cancer cell lines and lymphocytes, indicating successful probe design and readiness for clinical testing (FIG. 16).

Example 6

Positive and significant correlation between Microarray analysis and Nanostring assay has been demonstrated (FIG. 17). As the efficacy of HTICS has been demonstrated using microarray data (PNAS 2012), this consistency of nanostring results further support its use for clinical tests.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequence associated with each accession number provided herein is incorporated by reference in its entirely

REFERENCES

1. Slamon D J, Leyland-Jones B, Shak S, Fuchs H, Paton V, Bajamonde A, Fleming T, Eiermann W, Wolter J, Pegram M, Baselga J, Norton L (2001) Use of chemotherapy plus a monoclonal antibody against HER2 for metastatic breast cancer that overexpresses HER2. *N Engl J Med* 344(11): 783-792.
2. Abramson V, Arteaga C L (2011) New strategies in HER2-overexpressing breast cancer: many combinations of targeted drugs available. *Clin Cancer Res* 17(5):952-958.
3. Dean-Colomb W, Esteva F J (2008) Her2-positive breast cancer: herceptin and beyond. *Eur J Cancer* 44(18):2806-2812.
4. Gianni L, Dafni U, Gelber R D, Azambuja E, Muehlbauer S, Goldhirsch A, Untch M, Smith I, Baselga J, Jackisch C, Cameron D, Mano M, Pedrini J L, Veronesi A, Mendiola C, Pluzanska A, Semiglazov V, Vrdoljak E, Eckart M J, Shen Z, Skiadopoulos G, Procter M, Pritchard K I, Piccart-Gebhart M J, Bell R (2011) Treatment with trastuzumab for 1 year after adjuvant chemotherapy in patients with HER2-positive early breast cancer: a 4-year follow-up of a randomised controlled trial. *Lancet Oncol* 12(3):236-244.
5. Martin M, Esteva F J, Alba E, Khandheria B, Perez-Isla L, Garcia-Saenz J A, Marquez A, Sengupta P, Zamorano J (2009) Minimizing cardiotoxicity while optimizing treatment efficacy with trastuzumab: review and expert recommendations. *Oncologist* 14(1):1-11.
6. O'Brien C A, Kreso A, Dick J E (2009) Cancer stem cells in solid tumors: an overview. *SeminRadiatOncol* 19(2): 71-77.
7. Cicalese A, Bonizzi G, Pasi C E, Faretta M, Ronzoni S, Giulini B, Brisken C, Minucci S, Di Fiore P P, Pelicci P G (2009) The tumor suppressor p53 regulates polarity of self-renewing divisions in mammary stem cells. *Cell* 138(6):1083-1095.
8. Korkaya H, Paulson A, Iovino F, Wicha M S (2008) HER2 regulates the mammary stem/progenitor cell population driving tumorigenesis and invasion. *Oncogene*.
9. Desmedt C, Haibe-Kains B, Wirapati P, Buyse M, Larsimont D, Bontempi G, Delorenzi M, Piccart M, Sotiriou C (2008) Biological processes associated with breast cancer clinical outcome depend on the molecular subtypes. *Clin Cancer Res* 14(16):5158-5165.
10. Paik S, Shak S, Tang G, Kim C, Baker J, Cronin M, Baehner F L, Walker M G, Watson D, Park T, Hiller W, Fisher E R, Wickerham D L, Bryant J, Wolmark N (2004) A multigene assay to predict recurrence of tamoxifen-treated, node-negative breast cancer. *N Engl J Med* 351 (27):2817-2826.
11. Liu R, Wang X, Chen G Y, Dalerba P, Gurney A, Hoey T, Sherlock G, Lewicki J, Shedden K, Clarke M F (2007) The prognostic role of a gene signature from tumorigenic breast-cancer cells. *N Engl J Med* 356(3):217-226.
12. Finak G, Bertos N, Pepin F, Sadekova S, Souleimanova M, Zhao H, Chen H, Omeroglu G, Meterissian S, Omeroglu A, Hallett M, Park M (2008) Stromal gene expression predicts clinical outcome in breast cancer. *Nat Med* 14(5): 518-527.
13. Guy C T, Webster M A, Schaller M, Parsons T J, Cardiff R D, Muller W J (1992) Expression of neuprotooncogene in the mammary epithelium of transgenic mouse induces metastatic disease. *Proc. Natl. Acad. Sci. USA* 89:10578-10582.
14. Liu J C, Deng T, Lehal R S, Kim J, Zacksenhaus E (2007) Identification of Tumorsphere- and Tumor-Initiating Cells in HER2/Neu-Induced Mammary Tumors. *Cancer Res* 67(18):8671-8681.
15. Vaillant F, Asselin-Labat M L, Shackleton M, Forrest N C, Lindeman G J, Visvader J E (2008) The mammary progenitor marker CD61/beta3 integrin identifies cancer stem cells in mouse models of mammary tumorigenesis. *Cancer Res* 68(19):7711-7717.
16. Reedijk M, Odorcic S, Chang L, Zhang H, Miller N, McCready D R, Lockwood G, Egan S E (2005) High-level coexpression of JAG1 and NOTCH1 is observed in human breast cancer and is associated with poor overall survival. *Cancer Res* 65(18):8530-8537.
17. Osipo C, Patel P, Rizzo P, Clementz A G, Hao L, Golde T E, Miele L (2008) ErbB-2 inhibition activates Notch-1 and sensitizes breast cancer cells to a gamma-secretase inhibitor. *Oncogene* 27(37):5019-5032.
18. Muller W J, Sinn E, Pattengale P K, Wallace R, Leder P (1988) Single step induction of mammary adenocarcinoma in transgenic mice bearing the activated c-neu oncogene. *Cell* 54:105-115.
19. Kmieciak M, Knutson K L, Dumur C I, Manjili M H (2007) HER-2/neu antigen loss and relapse of mammary carcinoma are actively induced by T cell-mediated anti-tumor immune responses. *Eur J Immunol* 37(3):675-685.
20. Notta F, Mullighan C G, Wang J C, Poeppl A, Doulatov S, Phillips L A, Ma J, Minden M D, Downing J R, Dick J E (2011) Evolution of human BCR-ABL1 lymphoblastic leukaemia-initiating cells. *Nature* 469(7330):362-367.
21. Subramanian A, Tamayo P, Mootha V K, Mukherjee S, Ebert B L, Gillette M A, Paulovich A, Pomeroy S L, Golub T R, Lander E S, Mesirov J P (2005) Gene set enrichment analysis: a knowledge-based approach for interpreting genome-wide expression profiles. *ProcNatlAcadSci USA* 102(43):15545-15550.

22. Merico D, Isserlin R, Stueker O, Emili A, Bader G D (2011) Enrichment map: a network-based method for gene-set enrichment visualization and interpretation. *PLoS One* 5(11):e13984.
23. Staaf J, Ringner M, Vallon-Christersson J, Jonsson G, Bendahl P O, Holm K, Arason A, Gunnarsson H, Hegardt C, Agnarsson B A, Luts L, Grabau D, Ferno M, Malmstrom P O, Johannsson O T, Loman N, Barkardottir R B, Borg A (2010) Identification of subtypes in human epidermal growth factor receptor 2—positive breast cancer reveals a gene signature prognostic of outcome. *J ClinOncol* 28(11):1813-1820.
24. Shirley S H, Rundhaug J E, Tian J, Cullinan-Ammann N, Lambertz I, Conti C J, Fuchs-Young R (2009) Transcriptional regulation of estrogen receptor-alpha by p53 in human breast cancer cells. *Cancer Res* 69(8):3405-3414.
25. Whitfield M L, George L K, Grant G D, Perou C M (2006) Common markers of proliferation. *Nat Rev Cancer* 6(2):99-106.
26. Gluck S, Ross J S, Royce M, McKenna E F, Jr., Perou C M, Avisar E, Wu L (2011) TP53 genomics predict higher clinical and pathologic tumor response in operable early-stage breast cancer treated with docetaxel-capecitabine+/−trastuzumab. *Breast Cancer Res Treat* DOI: 10.1007/s10549-011-1412-7.
27. ValastyanS, Weinberg R A (2011) Tumor metastasis: molecular insights and evolving paradigms. *Cell* 147(2): 275-292.
28. Geiss G K, Bumgarner R E, Birditt B, Dahl T, Dowidar N, Dunaway D L, Fell H P, Ferree S, George R D, Grogan T, James J J, Maysuria M, Mitton J D, Oliveri P, Osborn J L, Peng T, Ratcliffe A L, Webster P J, Davidson E H, Hood L, Dimitrov K (2008) Direct multiplexed measurement of gene expression with color-coded probe pairs. *Nat Biotechnol* 26(3):317-325.
29. Jiang Z, Deng T, Jones R, Li H, Herschkowitz J I, Liu J C, Weigman V J, Tsao M S, Lane T F, Perou C M, Zacksenhaus E (2010) Rb deletion in mouse mammary progenitors induces luminal-B or basal-like/EMT tumor subtypes depending on p53 status. *J Clin Invest* 120(9): 3296-3309.
30. Guy C T, Webster M A, Schaller M, Parsons T J, Cardiff R D, Muller W J (1992) Expression of neuprotooncogene in the mammary epithelium of transgenic mouse induces metastatic disease. Proc. Natl. Acad. Sci. USA 89:10578-10582.
31. Liu J C, Deng T, Lehal R S, Kim J, Zacksenhaus E (2007) Identification of Tumorsphere- and Tumor-Initiating Cells in HER2/Neu-Induced Mammary Tumors. Cancer Res 67(18):8671-8681.
32. Jiang Z, Deng T, Jones R, Li H, Herschkowitz J I, Liu J C, Weigman V J, Tsao M S, Lane T F, Perou C M, Zacksenhaus E (2010) Rb deletion in mouse mammary progenitors induces luminal-B or basal-like/EMT tumor subtypes depending on p53 status. J Clin Invest 120(9): 3296-3309.
33. Subramanian A, Tamayo P, Mootha V K, Mukherjee S, Ebert B L, Gillette M A, Paulovich A, Pomeroy S L, Golub T R, Lander E S, Mesirov J P (2005) Gene set enrichment analysis: a knowledge-based approach for interpreting genome-wide expression profiles. ProcNatlAcadSci USA 102(43):15545-15550.
34. Merico D, Isserlin R, Stueker O, Emili A, Bader G D (2011) Enrichment map: a network-based method for gene-set enrichment visualization and interpretation. PLoS One 5(11):e13984.

The invention claimed is:

1. A method of treating a subject afflicted with HER2+ ERα negative breast cancer, the method comprising:
   a. obtaining a subject test sample;
   b. for each of a plurality of HTICs biomarkers, using a biomarker specific probe to determine a RNA expression level for each of the plurality of HTICs biomarkers in the test sample, the HTICs biomarkers consisting of Group (A) Aurkb, Ccna2, Scrn1, Npy, Atp7b, Chaf1b, Ccnb1 and Cldn8, and Group (B) Nrp1, Ccr2, C1qb, Cd74, Vcam1, Cd180, Itgb2, Cd72 and St8sia4;
   c. calculating a signature score match (SSM) according to the formula $$\Sigma(I_n X_n / |X_n|) / \Sigma(|I_n|);$$

where I is the gene index for each HTICs biomarker (n) wherein the gene index of 1 is used for HTICs biomarkers which are up-regulated genes in TICs and the gene index −1 for down-regulated genes in TICs; X is the log 2 transformed and median-centered and/or normalized RNA expression level for each HTICs biomarker (n); and
   d. administering adjuvant anti-HER2 treatment to the subject when the subject is identified as having a SSM of greater than and/or equal to 0 and administering treatment excluding adjuvant anti-HER2 treatment when the SSM score is less than 0.

2. The method of claim 1, wherein a SSM of greater than and/or equal to 0 is an indication of having an increased likelihood of a poor response to treatment without adjuvant anti-HER2 treatment and a SSM of less than 0 is an indication of having an increased likelihood of a good response to treatment without adjuvant anti-HER2 treatment.

3. The method of claim 2, wherein the poor response to treatment indicates decrease in likelihood of survival, decrease likelihood of disease free survival and/or decreased likelihood of metastasis free survival.

4. The method of claim 1, wherein the HER2+ ERα negative breast cancer is node positive.

5. The method of claim 1, wherein the adjuvant anti-HER2 treatment comprises trastuzamab, pertuzumab or lapatinib treatment.

6. The method of claim 1, wherein the HTICs expression signature is determined in a formalin fixed, parafilm embedded (FFPE) test sample.

7. A method of treating a HER2+ ERα negative breast cancer subject in need thereof comprising:
   administering chemotherapy and adjuvant anti-HER2 treatment to the subject when the subject is identified as having a signature score match (SSM) greater than and/or equal to 0 and administering chemotherapy without adjuvant anti-HER2 treatment to the subject when the subject is identified as having a SSM less than 0, wherein the SSM is calculated according to the formula $$\Sigma(I_n X_n / |X_n|) / \Sigma(|I_n|);$$

where I is the gene index for each HTICs biomarker (n), the HTICs biomarkers consisting of Group (A) Aurkb, Ccna2, Scrn1, Npy, Atp7b, Chaf1b, Ccnb1 and Cldn8, and Group (B) Nrp1, Ccr2, C1qb, Cd74, Vcam1, Cd180, Itgb2, Cd72 and St8sia4, wherein the gene index of 1 is used for HTICs biomarkers which are up-regulated genes in TICs and the gene index of −1 for down-regulated genes in TICs; X is the log 2 transformed and median-centered and/or normalized RNA expression level for each HTICs biomarker (n).

8. The method of claim 7, wherein the adjuvant anti-HER2 treatment comprises trastuzamab, pertuzumab or lapatinib treatment.

9. The method of claim 7, wherein the HER2+ ERα negative breast cancer is node-positive.

* * * * *

SEQUENCE LISTING

```
<160> NUMBER OF SEQ ID NOS: 17

<210> SEQ ID NO 1
<211> LENGTH: 100
<212> TYPE: DNA
<213> ORGANISM: Homo Sapiens

<400> SEQUENCE: 1
agatgctcta atgtactgcc atgggaagaa ggtgattcac agagacataa agccagaaaa      60
tctgctctta gggctcaagg gagagctgaa gattgctgac                           100

<210> SEQ ID NO 2
<211> LENGTH: 100
<212> TYPE: DNA
<213> ORGANISM: Homo Sapiens

<400> SEQUENCE: 2
cgggacaaag ctggcctgaa tcattaatac gaaagactgg atatacctg gaaagtctta       60 agccttgtct catggacctt caccagacct acctcaaagc                            100

<210> SEQ ID NO 3
<211> LENGTH: 100
<212> TYPE: DNA
<213> ORGANISM: Homo Sapiens

<400> SEQUENCE: 3
tcccattttc catgcgctgt gcttatgtgt ggtggactgc agagctgctt ccacttacag      60
gagagctgat aatttgttag ctggaaccta ttcacttccg                            100
```

<210> SEQ ID NO 4
<211> LENGTH: 100
<212> TYPE: DNA
<213> ORGANISM: Homo Sapiens

<400> SEQUENCE: 4
agagatatgg aaaacgatcc agcccagaga cactgatttc agacctcttg atgagagaaa    60
gcacagaaaa tgttcccaga actcggcttg aagaccctgc                         100

<210> SEQ ID NO 5
<211> LENGTH: 100
<212> TYPE: DNA
<213> ORGANISM: Homo Sapiens

<400> SEQUENCE: 5
agtcaaagtc tcactcagca accaagaggc cgtcatcact tatcagcctt atctcattca    60
gcccgaagac ctcagggacc atgtaaatga catgggattt                         100

<210> SEQ ID NO 6
<211> LENGTH: 100
<212> TYPE: DNA
<213> ORGANISM: Homo Sapiens

<400> SEQUENCE: 6
ggagaggcaa gaagctaccg gatgtttcac gacgacagca tgaagtcttt cttccgtaga    60
ctgagtttca ctcccgacgg atctttgctt ctcacgccag                         100

<210> SEQ ID NO 7
<211> LENGTH: 100
<212> TYPE: DNA
<213> ORGANISM: Homo Sapiens

<400> SEQUENCE: 7
aacttgagga agagcaagca gtcagaccaa aatacctact gggtcgggaa gtcactggaa    60
acatgagagc catcctaatt gactggctag tacaggttca                         100

<210> SEQ ID NO 8
<211> LENGTH: 100
<212> TYPE: DNA
<213> ORGANISM: Homo Sapiens

<400> SEQUENCE: 8
agctacagat actcgatacc ttcccatcgc acaacccaaa aaagttatca caccggaaag    60
aagtcaccga gcgtctactc cagaagtcag tatgtgtagt                         100

<210> SEQ ID NO 9
<211> LENGTH: 100
<212> TYPE: DNA
<213> ORGANISM: Homo Sapiens

<400> SEQUENCE: 9
gcctcgctgc tttcttttct ccaagacggg ctgaggattg tacagctcta ggcggagttg    60
gggctcttcg gatcgcttag attctcctct ttgctgcatt                         100

<210> SEQ ID NO 10
<211> LENGTH: 100
<212> TYPE: DNA
<213> ORGANISM: Homo Sapiens

```
<400> SEQUENCE: 10
acattctgtt gtgctcatat catgcaaatt atcactagta ggagagcaga gagtggaaat      60
gttccaggta taaagaccca caagataaag aagctcagag                           100

<210> SEQ ID NO 11
<211> LENGTH: 100
<212> TYPE: DNA
<213> ORGANISM: Homo Sapiens

<400> SEQUENCE: 11
aactcactac tgggcatgga gggtgccaac agcatctttt ccgggttcct gctctttcca      60
gatatggagg cctgacctgt gggctgcttc acatccaccc                           100

<210> SEQ ID NO 12
<211> LENGTH: 100
<212> TYPE: DNA
<213> ORGANISM: Homo Sapiens

<400> SEQUENCE: 12
ttcagccccc agcccctccc ccatctccca ccctgtacct catcccatga gaccctggtg      60
cctggctctt tcgtcaccct tggacaagac aaaccaagtc                           100

<210> SEQ ID NO 13
<211> LENGTH: 100
<212> TYPE: DNA
<213> ORGANISM: Homo Sapiens

<400> SEQUENCE: 13
cagacttccc tgaatgtatt gaacttggaa agaaatgccc atctatgtcc cttgctgtga      60
gcaagaagtc aaagtaaaac ttgctgcctg aagaacagta                           100

<210> SEQ ID NO 14
<211> LENGTH: 100
<212> TYPE: DNA
<213> ORGANISM: Homo Sapiens

<400> SEQUENCE: 14
gcatttcttg ttccaagatc acccttctga gtacctctct ggctgccaaa ttgccagggc      60
cttcacagtt tgattccatt tctcagctcc aagcattagg                           100

<210> SEQ ID NO 15
<211> LENGTH: 100
<212> TYPE: DNA
<213> ORGANISM: Homo Sapiens

<400> SEQUENCE: 15
catcgacctg tactatctga tggacctctc ctactccatg cttgatgacc tcaggaatgt      60
caagaagcta ggtggcgacc tgctccgggc cctcaacgag                           100

<210> SEQ ID NO 16
<211> LENGTH: 100
<212> TYPE: DNA
<213> ORGANISM: Homo Sapiens

<400> SEQUENCE: 16
gaagttgact gatgatacac aacgcactag gacttatgct caaagctcaa aatgtaacaa      60
ggtacataaa acttggtcat ggtggacact ggagtcagag                           100
```

```
<210> SEQ ID NO 17
<211> LENGTH: 100
<212> TYPE: DNA
<213> ORGANISM: Homo Sapiens

<400> SEQUENCE: 17
atctacatag cctcctacct gaagtttcac caatgaagaa tcgcaggttt aagacctgtg    60
cagttgttgg aaattctggc attctgttag acagtgaatg                         100
```